(12) United States Patent
Bondy et al.

(10) Patent No.: US 7,648,998 B2
(45) Date of Patent: Jan. 19, 2010

(54) IMIDAZO 4,5-C PYRIDINE COMPOUNDS AND METHODS OF ANTIVIRAL TREATMENT

(75) Inventors: Steven S. Bondy, Danville, CA (US); Eric Davis Dowdy, Foster City, CA (US); Choung U. Kim, San Carlos, CA (US); David A. Oare, Belmont, CA (US); Johan Neyts, Kessel-Lo (BE); Vahid Zia, San Carlos, CA (US); Gerhard Pürstinger, Igls (AU)

(73) Assignees: K.U. Leuven Research & Development, Leuven (BE); Gilead Sciences, Inc., Foster City, CA (US)

( * ) Notice: Subject to any disclaimer, the term of this patent is extended or adjusted under 35 U.S.C. 154(b) by 160 days.

(21) Appl. No.: 10/583,814

(22) PCT Filed: Dec. 21, 2004

(86) PCT No.: PCT/US2004/043112

§ 371 (c)(1),
(2), (4) Date: Jun. 4, 2007

(87) PCT Pub. No.: WO2005/063744

PCT Pub. Date: Jul. 14, 2005

(65) Prior Publication Data

US 2007/0244148 A1    Oct. 18, 2007

Related U.S. Application Data

(60) Provisional application No. 60/590,990, filed on Jul. 26, 2004, provisional application No. 60/590,989, filed on Jul. 26, 2004, provisional application No. 60/591,024, filed on Jul. 26, 2004, provisional application No. 60/591,069, filed on Jul. 26, 2004, provisional application No. 60/533,963, filed on Jan. 2, 2004, provisional application No. 60/532,292, filed on Dec. 22, 2003.

(51) Int. Cl.
*C07D 471/04* (2006.01)
*A61K 31/437* (2006.01)

(52) U.S. Cl. ............................. 514/303; 546/118
(58) Field of Classification Search ............... 546/118; 514/303
See application file for complete search history.

(56) References Cited

U.S. PATENT DOCUMENTS

| | | | |
|---|---|---|---|
| 2,191,978 A | 2/1940 | Balle et al. | |
| 2,411,662 A | 11/1946 | Martin et al. | |
| 2,516,674 A | 7/1950 | Havertown et al. | |
| 2,548,863 A | 4/1951 | Havertown et al. | |
| 3,985,891 A | 10/1976 | Kutter et al. | |
| 4,358,387 A | 11/1982 | Zoleski et al. | |
| 4,565,816 A | 1/1986 | Neumann | |
| 4,692,443 A | 9/1987 | Katner | |
| 4,804,658 A | 2/1989 | Manley et al. | |
| 4,914,108 A | 4/1990 | Khanna et al. | |
| 4,988,707 A | 1/1991 | Stealey et al. | |
| 4,990,518 A | 2/1991 | Khanna et al. | |
| 5,011,832 A | 4/1991 | Dininno et al. | |
| 5,019,581 A | 5/1991 | Khanna et al. | |
| 5,057,517 A | 10/1991 | Johnston et al. | |
| 5,137,896 A | 8/1992 | Van Daele et al. | |
| 5,208,242 A | 5/1993 | Khanna et al. | |
| 5,227,384 A | 7/1993 | Khanna et al. | |
| 5,302,601 A | 4/1994 | Khannal et al. | |
| 5,332,744 A | 7/1994 | Chakravarty et al. | |
| 5,374,638 A | 12/1994 | Dhanoa et al. | |
| 5,405,964 A | 4/1995 | Mederski et al. | |
| 5,438,063 A | 8/1995 | Osswald et al. | |
| 5,446,032 A | 8/1995 | Whittaker et al. | |
| 5,486,525 A | 1/1996 | Summers, Jr. et al. | |
| 5,585,492 A | 12/1996 | Chandrakumar et al. | |
| 5,587,372 A | 12/1996 | Aszodi et al. | |
| 5,607,944 A | 3/1997 | Linz et al. | |
| 5,719,306 A * | 2/1998 | Chandrakumar et al. | ...... 560/19 |
| 5,723,492 A * | 3/1998 | Chandrakumar et al. | .... 514/539 |
| 5,854,265 A | 12/1998 | Anthony | |

(Continued)

FOREIGN PATENT DOCUMENTS

AU    643289    6/1991

(Continued)

OTHER PUBLICATIONS

Grazul et al., Natural Product Letters (1994), 5(3), 187-95.*

(Continued)

*Primary Examiner*—D. Margaret Seaman
*Assistant Examiner*—Niloofar Rahmani
(74) *Attorney, Agent, or Firm*—Clark & Elbing LLP

(57) ABSTRACT

The present invention relates to a pharmaceutical composition for the treatment or prevention of viral infections comprising as an active principle at least one imidazo[4,5-c]pyridine prodrug having the general Formula (A) wherein the substituents are described in the specification. The invention also relates to processes for the preparation and screening of compounds according to the invention having above mentioned general Formula and their use in the treatment or prophylaxis of viral infections.

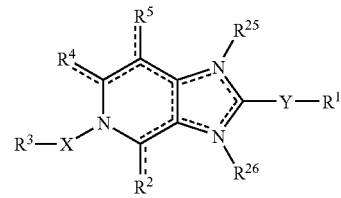

(A)

33 Claims, No Drawings

U.S. PATENT DOCUMENTS

| | | | |
|---|---|---|---|
| 5,859,035 A | 1/1999 | Anthony et al. |
| 5,872,136 A | 2/1999 | Anthony et al. |
| 5,874,452 A | 2/1999 | Anthony |
| 5,880,140 A | 3/1999 | Anthony |
| 5,883,105 A | 3/1999 | Anthony |
| 5,939,557 A | 8/1999 | Anthony et al. |
| 6,051,574 A | 4/2000 | Anthony |
| 6,063,930 A | 5/2000 | Dinsmore et al. |
| 6,080,870 A | 6/2000 | Anthony et al. |
| 6,329,381 B1 | 12/2001 | Kurimoto et al. |
| 6,376,515 B2 | 4/2002 | Zhu et al. |
| 6,479,508 B1 | 11/2002 | Beaulieu et al. |
| 6,492,384 B1 | 12/2002 | Mederski et al. |
| 6,627,651 B1 | 9/2003 | Shiraishi |
| 6,767,654 B2 | 7/2004 | Tamao et al. |
| 6,770,666 B2 | 8/2004 | Hashimoto et al. |
| 6,803,374 B2 | 10/2004 | Priestley et al. |
| 6,835,739 B2 | 12/2004 | Zhu et al. |
| 6,844,367 B1 | 1/2005 | Zhu et al. |
| 7,026,051 B2 | 4/2006 | Schauer et al. |
| 7,098,231 B2 | 8/2006 | Poupart et al. |
| 7,112,600 B1 | 9/2006 | Hashimoto et al. |
| 7,223,785 B2 | 5/2007 | Beaulieu et al. |
| 7,285,551 B2 | 10/2007 | Hashimoto et al. |
| 7,294,457 B2 | 11/2007 | Kukolj et al. |
| 2003/0073836 A1 | 4/2003 | Priepke et al. |
| 2003/0108862 A1 | 6/2003 | Kukolj et al. |
| 2004/0082635 A1 | 4/2004 | Hashimoto et al. |
| 2004/0097438 A1 | 5/2004 | Hashimoto et al. |
| 2004/0097574 A1 | 5/2004 | Marshall |
| 2004/0171626 A1 | 9/2004 | Beaulieu et al. |
| 2004/0186125 A1 | 9/2004 | Poupart et al. |
| 2005/0026921 A1 | 2/2005 | Eckhardt et al. |
| 2005/0096337 A1 | 5/2005 | Ackermann et al. |
| 2005/0222198 A1 | 10/2005 | Bondy et al. |
| 2005/0239821 A1 | 10/2005 | Neyts et al. |
| 2006/0052602 A1 | 3/2006 | Kim et al. |
| 2006/0229336 A1 | 10/2006 | Kazmierski et al. |
| 2006/0252791 A1* | 11/2006 | Bondy et al. ............ 514/303 |
| 2007/0021472 A1 | 1/2007 | Zhu et al. |
| 2007/0032497 A1 | 2/2007 | Hashimoto et al. |
| 2008/0188516 A1 | 8/2008 | Bondy et al. |
| 2008/0199427 A1 | 8/2008 | Bondy |
| 2009/0036460 A1 | 2/2009 | Dowdy et al. |

FOREIGN PATENT DOCUMENTS

| | | |
|---|---|---|
| CA | 2093290 | 7/1993 |
| CA | 2158996 | 3/1994 |
| CA | 2357771 | 7/2000 |
| CA | 2471566 | 1/2003 |
| CA | 2423800 | 3/2003 |
| CA | 2496249 | 8/2003 |
| DE | 4211474 | 10/1993 |
| DE | 4230464 | 3/1994 |
| DE | 4236026 | 6/1994 |
| DE | 4309969 | 9/1994 |
| DE | 4318813 | 12/1994 |
| EP | 0 076 530 A | 4/1983 |
| EP | 0138552 | 4/1985 |
| EP | 0228845 | 7/1987 |
| EP | 0232937 | 8/1987 |
| EP | 0300726 | 1/1989 |
| EP | 0 344 414 A | 12/1989 |
| EP | 0 417 745 A | 3/1991 |
| EP | 0462009 | 12/1991 |
| EP | 0510260 | 10/1992 |
| EP | 0605836 | 7/1994 |
| EP | 0706795 | 4/1996 |
| EP | 1 132 381 A | 9/2001 |
| EP | 1162196 | 12/2001 |
| EP | 1386923 | 2/2004 |
| EP | 1400241 | 2/2004 |
| GB | 2 158 440 A | 11/1985 |
| GB | 2264115 | 8/1993 |
| HU | 78019 | 5/1999 |
| IL | 89588 | 3/1989 |
| SU | 813921 | 12/1986 |
| SU | 1048742 | 12/1986 |
| SU | 851940 | 4/1988 |
| SU | 860463 | 5/1998 |
| WO | WO-92/22556 | 12/1992 |
| WO | WO-93/02080 | 2/1993 |
| WO | WO-93/14072 | 7/1993 |
| WO | WO-93/16075 | 8/1993 |
| WO | WO-94/12461 | 6/1994 |
| WO | WO-94/29321 | 12/1994 |
| WO | WO-95/02597 | 1/1995 |
| WO | WO-95/16687 | 6/1995 |
| WO | WO-96/11192 | 4/1996 |
| WO | WO 96/12703 A | 5/1996 |
| WO | WO-96/15111 | 5/1996 |
| WO | WO 99/27929 A | 6/1999 |
| WO | WO-00/20400 | 4/2000 |
| WO | WO-00/20416 | 4/2000 |
| WO | WO-00/20425 | 4/2000 |
| WO | WO-00/20445 | 4/2000 |
| WO | WO-00/39127 | 7/2000 |
| WO | WO-00/40583 | 7/2000 |
| WO | WO-00/40586 | 7/2000 |
| WO | WO-00/73307 | 12/2000 |
| WO | WO-01/60315 | 8/2001 |
| WO | WO-01/66526 | 9/2001 |
| WO | WO-01/85172 | 11/2001 |
| WO | WO-01/95910 | 12/2001 |
| WO | WO-02/04425 | 1/2002 |
| WO | WO-02/057425 | 7/2002 |
| WO | WO-02/067942 | 9/2002 |
| WO | WO-03/000254 | 1/2003 |
| WO | WO-03/004020 | 1/2003 |
| WO | WO-03/007945 | 1/2003 |
| WO | WO-03/010140 | 2/2003 |
| WO | WO-03/010141 | 2/2003 |
| WO | WO-03/014229 | 2/2003 |
| WO | WO-03/026587 | 4/2003 |
| WO | WO-03/057205 | 7/2003 |
| WO | 2004005286 * | 1/2004 |
| WO | WO 2004/005286 A | 1/2004 |
| WO | WO-2004/018468 | 3/2004 |
| WO | WO-2004/019935 | 3/2004 |
| WO | WO-2004/033455 | 4/2004 |
| WO | WO-2004/043913 | 5/2004 |
| WO | WO-2004/054974 | 7/2004 |
| WO | 2004067516 * | 8/2004 |
| WO | WO-2004/072243 | 8/2004 |
| WO | WO-2005/063744 | 7/2005 |
| WO | WO-2006/029966 | 3/2006 |
| WO | WO-2006/033703 | 3/2006 |
| WO | WO-2006/069193 | 6/2006 |
| WO | WO-2008/005519 | 1/2008 |
| WO | WO-2009/009001 | 1/2009 |

OTHER PUBLICATIONS

Kiyama et al., "Synthesis and Evaluation of Novel Nonpeptide Angiotensin II Receptor Antagonists: Imidazo[4,5-c]pyridine Derivatives with an Aromatic Substituent," Chem. Pharm. Bull., 43(3): 450-460(1995).

Penning et al., "Synthesis of Imidazopyridines and Purines as Potent Inhibitors of Leukotriene A4 Hydrolase," Bioorganic and Medicinal Chemistry Letters, 13: 1137-1139 (2003).

Yutilov et al., "Synthesis and antiviral activity of spinaceamine derivatives," *Khimiko Farmatsevticheskii Zhurnal* 23(1): 56-59. 1989.
Translation of Yutilov et al., "Synthesis and antiviral activity of spinaceamine derivatives," Khimiko Farmatsevticheskii Zhurnal 23(1): 56-59.
International Search Report (PCT/US2004/043112) dated Jul. 5, 2005.
Written Opinion (PCT/US/2004/043112) dated Oct. 18, 2005.
U.S. Appl. No. 11/658,625, filed Jul. 26, 2005, Kim et al.
U.S. Appl. No. 12/303,207, filed Feb. 12, 2008, Steven S. Bondy.
Akamatsu et al., "New Efficient Route for Solid-Phase Synthesis of Benzimidazole Derivatives," *J. Comb. Chem.* 4:475-483 (2002).
Baba et al., "Synergistic Antiviral Effects of Antiherpes Compounds and Human Leukocyte Interferon on Varicella-Zoster Virus In Vitro," *Antimicrobial Agents Chemother.* 25:515-517, 1984.
Baginski et al., "Mechanism of Action of a Pestivirus Antiviral Compound," *Proc. Natl. Acad. Sci. U.S.A.* 97:7981-7986, 2000.
Barlin and Fenn, "A Carbon-13 Nuclear Magnetic Resonance Study of Protonation in Imidazo[4,5-c]pyridines," *Aust. J. Chem.* 34:1341-1344(1981).
Barlin and Fenn, "The Preparation and 1H NMR Spectra of Some N-Methylpurines and Related Compounds," *Aust. J. Chem.* 36:633-638 (1983).
Barlin, "Ionisation Constants of Heterocyclic Substances, Part VIII. 1,3,5-Triazindenes," *J. Chem. Soc. B: Phys. Org.* 4:285-291, 1966.
Barraclough et al "An Adventitious Synthesis of a 5-Methylimidazo[4,5-c]pyridine Derivative," *Tet. Lett.* 27:5997-6000 (1986).
Barraclough et al., "Inotropic "A" Ring Substituted Sulmazole and Isomazole Analogues," *J. Med. Chem.* 33:2231-2239 (1990).
Brown et al., "Purine Analogues as Amplifiers of Phleomycin. V. Thioethers of Several Heterocyclic Systems with One or Two Rings," *Aust. J. Chem.* 32:2713-2726 (1979).
Chou et al., "Quantitative Analysis of Dose-Effect Relationships: The Combined Effects of Multiple Drugs or Enzyme Inhibitors," *Adv. Enzyme Reg.* 22:27-55, 1984.
Cleve et al., "Derivate des Imidazo[4,5-b]- und Imidazo[4,5-c]-Pyridins," *Liebigs Ann. Chem.* 747:158-171, 1971 (and translation).
Curtin et al., "Discovery and Evaluation of a Series of 3-Acylindole Imidazopyridine Platelet-Activating Factor Anatagonists," *J. Med. Chem.* 41:74-95(1998).
Elion et al., "Antagonists of Nucleic Acid Derivatives. VIII. Synergism in Combinations of Biochemically Related Antimetabolites," J. Biol. Chem. 208:477-488, 1954.
Final Rejection, Dec. 16, 2008, U.S. Appl. No. 11/019,830.
Final Rejection, Mar. 19, 2007, U.S. Appl. No. 11/316,050.
Fletcher et al., "Heterocyclic Systems," *Nomenclature of Organic Adv. Ser.* pp. 49-64, 1974.
Greenfield et al., "Increase in the Stability and Helical Content of Estrogen Receptor Alpha in the Presence of the Estrogen Response Element: Analysis by Circular Dichroism Spectroscopy," *Biochemistry* 40:6646-6652, 2001.
Griesser, Chapter 8, The Importance of Solvates (pp. 211-230), In the text, Polymorphism: In the Pharmaceutical Industry, Hilfiker, 2006.
Guillory (in Britain ed.) "Polymorphism etc." NY:marcel Dekker Inc. 1999, 1-2, 183-226.
International Preliminary Examination Report (PCT/BE03/00117) (mailed Sep. 3, 2004).
International Preliminary Report on Patentability for PCT/US2004/043112 dated Apr. 25, 2006.
International Preliminary Report on Patentability for PCT/US2005/026606 dated Feb. 20, 2007.
International Preliminary Report on Patentability for PCT/US2005/046477 dated Mar. 16, 2007.
International Preliminary Report on Patentability for PCT/US2007/015553 dated Jan. 13, 2009.
International Search Report for PCT/BE2003/000117 dated Dec. 16, 2003.
International Search Report for PCT/US2005/026606 dated Feb. 13, 2006.
International Search Report for PCT/US2005/046477 dated Jun. 2, 2006.
International Search Report for PCT/US2007/015553 dated Mar. 6, 2008.
International Search Report for PCT/US2008/008259 dated Oct. 14, 2008.
Jacob III, P., "Resolution of (+/-) 5-Bromonornicotine. Sythesis of (R)- and (S)- Nornicotine of High Enantiomeric Purity," *J. Org. Chem.* 47:4165-4167, 1982.
Johnson, A.W. Invitation to Organic Chemistry 1999 Jones and Bartlett: Missisauga, Canada p. 24.
Jones, Maitland Organic Chemistry Norton: New York, 1997, p. 84-99.
Kariv et al., "Improvement of 'Hit-to-Lead' Optimization by Integration of In Vitro HTS Experimental Models for Early Determination of Pharmacokinetic Properties," *Comb. Chem. High Throughput Screen.* 5:459-472, 2002.
Kuno et al (1993) "Studies on Cerebral Protective Agents, IV. Synthesis of Novel 4-Arylpyridine and4-arylpyridazine Derivatives with Anti-Anoxic Activity," Chem Phar. Bull. 41(1):136-162.
Lindenbach et al. (2005) "Unraveling Hepatitis C Virus Replication from Genome to Function," Nature 436-:933-938.
Lochmüller et al., "Chromatographic Resolution of Enantiomers Selective Review," *J. Chromatography* 113:283-302, 1975.
Mederski and Pachler, "Synthesis and Structural Assignment of Some N-Substituted Imidazopyridine Derivatives," *Tetrahedron* 48:10549-10558 (1992).
Montgomery et al., "1-B-D-Arabinofuranosyl, etc.," J. Med. Chem., 1982,25,96-98.
Non-Final Rejection, Dec. 12, 2008, U.S. Appl. No. 10/519,756.
Non-Final Rejection, Mar. 12, 2008, U.S. Appl. No. 11/019,830.
Non-Final Rejection, Mar. 25, 2009, U.S. Appl. No. 12/022,557.
Non-Final Rejection, Oct. 29, 2008, U.S. Appl. No. 11/825,598.
Non-Final Rejection, Sep. 27, 2006, U.S. Appl. No. 11/316,050.
Okamoto et al., "Optical Resolution of Dihydropyridine Enantiomers by High-Performance Liquid Chromatography Using PhenylCarbamates of Polysaccharides as a Chiral Stationary Phase," *J. Chromatography* 513:375-378, 1990.
Paeshuyse et al., "A Novel, Highly Selective, etc.," J of Virology, Jan. 2006, 80(1), 149-160.
Puerstinger et al. "Substituted 5-benzyl-2-phenyl-5H-imidazo[4,5-c]pyridines: A new class of pestivirus inhibitors" Bioorganic & Medicinal Chemistry Letters 2006, 16:5345-5349.
Puertstinger et al. "Antiviral 2,5-disubstituted imidazo[4,5-c]pyridines: From anti-pestivirus to anti-hepatitis C virus activity" Bioorganic & Medicinal Chemistry Letters 2007, 17:391-393.
Rigaudy et al., "Fundamental Heterocyclic Systems," *Nomenclature of Organic Adv. Ser.* pp. 53-76, 1979.
Robertson et al., "Structure-Activity Relationships of Arylimidazopyridine Cardiotonics: Discovery and Inotropic Activity of 2-[2-Methoxy-4-(methylsulfinyl)phenyl]-1*H*-imidazo[4,5-c]pyridine," *J. Med. Chem.* 28:717-727 (1985).
Savarino et al., "Spectral Behaviour of Linked Heterocyclic Systems and Related Dyes," *Spectrochim. Acta A: Mol. Biomol. Spectrosc.* 49A:1379-1393 (1993).
Self et al. (1991) "Romzarit: A Potential Disease-Modifying Antirheumatic Drug," J. Med. Chem. 34:772-777.
Siddiqui et al., "3-Deaza- and, etc.," J. Med. Chem., 1995, 38, 1035-1038.
Stanovnik et al., "Methylation of Heterocyclic Compounds Containing NH, SH, and/or OH Groups by Means of N,N-Dimethylformamide Dimethyl Acetal," *Aust. J. Chem.* 34:1729-1738(1981).
Vassilev et al., "Authentic and Chimeric Full-Length Genomic cDNA Clones of Bovine Viral Diarrhea Virus That Yield Infectious Transcripts," *J. Virol.* 71:471-478(1997).
Vippagunta et al. "Crystalline Solid" Advanced Drug Delivery Reviews 48:3-26 (2001).
Wang et al., "Non-Nucleoside Analogue Inhibitors Bind to an Allosteric Site on HCV NS5B Polymerase. Crystal Structures and Mechanism of Inhibition," *J. Biol. Chem.* 278:9489-9495 (2003).
Written Opinion for PCT/US2005/026606 dated Feb. 13, 2006.
Written Opinion for PCT/US2005/046477 dated Jun. 2, 2006.
Written Opinion for PCT/US2007/015553 dated Jan. 7, 2009.

Zhang, "Inhibitors of Hepatitis C—A Review of the Recent Patent Literature," *IDrugs* 5:154-158 (2002).

Zhang, "Studies on the Synthesis and Single Crystal Structure of 3-methyl-6-(p-methylphenyl) Pyridazine," 2001 Journal of Sichuan Normal University (Natural Science) 24(4):384-386 (and translation).

* cited by examiner

US 7,648,998 B2

IMIDAZO 4,5-C PYRIDINE COMPOUNDS AND METHODS OF ANTIVIRAL TREATMENT

CROSS-REFERENCE TO RELATED APPLICATIONS

This application is the U.S. National Stage of International Application No. PCT/US2004/043112, filed Dec. 21, 2004, which, in turn, claims the benefit of U.S. Provisional Patent Application Ser. Nos. 60/532,292 (filed Dec. 22, 2003), 60/533,963 (filed Jan. 2, 2004), 60/591,069 (filed Jul. 26, 2004), 60/591,024 (filed Jul. 26, 2004), 60/590,989 (filed Jul. 26, 2004), and 60/590,990 (filed Jul. 26, 2004); the disclosures of each are hereby incorporated by reference.

FIELD OF THE INVENTION

The present invention relates to a series of novel imidazo [4,5-c]pyridine compounds, processes for their preparation, their use to treat or prevent viral infections and their use to manufacture a medicine to treat or prevent viral infections, particularly infections with viruses belonging to the family of the Flaviviridae and Picornaviridae and more preferably infections with hepatitis-C-virus (HCV).

BACKGROUND OF THE INVENTION

The family of the Flaviviridae consists of 3 genera, the pestiviruses, the flaviviruses and the hepaciviruses and also contains the hepatitis G virus (HGV/GBV-C) that has not yet been assigned to a genus. Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. BVDV, the prototypic representative of the pestivirus genus is ubiquitous and causes a range of clinical manifestations, including abortion, teratogenesis, respiratory problems, chronic wasting disease, immune system dysfunction, and predisposition to secondary viral and bacterial infections and may also cause acute fatal disease. Fetuses of cattle can be infected persistently with BVDV, these animals remain viremic throughout life and serve as a continuous source for virus spread in herds.

Vaccines are used in some countries with varying degrees of success to control pestivirus disease. In other countries, animal culling and slaughter are used to contain pestivirus disease outbreaks.

The World Health Organization estimates that world-wide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1 to 5% of who may develop liver cancer during the next then years. The only treatment option available today is the use of interferon α-2 (or its pegylated from) either alone or combined with ribavirin. However, sustained response is only observed in about 40% of the patients and treatment is associated with serious adverse effects. There is thus an urgent need for potent and selective inhibitors of the replication of the HCV in order to treat infections with HCV. Furthermore, the study of specific inhibitors of HCV replication has been hampered by the fact that it is not possible to propagate HCV (efficiently) in cell culture. Since HCV and pestiviruses belong to the same virus family and share many similarities (organization of the genome, analogous gene products and replication cycle), pestiviruses have been adopted as a model and surrogate for HCV. For example, BVDV is closely related to hepatitis C virus (HCV) and used as a surrogate virus in drug development for HCV infection.

The compound 3-[((2-dipropylamino)ethyl)thio]-5H-1,2,4-triazino[5,6-b]indole has been reported to selectively inhibit the replication of BVDV and other pestiviruses (Baginski S G et al., *Proc. Natl. Acad. Sci.* U.S.A. 2000 Jul. 5; 97(14):7981-6). Currently, there is no treatment strategy available for controlling infections caused by pestiviruses.

Coxsackie viruses belong to the group of the enteroviruses, family of the Picornaviridae. They cause a heterogeneous group of infections including herpangina, aseptic meningitis, a common-cold-like syndrome, a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis.

Currently only pleconaril (3-13,5-dimethyl-4-[[3-methyl-5-isoxazolyl)propyl]phenyl]-5-(trifluoromethyl-1,2,4-oxadiazole)) and enviroxime (2-amino-1-(isopropylsulfonyl)-6-benzimidazole phenyl ketone oxime) have been studied clinically for the treatment of infections with enteroviruses. Pleconaril is a so called "capsid function-inhibitor"; enviroxime prevents the formation of the RNA replicative intermediate. Enviroxime resulted in only modest clinical and virological benefit in some studies and no benefits in others. Clinical response with pleconaril has been observed in some studies, but the compound has not been approved by the Food and Drug Administration (hearing of Mar. 18, 2002).

Relevant disclosures include U.S. Pat. Nos. 4,914,108; 4,988,707; 4,990,518; 5,137,896; 5,208,242; 5,227,384; 5,302,601; 5,374,638; 5,405,964; 5,438,063; 5,486,525; 6,479,508; and U.S. Patent Publication No. US2003/0108862 A1, Canadian Patent No. 2423800 A1, German Patent Nos. 4211474 A1, 4236026, 4309969, 4318813, European Patent Nos. EP 0 138 552 A2, EP 0 706 795 A2, EP 1 132 381 A1, Great Britain Patent No. 2158440 A, PCT Patent Publication Nos. WO 00/20416, WO 00/39127, WO 00/40583, WO 03/007945 A1, WO 03/010140 A2, WO 03/010141 A2, WO 93/02080, WO 93/14072, WO 96/11192, WO 96/12703, WO 99/27929, Akamatsu, et al., New Efficient Route for Solid-Phase Synthesis of Benzimidazole Derivatives", 4:475-483, *J. COMB. CHEM,* 2002, Cleve et al., "Derivate des Imidazo [4,5-b]- und Imidazo[4,5-c]pyridins", 747:158-171, *JUSTUS LIEBIGS AANALEN DER CHEMICA,* 1971, Kiyama, et al., "Synthesis and Evaluation of Novel Nonpeptide Angiotensin II Receptor Antagonists: Imidazo[4,5-c]pyridine Derivatives with an Aromatic Substituent", 43(3):450-60, *CHEM PHARM BULL,* 1995, Mederski et al., "Synthesis and Structural Assignment of Some N-substituted Imidazopyridine Derivatives", 48(48):10549-58, *TETRAHEDRON,* 1992, Yutilov et al., 23(1):56-9, *KHIMIKO-FARMAT-SEVTICHESKII ZHURNAL,* 1989. The disclosures of all citations set forth herein are expressly incorporated by reference to the extent such disclosures are relevant to the contents herein.

A need exists for compounds having antiviral and other desirable properties, such as bioavailability, efficacy, nontoxicity, optimal clearance, potency and the like. In particular, a need exists for compounds having selective activity against viruses belonging to the family of Flaviviridae including hepatitis C virus, and against viruses belonging to the family of Picornaviridae. These and other objects of this invention will be apparent to one skilled in the art from consideration of this specification as a whole.

SUMMARY OF THE INVENTION

An embodiment of the present invention provides compounds having the general formula (A),

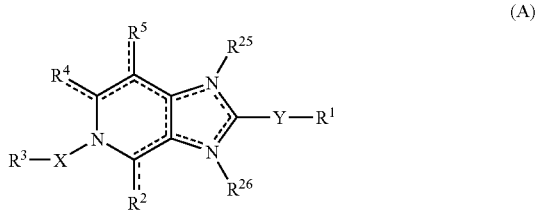

(A)

wherein:
the dotted lines represent an optional double bond, provided that no two double bonds are adjacent to one another, and that the dotted lines represent at least 3, optionally 4 double bonds;

$R^1$ is selected from hydrogen, aryl, heterocyclic, $C_1$-$C_{10}$ alkoxy, $C_1$-$C_{10}$ thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from single bond, O, $S(O)_m$, $NR^{11}$, or $C_{1-10}$ alkylene, $C_{2-10}$ alkenylene, $C_{2-10}$ alkynylene, wherein each may optionally include 1 to 3 heteroatoms selected from O, S or N;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic, provided that when one of $R^{25}$ or $R^{26}$ is present, then either $R^2$ or $R^4$ is selected from (=O), (=S), and =$NR^{27}$;

X is selected from $C_1$-$C_{10}$ alkylene, $C_{2-10}$ alkenylene or $C_{2-10}$ alkynylene, where each may include one or more heteroatoms selected from O, S, or N, provided any such heteroatom is not adjacent to the N in the ring;

m is any integer from 0 to 2;

$R^3$ is selected from aryl, aryloxy, arylthio, cycloalkyl, cycloalkenyl, cycloalkynyl, aryl-N($R^{10}$)—, or heterocyclic, where each said substituent may be optionally substituted with at least one $R^{17}$, provided that for cycloalkenyl the double bond is not adjacent to a nitrogen, and provided $R^3$-M-Q is not biphenyl;

$R^5$ is selected from hydrogen; $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=O)$OR^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —$CO_2R^{18}$, $NO_2$, —$NR^7R^8$, $C_{1-18}$ haloalkyl, C(=O)$R^{18}$, C(=S)$R^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$) alkylthio, heterocyclic, $C_{1-18}$ hydroxyalkyl, where each may be optionally substituted with at least 1 $R^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocyclic, —C(=O)$R^{12}$; —C(=S)$R^{12}$, an amino acid residue linked through a carboxyl group thereof, or where $R^7$ and $R^8$ together with the nitrogen form a heterocyclic;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —$NR^{15}R^{16}$, aryl, an amino acid residue linked through an amino group of the amino acid, $CH_2OCH$ (=O)$R^{9a}$, or $CH_2OC$(=O)$OR^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)$R^{12}$, heterocyclic, or an amino acid residue;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;

$R^{13}$ and $R^{14}$ are independently selected from hydrogen, $C_{1-18}$ alkyl, $C_{2-18}$ alkenyl, aryl, $C_{3-10}$ cycloalkyl, $C_{4-10}$ cycloalkenyl, —C(=O)$R^{12}$, —C(=S)$R^{12}$, or an amino acid residue;

$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;

$R^{17}$ is independently M-Q- wherein M is a ring optionally substituted with 1 or more $R^{19}$, and Q is a bond or a linking group connecting M to $R^3$ having 1 to 10 atoms and optionally substituted with 1 or more $R^{19}$;

$R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —$NO_2$, —$NR^{20}R^{21}$, $C_{1-18}$ haloalkyl, $C_{1-18}$ haloalkyloxy, —C(=O)$R^{18}$, —C(=O)$OR^{18}$, —OalkenylC(=O)$OR^{18}$, —OalkylC(=O)$NR^{20}R^{21}$, —OalkylOC(=O)$R^{18}$, —C(=S)$R^{18}$, SH, —C(=O)N($C_{1-6}$ alkyl), —N(H)S(O)(O)($C_{1-6}$ alkyl), aryl, heterocyclic, $C_{1-18}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio or aryl($C_{1-18}$)alkyl, where each may be optionally substituted with 1 or more =O, $NR^{20}R^{21}$, CN, $C_{1-18}$ alkoxy, heterocyclic, $C_{1-18}$ haloalkyl, heterocyclic alkyl, heterocyclic connected to $R^{17}$ by alkyl, alkoxyalkoxy or halogen;

$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)$R^{12}$, or —C(=S) $R^{12}$;

$R^{22}$ is selected from hydrogen, —OH, $C_{1-18}$ alkyl, $C_{2-18}$ alkenyl, $C_{1-18}$ alkoxy, —$NR^{23}R^{24}$, aryl, $C_{3-10}$ cycloalkyl, and $C_{4-10}$ cycloalkenyl;

$R^{23}$ and $R^{24}$ are independently selected from hydrogen, $C_{1-18}$ alkyl, or a heterocyclic formed by taking $C_{2-3}$ alkyl together with N of $R^{22}$, which heterocyclic is optionally substituted with OH or aryl, or an amino acid residue linked through a carboxyl group of the amino acid;

$R^{25}$ and $R^{26}$ are not present, or are independently selected from hydrogen, $C_{1-18}$ alkyl, $C_{3-10}$ cycloalkyl, aryl, heterocyclic, where each is optionally independently substituted with 1 to 4 of $C_{1-6}$ alkyl, $C_{1-6}$ alkoxy, halo, $CH_2OH$, benzyloxy, and OH; and $R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and aryl $C_{1-18}$ alkyl, and salts, tautomers, isomers and solvates thereof.

Another embodiment of the present invention provides compounds having the general formula (A),

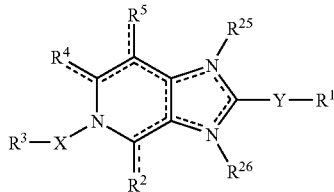

(A)

wherein:
the dotted lines represent an optional double bond, provided that no two double bonds are adjacent to one another, and that the dotted lines represent at least 3, optionally 4 double bonds;

$R^1$ is selected from hydrogen, aryl, heterocyclic, $C_1$-$C_{10}$ alkoxy, $C_1$-$C_{10}$ thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from single bond, O, S(O)$_m$, NR$^{11}$, or $C_{1-10}$ alkylene, $C_{2-10}$ alkenylene, $C_{2-10}$ alkynylene, wherein each may optionally include 1 to 3 heteroatoms selected from O, S or N;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic, provided that when one of $R^{25}$ or $R^{26}$ is present, then either $R^2$ or $R^4$ is selected from (=O), (=S), and =NR$^{27}$;

X is selected from $C_1$-$C_{10}$ alkylene, $C_{2-10}$ alkenylene or $C_{2-10}$ alkynylene, where each may include one or more heteroatoms selected from O, S, or N, provided any such heteroatom is not adjacent to the N in the ring;

m is any integer from 0 to 2;

$R^3$ is a heterocycle optionally substituted with at least one $R^{17}$ provided, however, that $R^3$ optionally substituted with at least one $R^{17}$ is not pyridinyl or 5-chlorothienyl, provided that $R^3$-MQ is not biphenyl;

$R^5$ is selected from hydrogen; $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic;

$R^6$ is selected from hydrogen, $C_{1-18}$ alkyl, $C_{2-18}$ alkenyl, $C_{2-18}$ alkynyl, heterocyclic, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —CO$_2$R$^{18}$, NO$_2$, —NR$^7$R$^8$, $C_{1-18}$ haloalkyl, C(=O)R$^{18}$, C(=S)R$^{18}$, SH, aryl, aryloxy, arylthio, arylsulfoxide, arylsulfone, arylsulfonamide, aryl(C$_{1-18}$)alkyl, aryl(C$_{1-18}$)alkyloxy, aryl(C$_{1-18}$)alkylthio, $C_{1-18}$ hydroxyalkyl, where each may be optionally substituted with at least 1 R$^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocyclic, —C(=O)R$^{12}$; —C(=S)R$^{12}$, an amino acid residue linked through a carboxyl group thereof, or where $R^7$ and $R^8$ together with the nitrogen form a heterocyclic;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, an amino acid residue linked through an amino group of the amino acid, CH$_2$OCH(=O)R$^{9a}$, or CH$_2$OC(=O)OR$^{9a}$ where R$^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, heterocyclic, or an amino acid residue;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;

$R^{13}$ and $R^{14}$ are independently selected from hydrogen, $C_{1-18}$ alkyl, $C_{2-18}$ alkenyl, aryl, $C_{3-10}$ cycloalkyl, $C_{4-10}$ cycloalkenyl, —C(=O)R$^{12}$, —C(=S)R$^{12}$, or an amino acid residue;

$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;

$R^{17}$ is independently selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, CO$_2$H, CO$_2$R$^{18}$, NO$_2$, NR$^7$R$^8$, haloalkyl, C(=O)R$^{18}$, C(=S)R$^{18}$, SH, aryl, aryloxy, arylthio, arylsulfoxide, arylsulfone, arylsulfonamide, arylalkyl, arylalkyloxy, arylalkylthio, heterocyclic, $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or $C_{1-18}$ hydroxyalkyl is optionally substituted with 1 or more R$^{19}$;

$R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —NO$_2$, —NR$^{20}$R$^{21}$, $C_{1-18}$ haloalkyl, $C_{1-18}$ haloalkyloxy, —C(=O)R$^{18}$, —C(=O)OR$^{18}$, —OalkenylC(=O)OR$^{18}$, —OalkylC(=O)NR$^{20}$R$^{21}$, —OalkylOC(=O)R$^{18}$, —C(=S)R$^{18}$, SH, —C(=O)N(C$_{1-6}$ alkyl), —N(H)S(O)(O)(C$_{1-6}$ alkyl), aryl, heterocyclic, $C_{1-18}$alkylsulfone, arylsulfoxide, arylsulfonamide, aryl(C$_{1-18}$)alkyloxy, aryloxy, aryl(C$_{1-18}$ alkyl)oxy, arylthio, aryl(C$_{1-18}$)alkylthio or aryl(C$_{1-18}$)alkyl, where each may be optionally substituted with 1 or more =O, NR$^{20}$R$^{21}$, CN, $C_{1-18}$ alkoxy, heterocyclic, $C_{1-18}$ haloalkyl, heterocyclic alkyl, heterocyclic connected to R$^{17}$ by alkyl, alkoxyalkoxy or halogen;

$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)R$^{12}$, carboxylester-substituted heterocyclic or —C(=S)R$^{12}$;

$R^{22}$ is selected from hydrogen, —OH, $C_{1-18}$ alkyl, $C_{2-18}$ alkenyl, $C_{1-18}$ alkoxy, —NR$^{23}$R$^{24}$, aryl, $C_{3-10}$ cycloalkyl, and $C_{4-10}$ cycloalkenyl;

$R^{23}$ and $R^{24}$ are independently selected from hydrogen, $C_{1-18}$ alkyl, or a heterocyclic formed by taking $C_{2-3}$ alkyl together with N of R$^{22}$, which heterocyclic is optionally substituted with OH or aryl, or an amino acid residue linked through a carboxyl group of the amino acid;

$R^{25}$ and $R^{26}$ are not present, or are independently selected from hydrogen, $C_{1-18}$ alkyl, $C_{3-10}$ cycloalkyl, aryl, heterocyclic, where each is optionally independently substituted with 1 to 4 of $C_{1-6}$ alkyl, $C_{1-6}$ alkoxy, halo, $CH_2OH$, benzyloxy, and OH; and $R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and aryl $C_{1-18}$ alkyl, and the salts, tautomers, isomers and solvates thereof.

An embodiment of the present invention provides compounds having the general formula (A),

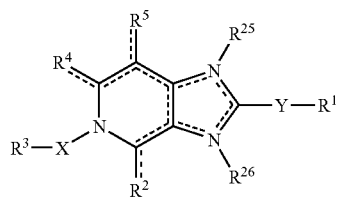

wherein:

the dotted lines represent an optional double bond, provided that no two double bonds are adjacent to one another, and that the dotted lines represent at least 3, optionally 4 double bonds;

$R^1$ is selected from hydrogen, aryl, heterocyclic, $C_1$-$C_{10}$ alkoxy, $C_1$-$C_{10}$ thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from single bond, O, $S(O)_m$, $NR^{11}$, or $C_{1-10}$ alkylene, $C_{2-10}$ alkenylene, $C_{2-10}$ alkynylene, wherein each may optionally include 1 to 3 heteroatoms selected from O, S or N;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic, provided that when one of $R^{25}$ or $R^{26}$ is present, then either $R^2$ or $R^4$ is selected from (=O), (=S), and =$NR^{27}$;

X is selected from $C_1$-$C_{10}$ alkylene, $C_{2-10}$ alkenylene or $C_{2-10}$ alkynylene, where each may include one or more heteroatoms selected from O, S, or N, provided any such heteroatom is not adjacent to the N in the ring;

m is any integer from 0 to 2;

$R^3$ is a heterocycle optionally substituted with at least one $R^{17}$, provided $R^3$-M-Q is not biphenyl;

$R^5$ is selected from hydrogen; $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=O)O$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocyclic;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —$CO_2R^{18}$, $NO_2$, —$NR^7R^8$, $C_{1-18}$ haloalkyl, C(=O)$R^{18}$, C(=S)$R^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$) alkylthio, heterocyclic, $C_{1-18}$ hydroxyalkyl, where each may be optionally substituted with at least 1 $R^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocyclic, —C(=O)$R^{12}$; —C(=S)$R^{12}$, an amino acid residue linked through a carboxyl group thereof, or where $R^7$ and $R^8$ together with the nitrogen form a heterocyclic;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —$NR^{15}R^{16}$, aryl, an amino acid residue linked through an amino group of the amino acid, $CH_2OCH(=O)R^{9a}$, or $CH_2C(=O)OR^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)$R^{12}$, heterocyclic, or an amino acid residue;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;

$R^{13}$ and $R^{14}$ are independently selected from hydrogen, $C_{1-18}$ alkyl, $C_{2-18}$ alkenyl, aryl, $C_{3-10}$ cycloalkyl, $C_{4-10}$ cycloalkenyl, —C(=O)$R^{12}$, —C(=S)$R^{12}$, or an amino acid residue;

$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;

$R^{17}$ is M-Q-, wherein M is a $C_{3-10}$ cycloalkyl optionally substituted with 1 or more $R^{19}$, and Q is a bond, or $C_{1-10}$ alkyl optionally substituted with 1 or more $R^{19}$;

$R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —$NO_2$, —$NR^{20}R^{21}$, $C_{1-18}$ haloalkyl, $C_{1-18}$ haloalkyloxy, —C(=O)$R^{18}$, —C(=O)O$R^{18}$, —Oalkenyl C(=O)O$R^{18}$, —Oalkyl C(=O)$NR^{20}R^{21}$, —OalkylOC(=O)$R^{18}$, —C(=S)$R^{18}$, SH, —C(=O)N($C_{1-6}$ alkyl), —N(H)S(O)(O)($C_{1-6}$ alkyl), aryl, heterocyclic, $C_{1-18}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio or aryl($C_{1-18}$)alkyl, where each may be optionally substituted with 1 or more =O, $NR^{20}R^{21}$, CN, $C_{1-18}$ alkoxy, heterocyclic, $C_{1-18}$ haloalkyl, heterocyclic alkyl, heterocyclic connected to $R^{17}$ by alkyl, alkoxyalkoxy or halogen;

$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)$R^{12}$, or —C(=S) $R^{12}$;

$R^{22}$ is selected from hydrogen, —OH, $C_{1-18}$ alkyl, $C_{2-18}$ alkenyl, $C_{1-18}$ alkoxy, —$NR^{23}R^{24}$, aryl, $C_{3-10}$ cycloalkyl, and $C_{4-10}$ cycloalkenyl;

$R^{23}$ and $R^{14}$ are independently selected from hydrogen, $C_{1-18}$ alkyl, or a heterocyclic formed by taking $C_{2-3}$ alkyl together with N of $R^{22}$, which heterocyclic is optionally substituted with OH or aryl, or an amino acid residue linked through a carboxyl group of the amino acid;

$R^{25}$ and $R^{26}$ are not present, or are independently selected from hydrogen, $C_{1-18}$ alkyl, $C_{3-10}$ cycloalkyl, aryl, heterocyclic, where each is optionally independently substituted with 1 to 4 of $C_{1-6}$ alkyl, $C_{1-6}$ alkoxy, halo, $CH_2OH$, benzyloxy, and OH; and $R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and aryl $C_{1-18}$ alkyl, and the salts, tautomers, isomers and solvates thereof.

Yet another embodiment of the present invention provides compounds having the formula (B),

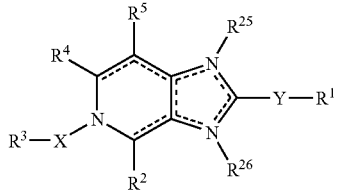
(B)

wherein:
the dotted lines represent an optional double bond, provided that no two double bonds are adjacent to one another, and that the dotted lines represent at least 3, optionally 4 double bonds; and $R^1$, $R^2$, $R^3$, $R^4$, $R^5$, $R^{25}$, $R^{26}$, X and Y are as disclosed above.

An embodiment of the present invention provides compounds of the formula (B) wherein Y is a single bond, and $R^1$ is aryl.

Another embodiment of the present invention provides compounds of formula (B) wherein X is $C_1$-$C_{10}$ alkylene, $C_{2-10}$ alkenylene or $C_{2-10}$ alkynylene.

Another embodiment of the present invention provides compounds of formula (B) wherein $R^3$ is heterocylic.

Another embodiment of the present invention provides compounds of formula (B) wherein $R^3$ is heterocyclic substituted with $R^{17}$ where Q is a bond and M is aryl.

Another embodiment of the present invention provides compounds of formula (B) wherein Y is a single bond, and $R^1$ is phenyl.

Another embodiment of the present invention provides compounds of formula (B) wherein $R^3$ is isoxazole substituted with $R^{17}$ where Q is a bond and M is aryl.

Another embodiment of the present invention provides compounds of formula (B) wherein $R^3$ is isoxazole substituted with $R^{17}$ where Q is a bond and M is phenyl.

Yet another embodiment of the present invention provides compounds having the formula (C),

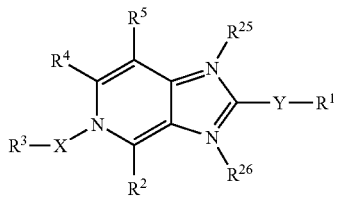
(C)

wherein $R^1$, $R^2$, $R^3$, $R^4$, $R^5$, $R^{25}$, $R^{26}$, X and Y are as disclosed above.

An embodiment of the present invention provides compounds of the formula (C) wherein Y is a single bond, and $R^1$ is aryl.

Another embodiment of the present invention provides compounds of formula (C) wherein X is $C_1$-$C_{10}$ alkylene, $C_{2-10}$ alkenylene or $C_{2-10}$ alkynylene.

Another embodiment of the present invention provides compounds of formula (C) wherein $R^3$ is heterocylic.

Another embodiment of the present invention provides compounds of formula (C) wherein $R^3$ is heterocyclic substituted with $R^{17}$ where Q is a bond and M is aryl.

Another embodiment of the present invention provides compounds of formula (C) wherein Y is a single bond, and $R^1$ is phenyl.

Another embodiment of the present invention provides compounds of formula (C) wherein $R^3$ is isoxazole substituted with $R^{17}$ where Q is a bond and M is aryl.

Another embodiment of the present invention provides compounds of formula (C) wherein $R^3$ is isoxazole substituted with $R^{17}$ where Q is a bond and M is phenyl.

The compounds of formula (A) are optionally combined with pharmacologically acceptable excipients.

The compounds of formula (A) are administered in therapeutically effective amounts to subjects (humans or animals) in need of antiviral therapy, in particular for inhibiting the infection, growth or replication of Flaviviridae and Picornaviridae, especially BVDV, HCV and Coxsackie virus.

The invention further relates to a method of screening antiviral compounds which comprises providing a compound of formula (A) and determining the anti-viral activity of said compound.

Also within the scope of the invention is a metabolite of the compounds of formula (A) made by the process of administering a compound of formula (A) to a subject and recovering the metabolite from the subject.

The invention also comprises a method for structure-activity determination of analogues of formula (A) compounds

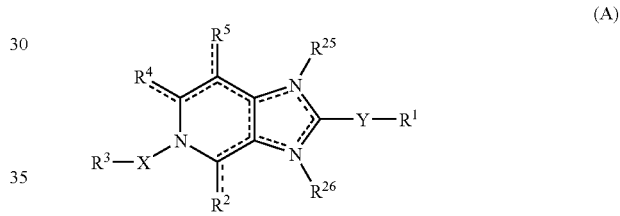
(A)

wherein the substituents are defined in WO 2004/005286, comprising
(A) preparing a compound of formula (A) in which at least one substituent is not disclosed by WO 2004/005286; and
(B) determining the anti-HCV activity of the compound of step (a).

DETAILED DESCRIPTION OF THE INVENTION

"Alkyl" means saturated hydrocarbon moiety where the moiety may be acyclic, cyclic or a combination of acyclic and cyclic portions. The acyclic portion may contain 1 to 3 carbon atoms, and each ring may contain 3 to 6 carbon atoms (for example, 3-methylcyclohexyl). Within this definition, the term "cycloalkyl" refers to the saturated hydrocarbon moieties that are cyclic. Examples of "alkyl" include methyl, ethyl, 1-propyl, 2-propyl, 1-butyl, 2-methyl-1-propyl (i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl, cyclopropyl, cyclobutyl, cyclopentyl, cycloheptyl, cyclooctyl and the like, or a $C_{7-10}$ polycyclic saturated hydrocarbon radical having from 7 to 10 carbon atoms such as, for instance, norbornyl, fenchyl, trimethyltricycloheptyl or adamantyl.

"Alkenyl" means a hydrocarbon moiety with at least one site of double bond unsaturation where the moiety may be acyclic, cyclic or a combination of acyclic and cyclic portions. The acyclic portion may contain 1 to 3 carbon atoms, and each cyclic portion may contain 3 to 6 carbon atoms. A site of double bond unsaturation may be in a acyclic portion, a cyclic portion. In the instance of a moiety having a combination of acyclic and cyclic portions, there may be a site of double bond unsaturation in each of the portions. Within this definition, the term "cycloalkenyl" refers to the double bond unsaturated hydrocarbon moieties that are cyclic. Examples the term "alkenyl" include, but are not limited to, ethylene or vinyl (—CH=$CH_2$), allyl (—$CH_2$CH=$CH_2$), cyclopentenyl (—$C_5H_7$), 5-hexenyl (—$CH_2CH_2CH_2CH_2$CH=$CH_2$), 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. The double bond optionally is in the cis or trans configuration.

"Alkynyl" means a hydrocarbon moiety with a least one site of triple bond unsaturation where the moiety may be acyclic, cyclic or a combination of acyclic and cyclic portions. The acyclic portion may contain 1 to 3 carbon atoms, and each cyclic portion may contain 7 or more carbon atoms. Within this definition, the term "cycloalkynl" refers to triple bond unsaturated hydrocarbon moieties that are cyclic. Examples of the term "alkynyl" include, but are not limited to, —C≡CH, —$CH_2$C≡CH, —$CH_2$C≡C-cyclohexyl, or —$CH_2$-cycloheptynyl.

The suffix "-ene" used in connection with alkyl, alkenyl and alkynyl groups refers to such groups with at least 2 sites of substitution. Such polyvalent hydrocarbon radicals include, but are not limited to, methylene (—$CH_2$—) 1,2-ethylene (—$CH_2CH_2$—), 1,3-propylene (—$CH_2CH_2CH_2$—), 1,4-butylene (—$CH_2CH_2CH_2CH_2$—), 1,2-ethylene (—CH=CH—), —C≡C—, propargyl (—$CH_2$C≡C—), and 4-pentynyl (—$CH_2CH_2CH_2$C≡CH—).

"Aryl" means an aromatic hydrocarbon containing 1 or more rings, generally 1, 2 or 3, with 4 to 6 carbon atoms in each, ordinarily 5 or 6 carbon atoms.

"Arylalkyl," "arylalkenyl" and "arylalkynyl" means an alkyl, alkenyl or alkynyl radical, respectively, in which one of the hydrogen atoms, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

As noted, carbocycles optionally are found as single rings or multiple ring systems. Ordinarily the hydrocarbons of the compounds of formula (A) are single rings. Monocyclic carbocycles generally have 3 to 6 ring atoms, still more typically 5 or 6 ring atoms. Bicyclic carbocycles typically have 7 to 12 ring atoms, e.g. arranged as a bicyclo [4,5], [5,5], [5,6] or [6,6] system, or 9 or 10 ring atoms arranged as a bicyclo [5,6] or [6,6] system.

If the number of carbon atoms is unspecified for a hydrocarbon, typically the number of carbon atoms will range from 1 to 18, except that the number of carbons typically will range from 2 to 18 for unsaturated hydrocarbons and from 6 to 10 for aryl.

"Heterocyclic" or "heterocycle" means any 4, 5, 6, 7, 8 or 9 membered single or fused ring system containing one or more heteroatoms selected from the group consisting of O, N or S. Heterocycles optionally are entirely aromatic, entirely saturated, or contain 1 or more intra-ring sites of unsaturation, typically double bonds. Multiple heterocyclic rings (one or more of which contains a heteroatom) are bridged or spiro. Generally, the heterocyclic rings will be aromatic, and usually they are single rings. Examples of heterocycles include oxazacyloalkyl, morpholinyl, dioxacycloalkyl, thiacycloalkenyl, pyridyl, dihydroypyridyl, tetrahydropyridyl (piperidyl), thiazolyl, tetrahydrothiophenyl, furanyl, thienyl, pyrrolyl, pyranyl, pyrazolyl, pyrazolidinyl, pyrazolinyl, imidazolyl, tetrazolyl, benzofuranyl, thianaphthalenyl, indolyl, indolenyl, quinolinyl, isoquinolinyl, benzimidazolyl, piperidinyl, piperazinyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isothiazoledinyl, isoxazolyl, oxazolinyl, pyrazinyl, pyridazinyl, pyrimidinyl, pyrrolidinyl, pyrrolinyl, indolizinyl, isoindolyl, 3H-indolyl, 1H-indazoly, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, oxazolidinyl, benzotriazolyl, benzisoxazolyl, oxindolyl, benzoxazolinyl, benzothienyl, benzothiazolyl and isatinoyl. Other suitable heterocycles are exemplified in Rigaudy et al., Nomenclature of Organic Chemistry, Sections A-H (1979) at pp. 53-76 and Fletcher et al., Nomenclature of Organic Compounds, Adv. Chem. Ser. 126 (1974) at pp 49-64.

The location on the heterocycle which provides the point of attachment(s) to the rest of the compound of this invention is not critical, but those skilled in the art will recognize substitution sites that are optimal for compound stability and/or ease of synthesis. Carbon bonded heterocycles typically are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

Nitrogen containing heterocycles are bonded at nitrogen or a carbon, typically a carbon atom. These include, for example, position 1 of aziridine, 1-aziridyl, 1-azetedyl, 1-pyrrolyl, 1-imidazolyl, 1-pyrazolyl, 1-piperidinyl, 2-pyrroline, 3-pyrroline, 2-imidazoline, 3-imidazoline, 9-carbazole, 4-morpholine, 9-alpha or β-carboline, 2-isoindole, 2-pyrazoline and 3-pyrazoline, and by analogy, azetidine, pyrrole, pyrrolidine piperidine, piperazine, indole, pyrazoline, indoline, imidazole, imidazolidine, 1H-indazole and isoindoline. These and other N-containing heterocycles are well-known to those skilled in the art, and their linkage sites are a matter of discretion.

Sulfur containing heterocycles are bonded through carbon or sulfur. They include oxidized states such as —S(=O)

(=O). In general, they are linked in the compounds of formula (A) analogous to N-containing heterocycles.

"Alkoxy", "cycloalkoxy", "aryloxy", "arylalkyloxy", "oxy heterocycle", "thioalkyl", "thiocycloalkyl", "arylthio", and "arylalkylthio" means substituents wherein an alkyl, cycloalkyl, aryl, or arylalkyl, respectively, are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

"Halogen" means any atom selected from the group consisting of fluorine, chlorine, bromine and iodine.

Any substituent designation that is found in more than one site in a compound of this invention shall be independently selected.

When a group is stated to be substituted with "one or more" of another group, this typically means 1 to 3 substituents, ordinarily 1, 2 or 3 substitutents.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

Amino Acids

"Amino-acid" refers to a radical derived from a molecule having the chemical formula $H_2N—CHR^{28}—COOH$, wherein $R^{28}$ is a side group of a naturally-occurring or known synthetic amino-acid. The amino acids optionally are substituted with hydrocarbon typically of 1 to 8 carbons at one or more carboxyl or amino groups, whether those groups are on the side chain or are free after linking the amino acid to the remainder of the compound of this invention.

Optionally the amino acid residue is a hydrophobic residue such as mono- or di-alkyl or aryl amino acids, cycloalkylamino acids and the like. Optionally, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included.

Generally, only one of any site in the parental molecule is substituted with an amino acid, although it is within the scope of this invention to introduce amino acids at more than one permitted site. In general, the α-amino or α-carboxyl group of the amino acid are bonded to the remainder of the molecule, i.e., carboxyl or amino groups in the amino acid side chains generally are not used to form the amide bonds with the parental compound (although these groups may need to be protected during synthesis of the conjugates).

The amino acid esters optionally are hydrolyzable in vivo or in vitro under acidic (pH<3) or basic (pH>10) conditions. Optionally, they are substantially stable in the gastrointestinal tract of humans but are hydrolyzed enzymatically in blood or in intracellular environments.

$R^{28}$ usually is $C_1$-$C_6$ alkyl or $C_1$-$C_6$ alkyl substituted with amino, carboxyl, amide, carboxyl (as well as esters, as noted above), hydroxyl, $C_6$-$C_7$ aryl, guanidinyl, imidazolyl, indolyl, sulfhydryl, sulfoxide, and/or alkylphosphate. $R^{28}$ also is nitrogen to form a proline residue taken together with the amino acid α-However, $R^{28}$ is generally the side group of the naturally-occurring amino acid disclosed above, for example H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—$C(NH_2)$—$NH_2$. $R^{28}$ also includes 1-guanidinoprop-3-yl, benzyl, 4-hydroxybenzyl, imidazol-4-yl, indol-3-yl, methoxyphenyl and ethoxyphenyl.

Exemplary Embodiments $R^1$ is generally aryl or aromatic heterocyle substituted with 1, 2 or 3 $R^6$ wherein $R^6$ is halogen, $C_{1-18}$ alkoxy; or $C_{1-18}$ haloalkyl. Typically, $R^1$ is phenyl substituted with 1, 2 or 3 halogens, usually fluoro.

Y generally is a single bond, O, $C_{1-6}$ alkylene, $C_{2-6}$ alkenylene, $C_{2-6}$ alkynylene or one of said groups containing 1 to 3, usually 1, heteroatoms selected from O, S or $NR^{11}$. Examples include —$O(CH_2)_{1-5}$—, —$(CH_2)_{1-4}$—O—$(CH_2)_{1-4}$—, —S—$(CH_2)_{1-5}$—, —$(CH_2)_{1-4}$—S—$(CH_2)_{1-4}$—, —$NR^{11}$—$(CH_2)_{1-5}$—, —$(CH_2)_{1-4}$—$NR^{11}$—$(CH_2)_{1-4}$ or $C_{3-10}$ cycloalkylidene. Typically, Y is —$OCH_2$—, —$CH_2O$—, $C_{1-2}$ alkylene, $C_{2-3}$ alkenylene, $C_{2-3}$ alkynylene, O or a bond, but usually a bond.

In general, $YR^1$ is not any one of H, an unsubstituted $C_{3-10}$ cycloalkyl or C1-C6 alkyl. Typically $YR^1$ is halo or halomethyl-substituted (typically trihalomethyl)phenyl (and usually 1 to 2 substituents in ortho or meta).

X usually is alkylene, alkynylene or alkenylene, typically alkylene, or said hydrocarbons having an intrachain heteroatom, typically O or S. Examples include —$CH_2$—, —CH($CH_3$)—, —$CH_2$—$CH_2$—, —$CH_2$—$CH_2$—$CH_2$—, —$CH_2$—$CH_2$—$CH_2$—$CH_2$, —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —CH=CH—$CH_2$—) and $C_{2-6}$ alkynylene. Usually, X is methylene.

$R^3$ generally is aryl or a heterocycle, typically an aromatic heterocycle. The heterocycle generally will contain 1, 2 or 3 N, S or O atoms in the ring, usually is linked to X through a ring carbon atom and typically contains 4 to 6, usually 5, total ring atoms. The $R^3$ aryl or heterocycle ordinarily is substituted with 1, 2 or 3, usually 1, $R^{17}$. $R^3$ optionally is not indolyl.

When $R^3$ is substituted with $R^{17}$ then $R^{17}$ typically is aryl or a heterocycle further substituted with 1 or more, usually 1, 2 or 3, $R^{19}$.

$R^{17}$ is M-Q in some embodiments of the invention. M is a ring. This means any cyclic organic structure, whether carbocyclic or heterocyclic, and whether saturated, unsaturated or aromatic or single or fused ring systems. M is chosen from rings that are structurally stable in biological systems. In general, M is a aryl or aromatic heterocycle where heterocycle is defined above.

Q is a spacer group, and is not critical. Typically it is not cyclic and contains from no to 3 atoms, generally C, O or S, usually C or O.

$R^{17}$ typically is selected from the group consisting of $C_{3-10}$ cycloalkyl, $C_{3-10}$ cycloalkenyl, $C_{7-10}$ cycloalkynyl, halogen, aryl, aryloxy, arylthio, arylsulfoxide, arylsulfone, arylsulfonamide, arylalkyl; arylalkyloxy (optionally an benzyloxy); arylalkylthio (optionally a benzylthio); a heterocycle; $C_{1-18}$ hydroxyalkyl, but typically is an aryl or a heterocycle, and where each of said aryl, aryloxy, arylthio, arylsulfoxide, arylsulfone, arylsulfonamide, arylalkyl, arylalkyloxy, arylalkylthio, or heterocycle is optionally substituted with 1 or more $R^{19}$. $R^{17}$ generally is positioned distally to X. Optionally, $R^{17}$ is not $C(O)R^{18}$.

$R^9$ and $R^{18}$ typically are H, OH or alkyl. $R^{18}$ optionally is not $NR^{15}R^{16}$.

$R^5$ typically is H.

$R^6$ generally is halogen. Optionally, $R^6$ is not $C(O)R^{18}$.

$R^7$, $R^8$, $R^{10}$, $R^{11}$, $R^{13}$, $R^{14}$, $R^{15}$, $R^{16}$, $R^{20}$, $R^{21}$, $R^{23}$ and $R^{24}$ typically are independently H or $C_{1-18}$ alkyl.

$R^{12}$ and $R^{22}$ typically are independently OH or alkyl.

$R^{19}$ usually is H; $C_{1-18}$ alkyl; $C_{2-18}$ alkenyl; $C_{2-18}$ alkynyl; $C_{1-18}$ alkoxy; alkenyloxy; alkynyloxy; $C_{1-18}$ alkylthio; $C_{3-10}$ cycloalkyl; $C_{4-10}$ cycloalkenyl; $C_{4-10}$ cycloalkynyl; halogen; OH; CN; cyanoalkyl; $NO_2$; $NR^{20}R^{21}$; haloalkyl; haloalkyloxy; $C(=O)R^{18}$; $C(=O)OR^{18}$; $OalkenylC(=O)OR^{18}$; $-OalkylC(=O)NR^{20}R^{21}$; aryl; heterocycle; $-OalkylOC(=O)R^{18}$; $C(=O)N(C_{1-6}$ alkyl), $N(H)S(O)(O)(C_{1-6}$ alkyl); arylalkyloxy; aryloxy; arylalkyloxy; and arylalkyl; each of which is unsubstituted or substituted with 1 or more =O; $NR^{20}R^{21}$; CN; alkoxy; heterocycle; haloalkyl- or alkyl-substituted heterocycle; heterocycle linked to $R^{17}$ by alkyl; alkoxyalkoxy or halogen. $R^{18}$ as a substituent in here is generally not H. $R^{19}$ typically is independently halogen, $N(R^{20}R^{21})$, alkoxy or halo-substituted alkyl or alkoxy.

$R^{25}$ and $R^{26}$ usually are not present but if they are then typically they are cyclopentyl or cyclohexyl. If the compound is substituted at $R^{25}$ or $R^{26}$, either $R^2$ or $R^4$ is selected from $(=O)$, $(=S)$, and $(=NR^{27})$, usually =O.

M typically is an aromatic ring, usually single or two fused rings, and containing 4 to 10 atoms. Usually, M is hydrocarbon, but also optionally comprises 1 to 3 N, O and/or S heteroatoms.

Q usually is a hydrocarbon chain, typically a normal or secondary alkylene, which optionally comprises at least one oxy or thio ester. Generally Q is 1 to 6 atoms, usually 1 to 3. Q typically is not substituted with $R^{19}$, but if it is then typically it is substituted with one $R^{19}$. $R^{19}$ as substituted on Q usually is halogen, nitro or cyano. Substituents optionally are designated with or without bonds. Regardless of bond indications, if a substituent is polyvalent (based on its position in the structure referred to), then any and all possible orientations of the substituent are intended.

Haloalkyl or haloalkyloxy typically are —CF3 or —OCF3.

The present invention provides a compound of Formula (A) of the following the structure, having antiviral activity as determined following the procedures taught throughout the Specification, such as in Part B "Methodology For Determination Of Antiviral And Cytostatic Activity" in the Examples Section. Preparation of this compound is taught throughout the Specification, such as in Example 6.

The present invention further provides a compound of Formula (A) of the following structure,

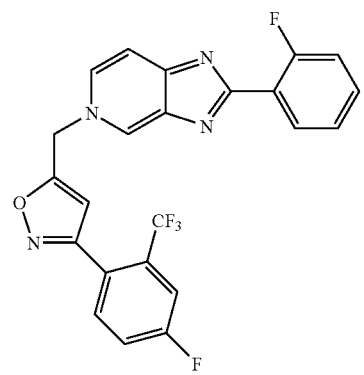

having antiviral activity as determined following the procedures taught throughout the Specification, such as in Part B "Methodology For Determination Of Antiviral And Cytostatic Activity" in the Examples Section. Preparation of this compound is taught throughout the Specification, such as in Example 8A.

Formula (A) depicts optional single or double bonds. It will be understood that the bonds are present such that the aromatic nature of the nucleus of formula (A) is preserved, i.e., these formulas are intended to embrace all possible tautomers. For example $R^{25}$ or $R^{26}$ will be absent if the ring N to which they are bonded as indicated in the formula is linked to a flanking ring carbon atom by a double bond. On the other hand, $R^{25}$ or $R^{26}$ may be present when the N atom to which it is bonded as indicated in the formula is linked to its flanking carbon atoms by single bonds only; in this case aromaticity is accommodated by other substituents, e.g. where $R^2$ or $R^4$ is oxo.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

Prodrugs

Certain of the compounds herein when substituted with appropriate selected functionalities are capable of acting as prodrugs. These are labile functional groups which separate from an active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). These prodrug moieties can serve to enhance solubility, absorption and lipophilicity to optimize drug delivery, bioavailability and efficacy. A "prodrug" is thus a covalently modified analog of a therapeutically-active compound. A prodrug moiety of course can be therapeutically active in its own right.

Exemplary prodrug moieties include the hydrolytically sensitive or labile esters (—CO$_2$R') of carboxylic acids (—CO$_2$H) or other functional groups with an acidic proton which is bound to the imidazo[4,5-c]pyridine compounds of the invention. The R' group of such hydrolytically sensitive or labile esters may include: (i) acyloxymethyl esters —CH$_2$C(=O)R$^{9a}$; and (ii) acyloxymethyl carbonates —CH$_2$C(=O)OR$^{9a}$ where R$^{9a}$ is C$_1$-C$_6$ alkyl, C$_1$-C$_6$ substituted alkyl, C$_6$-C$_{20}$ aryl or C$_6$-C$_{20}$ substituted aryl. A close variant of the acyloxyalkyl ester, the alkoxycarbonyloxyalkyl ester (carbonate), may also enhance oral bioavailability as a prodrug moiety in the compounds of the invention. An exemplary acyloxymethyl ester R group is pivaloyloxymethoxy, (POM) —CH$_2$C(=O)C(CH$_3$)$_3$. An exemplary acyloxymethyl carbonate prodrug moiety is pivaloyloxymethylcarbonate (POC) —CH$_2$OC(=O)OC(CH$_3$)$_3$. Cleavable moieties capable of acting as prodrug functionalities are optionally linked at any tolerant site on the compound of this invention, for example R$^3$ and any of its substituents.

Excluded Compounds

The present invention excludes all compounds expressly disclosed in any prior art reference (to the extent the reference is effective as novelty- or inventive step/obviousness-defeating as the case may be) set forth in this application (as well as any compounds disclosed in any reference patent family member) and any other compounds over which the claims of this application are not novel or do not posses an inventive step or are obvious under applicable law.

The present invention excludes, as required, compounds according to the general formula (A) where (a) Any of the substituents X, Y, R$^1$, R$^2$, R$^3$, R$^4$, R$^5$ are a cephalosporin or wherein the substituents X, Y, R$^1$, R$^2$, R$^3$, R$^4$, R$^5$ are an azabicyclo group, more particularly 5-Thia-1-aza-bicyclo[4.2.0]oct-2-en-8-one;

(b) The compound is 5-(2-piperidin-1-yl-ethyl)-2-(4-hydroxyphenyl)-1H-imidazo[4,5-c]pyridin-5-ium bromide (X=ethyl, Y=bond, R$^1$=phenyl substituted in para with OH, R$^2$=H, R$^3$=piperidinyl, and R$^4$, R$^5$=H) (as disclosed in example 52 of EP 1132381);

(c) The compound is 4-[5-(2-{4-[Bis-(4-fluorophenyl)-methyl]-piperazin-1-yl}-ethyl)-5H-imidazo[4,5-c]pyridin-2-yl]phenol (X=ethyl, Y=bond, R$^1$=phenyl substituted in para with OH, R$^2$=H, R$^3$=heterocycle with 2 N heteroatoms, wherein one N is substituted with an arylalkyl consisting of CH(Phenyl)$_2$, wherein each phenyl carries an F in para) (as disclosed in example 54 of EP 1132381);

(d) The compound is 4-[5-(3-{4-[Bis-(4-fluorophenyl)-methyl]-piperazin-1-yl}-propyl)5H-imidazo[4,5-c]pyridin-2-yl]phenol (X=butyl, Y=bond, R$^1$=phenyl substituted in para with OH, R$^2$=H, R$^3$=heterocycle with 2 N heteroatoms, wherein one N is substituted with an arylalkyl consisting of CH(Phenyl)$_2$, wherein each phenyl carries an F in para) (as disclosed in example 55 of EP 1132381);

(e) The compound is 5-(phenylmethyl)-5H-imidazo[4,5-c]pyridine wherein phenyl is substituted with CONR$^{15}$R$^{16}$ and R$^{15}$ is a branched C3 alkyl and R$^{16}$ is phenyl (X=—CH$_2$—; Y=bond; R$^1$=hydrogen; R$^2$=H; R$^3$=phenyl substituted with 1 C(=O)R$^{18}$, wherein R$^{18}$ is NR$^{15}$R$^{16}$, with R$^{15}$ and R$^{16}$ a branched C$_6$ alkyl; R$^4$=H) (as disclosed in example 35 of U.S. Pat. No. 5,302,601);

(f) The compound is 6-(5H-imidazo[4,5-c]pyridin-5-ylmethyl)-N-(1methylethyl)-N-phenyl-3-pyridinecarboxamide (X=—CH$_2$—; Y=bond; R$^1$=hydrogen; R$^2$=H, R$^3$=pyridine substituted with 1 R$^6$, wherein R$^6$=1 C=O R$^{18}$, wherein R$^{18}$ is NR$^{15}$R$^{16}$, wherein R$^{15}$=isopropyl and R$^{16}$=phenyl) (as disclosed in example 6 of U.S. Pat. No. 4,990,518);

(g) The compound is a compound wherein X=—CH$^2$—; Y=bond; R$^1$=hydrogen; R$^2$=H, R$^3$=5-6 membered heterocycle, in particular a pyridinyl or furanyl, substituted with 1 R$^{17}$ wherein R$^{17}$=C(=O)R$^{18}$, and wherein R$^{18}$=NR$^{15}$R$^{16}$ and R$^{15}$ and R$^{16}$ are either a C$_{1-18}$ alkyl, in particular methyl, ethyl or isopropyl, C$_{2-18}$ alkenyl, in particular 2-methyl allyl, or a C$_{3-10}$ cycloalkyl, in particular cyclopentyl or cyclohexyl (as disclosed in U.S. Pat. No. 4,990,518);

(h) The compound is a compound wherein X=—CH$^2$—; Y=bond; R$^1$=hydrogen; R$^2$=H, R$^3$=5-6 membered heterocycle, in particular a pyridinyl or furanyl, substituted with 1 R$^{17}$ wherein R$^{17}$=C(=O)R$^{18}$, and wherein R$^{18}$=C$_{3-10}$ cycloalkyl or C$_{4-10}$ cycloalkenyl.

(i) The compound is 2,6-bis(1,1,-dimethylethyl)-4-[[2-(5H-imidazo-[4,5-c]pyridin-5-yl)ethyl]thio]-phenol hydrate and/or 2,6-bis(1,1,-dimethylethyl)-4-[[2-(5H-imidazo-[4,5-c]pyridin-5-yl)propyl]thio]-phenol hydrate (X=CH$^2$—CH$^2$—; Y=bond; R$^1$=hydrogen, R$^2$=H, R$^3$=thioaryl substituted with three R$^6$, wherein R$^6$=2 branched C$_4$alkyl in meta and OH in para) (as disclosed in example 6 of WO96/12703);

(j) The compound is 5-[2-(Biphenyl-4-yloxy)-ethyl]-5H-imidazo[4,5-c]pyridine (X=CH$_2$CH$_2$, Y=bond, R$^1$=hydrogen, R$^2$=H, R$^3$=phenoxy substituted with 1 R$^{17}$ in para, wherein R$^{17}$=benzyl; R$^4$=H) (as disclosed in WO96/11192);

(k) The compound is 5-[2-(4-Phenoxy-phenoxy)-ethyl]-5H-imidazo[4,5-c]pyridine (X=CH$_2$CH$_2$, Y=bond, R$^1$=hydrogen, R$^2$=H, R$^3$=phenoxy substituted with 1 R$^{17}$ in para, wherein R$^{17}$=phenoxy; R$^4$=H) (as disclosed in WO96/11192);

(l) The compound is [5-(4-Fluorobenzyl)-5H-imidazo[4,5-c]pyridin-2-yl]-methylamine (X=CH$_2$, Y=NR$^{11}$, wherein R$^{11}$=methyl, R$^1$=R$^2$=H, R$^3$=phenyl substituted with 1 R$^{17}$ in para, wherein R$^6$ is F, R$^4$=H, R$^5$=H) (as disclosed in EP76530);

(m) The compound is 2,6-bis(1,1,-dimethylethyl)-4-[[3-(5H-imidazo-[4,5-c]pyridin-5-yl)propyl]thio]-phenol hydrate (X=CH$_2$—CH$_2$—CH$_2$—, Y=bond; R$^1$=hydrogen, R$^2$=H, R$^3$=thiophenyl substituted with 3 R$^6$, wherein R$^6$=2 branched C4 alkyl in meta and OH in para) (as disclosed in WO96/12703);

(n) The compound is 5-[2-(4-Phenylmethyloxy-phenoxy)-ethyl]-5H-imidazo[4,5-c]pyridine (X=CH$_2$CH$_2$, Y=bond, R$^1$=hydrogen, R$^2$=H, R$^3$=phenoxy substituted with 1 R$^{17}$ in para, wherein R$^{17}$=benzyl oxy) (as disclosed in WO96/11192);

(o) The compound is 5-[3-(4-Phenoxy-phenoxy)-propyl]-5H-imidazo[4,5-c]pyridine (X=CH$_2$CH$_2$CH$_2$, Y=bond, R$^1$=hydrogen, R$^2$=H, R$^3$=phenoxy substituted with 1 R$^6$ in para, wherein R$^6$=phenoxy substituted in para with F; R$^4$=H) (as disclosed in WO96/11192);

(p) The compound is 5-{2-[4-(4-Fluorophenoxy)-phenoxy]-ethyl}-5H-imidazo[4,5-c]pyridine (X=CH$_2$CH$_2$, Y=bond, R$^1$=hydrogen, R$^2$=H, R$^3$=phenoxy substituted with 1 R$^6$ in para, wherein R$^6$=phenoxy, substituted in para with F; R$^4$=H) (as disclosed in WO96/11192);

(q) The compound is 5-[3-(4-Phenylmethyl-phenoxy)-propyl]-5H-imidazo[4,5-c]pyridine (X=CH$_2$CH$_2$CH$_2$, Y=bond, R$^1$=hydrogen, R$^2$=H, R$^3$=phenoxy substituted with 1 R$^6$ in para, wherein R$^6$=benzyl; R$^4$=H) (as disclosed in WO96/11192);

(r) The compound is (1H-Indol-3-yl)-[3-(2-methyl-5H-imidazo[4,5-c]pyridine-5-carbonyl)-phenyl]-methanone (X=—(C=O)— or SO$_2$, Y=CH$_2$, R$^1$=H, R$^2$=H, R$^3$=phenyl substituted with 1 R$^6$, wherein R$^6$ is C(=O)R$^{18}$, wherein R$^{18}$ is indole) (as disclosed in U.S. Pat. No. 5,486,525);

(s) The compound is 4 or 3-[(2-methyl-5H-imidazo[4,5-c]pyridin-5-yl)methyl]-benzoic acid alkylester or 5-[4 or 3-(alkoxycarbonyl-phenyl)-methyl]-2-methyl-5H-imidazo[4,5-c]pyridine, in particular 4 or 3-[(2-methyl-5H-imidazo[4,5-c]pyridin-5-yl)methyl]-methyl ester (X=CH$_2$, Y=CH$_2$, R$^1$=H, R$^2$=H, R$^3$=phenyl substituted at the para or meta position with one R$^{17}$, wherein R$^{17}$ is (C=O)R$^{18}$, wherein R$^{18}$=alkoxy) (as disclosed in U.S. Pat. No. 5,486,525)

(t) The compound is 5-[(fluorophenyl)methyl]-2-amino-5-H-imidazo[4,5-c]-pyridine (XR$^3$=fluorobenzyl, Y=NR$^{11}$ with R$^{11}$=methyl, R$^1$=H, R$^2$, R$^3$, R$^4$=H) (as disclosed in U.S. Pat. No. 5,137,896);

(u) The compound is ((5-[4-(Fluorophenyl)methyl]-5-H-imidazo[4,5-c]-pyridine-2-yl)methyl)-carbamate, methyl ester (XR$^3$=fluorobenzyl, Y=C(=O)R$^{12}$ with R$^{12}$=methyl, R$^1$=H, R$^2$, R$^3$, R$^4$=H) (as disclosed in U.S. Pat. No. 5,137,896);

(v) The compound is 5-(4-Chlorophenylmethyl)-2-(piperidin-1-ylmethyl)-5H-imidazo[4,5-c]pyridine and its dihydrochloride salt (XR$^3$=chlorobenzyl, Y=—CH$_2$—, R$^1$=piperidinyl) (as disclosed in Justus Liebigs Annalen der Chemie (1971), 747, 158-171);

(w) The compound is 5-(4-Chlorophenylmethyl)-2-(4-methyl-piperazin-1-ylmethyl)-5H-imidazo[4,5-c]pyridine (XR$^3$=chlorobenzyl, Y=—CH$_2$—, R$^1$=piperazinyl, R$^6$=methyl) (as disclosed in Journal of the Chemical Society [section B]: Physical Organic (1966), 4, 285-291);

(x) Compounds, particularly compound 9 on page 160, Cleve et al. "Liebigs Ann. Chem. 747:158-171 (1971);

(y) Compounds, particularly compounds 19 and 20, of Kiyama et al. "Chem. Pharm. Bull. 43(3):450-460 (1995); and (z) Compounds, particularly compound 14, of Medereski et al. "Tet. Lt."48(48):10549-10558 (1992)

The compounds of the invention optionally exclude those compounds according to the general formula (A) as described above, wherein (a) YR$^1$ is not phenyl para substituted with OH, or (b) is H, an unsubstituted C$_{3-10}$ cycloalkyl, or C$_{1-6}$ alkyl.

The compounds of the invention optionally exclude those compounds according to the general formula (A) as described above, wherein R$^1$ is not H, Y is not NR$^{11}$ with R$^{11}$ C$_{1-6}$ alkyl or methyl, and/or YR$^1$ is not monomethylamino.

The compounds of the invention optionally exclude those compounds according to the general formula (A) as described above, wherein R$^1$ is a phenyl substituted with 1R$^6$, R$^6$ is C(=O)R$^{18}$ and R$^{18}$ is t-butoxy.

The compounds of the invention optionally exclude those compounds according to the general formula (A) as described above, wherein R$^1$ is not piperidinyl and is not piperazinyl substituted with methyl.

The compounds of this invention exclude those compounds disclosed by WO 2004/005286, in particular the compounds in table 8 thereof.

The compounds of this invention Optionally exclude those in which XR$^3$ is the definitional equivalent to the substructure —(CH$_2$)n-Y—C(O)—N(R1)(R2) set forth on column 1, line 49 to column 2 line 38 of U.S. Pat. No. 5,302,601 and the comparable disclosure in any member of the patent family of U.S. Pat. No. 5,302,601, which disclosure is herewith expressly incorporated by reference.

The compounds of this invention optionally exclude those in which R$^5$ contains any of the substituents designated as <<Ar>> in WO 00/39127, in particular aryl, aryl phenoxy, or benzyl.

The compounds of this invention optionally do not include the compounds of Example 35 of U.S. Pat. No. 5,302,601, Example 6 of U.S. Pat. No. 4,990,518, Examples 1 to 5 of U.S. Pat. No. 4,988,707, Examples 1-5 of U.S. Pat. No. 5,208,241, Example 39 of U.S. Pat. No. 5,137,896, the azabenzimidazole compound of WO 99/27929, Examples 1-20 and 45 of U.S. Pat. No. 5,227,384, Examples 3 and/or 11 of WO 96/12703 and/or compounds 340A, 347C, 349C, 351C, 355C and/or 356 C of WO 96/11192.

The compounds of this invention optionally exclude those in which XR$^3$ is equivalent to the substructure —(CH$_2$)n-Het-C(O)—N(R$^1$)(R$^2$) set forth on column 1, line 41 to column 2 line 24 of U.S. Pat. No. 4,990,518.

The compounds of this invention do not include the compounds expressly disclosed in the patents listed in the Background of the Invention above, in Chemical Abstracts acc no. 1987:18435 and in Chemical Abstracts acc no. 1983:594812.

The compounds of this invention do not include the compounds expressly disclosed in Justus Liebigs Annalen der Chemie (1971), 747, 158-171 or in the Journal of the Chemical Society [section B]: Physical Organic (1966), 4, 285-291.

Optionally, the compounds of this invention exclude those compounds wherein YR$^1$ is one of the substituents designated R$^{13}$ in column 5, lines 22-38 of U.S. Pat. No. 5,486,525 and/or R$^2$ and/or R$^5$ are one of the substituents collectively designated R$^{14}$ and R$^{15}$ in column 5, lines 38-53 of U.S. Pat. No. 5,486,525.

Optionally, the compounds of this invention exclude the compounds found in any patent family member of any published or issued patent specifically recited in this application.

Finally, the compounds of this invention optionally also exclude the methylene homologues of the foregoing known compounds excluded from the scope of this invention. It is understood that a compound optionally excluded also includes the salts thereof.

Utilities

The compounds of this invention, or the metabolites produced from these compounds in vivo, have a large number of uses. They are useful in immunology, chromatography, diagnostics and therapeutics, among other fields.

The compounds of formula (A) are conjugated to immunogenic polypeptides as a reagent for eliciting antibodies capable of binding specifically to the polypeptide, to the compounds or to their metabolic products which retain immunologically recognized epitopes (sites of antibody binding). These immunogenic compositions therefore are useful as intermediates in the preparation of antibodies for use in diagnostics, quality control, or the like, or in assays for the compounds of formula (A) or their novel metabolic products. The compounds are useful for raising antibodies against otherwise non-immunogenic polypeptides, in that the compounds serve as haptenic sites stimulating an immune response which cross-reacts with the unmodified conjugated protein.

Conjugates of the compounds of formula (A) with immunogenic polypeptides such as albumin or keyhole limpet hemocyanin generally are useful as immunogens. The polypeptides are conjugated at the same sites denoted for amino acids. The metabolic products described above may retain a substantial degree of immunological cross reactivity with the compounds of the invention. Thus, the antibodies of this invention will be capable of binding to the unprotected compounds of the invention without binding to the protected compounds. Alternatively the metabolic products will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1-100, typically, 1-25, more typically 1-10 carbon atoms to the immunogenic substance. The conjugates are separated from starting materials and by products using chromatography or the like, and then are sterile filtered and vialed for storage.

Animals are typically immunized against the immunogenic conjugates or derivatives and antisera or monoclonal antibodies prepared in conventional fashion.

The compounds of this invention are useful as linkers, spacers or affinity (typically hydrophobic) moieties in preparing affinity absorption matrices. The compounds of the invention optionally are bound covalently to an insoluble matrix and used for affinity chromatography separations, depending on the nature of the groups of the compounds, for example compounds with pendant aryl groups are useful in making hydrophobic affinity columns.

They also are useful as linkers and spacers in preparing immobilized enzymes for process control, or in making immunoassay reagents. The compounds herein contain functional groups that are suitable as sites for cross-linking desired substances. For example, it is conventional to link affinity reagents such as hormones, peptides, antibodies, drugs, and the like to insoluble substrates. These insolubilized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

The compounds of this invention are labeled with detectable moieties such biotin, radioisotopes, enzymes and the like for diagnostic purposes. Suitable techniques for accomplishing the labeling of the compounds of formula (A) are well known and will be apparent to the artisan from consideration of this specification as a whole. For example, one suitable site for labeling is R17 or R19.

More typically, however, the compounds of the invention are employed for the treatment or prophylaxis of viral infections such as yellow fever virus, Dengue virus, hepatitis B virus, hepatitis G virus, Classical Swine Fever virus or the Border Disease Virus, but more particularly flaviviral or picornaviral infections, in particular, HCV and BVDV.

The therapeutic compound(s) of this invention are administered to a subject mammal (including a human) by any means well known in the art, i.e. orally, intranasally, subcutaneously, intramuscularly, intradermally, intravenously, intra-arterially, parenterally or by catheterization. The therapeutically effective amount of the compound(s) is a flaviviral or picornaviral growth inhibiting amount. More preferably, it is a flaviviral or picornaviral replication inhibiting amount or a flaviviral or picornaviral enzyme inhibiting amount of the compounds of formula (A). This is believed to correspond to an amount which ensures a plasma level of between about 1 μg/ml and 100 mg/ml, optionally of 10 mg/ml. This optionally is achieved by administration of a dosage of in the range of 0.001 mg to 60 mg, preferably 0.01 mg to 10 mg, preferably 0.1 mg to 1 mg per day per kg bodyweight for humans. These are starting points for determining the optimal dosage of the compound of this invention. The actual amount will depend upon many factors known to the artisan, including bioavailability of the compound, whether it contains a prodrug functionality, its metabolism and distribution in the subject and its potency, among others. It typically is necessary to determine the proper dosing in the clinical setting, and this is well within the skill of the ordinary artisan. The therapeutically effective amount of the compound(s) of this invention optionally are divided into several sub-units per day or are administered at daily or more than one day intervals, depending upon the pathologic condition to be treated, the patient's condition and the nature of the compound of this invention.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27 or tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration.

Suitable anti-viral agents for inclusion in combination antiviral compositions or for coadministration in a course of therapy include, for instance, interferon alpha, ribavirin, a compound falling within the scope of disclosure of EP 1162196, WO 03/010141, WO 03/007945 and WO 03/010140, a compound falling within the scope of disclosure of WO 00/204425, and other patents or patent applications within their patent families, in amounts of 1 to 99.9% by weight compound of this invention, preferably from 1 to 99% by weight, more preferably from 5 to 95% by weight as can be readily determined by one skilled in the art. Such co-administered agents need not be formulated in the same dosage form as the compound of the invention. They optionally are simply administered to the subject in the course of treatment along with a course of treatment with a compound of formula (A).

The present invention further provides veterinary compositions comprising at least one active ingredient as above defined together with a veterinary carrier therefore, for example in the treatment of BVDV. Veterinary carriers are materials useful for the purpose of administering the composition and are excipients which are otherwise inert or acceptable in the veterinary art and are compatible with the compound of this invention. These veterinary compositions may be administered orally, parenterally or by any other desired route.

Salts

The term "pharmaceutically acceptable salts" as used herein means the therapeutically active non-toxic salt forms formed by the compounds of formula (A). Such salts may include those derived by combination of appropriate cations such as alkali and alkaline earth metal ions or ammonium and quaternary amino ions with an acid anion moiety, typically a carboxylic acid.

The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing Li+, Na+, Ca+2 and Mg+2 and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, benzoic, 2-hydroxypropanoic, 2-oxopropanoic, lactic, fumaric, tartaric, pyruvic, maleic, malonic, malic, salicylic (i.e. 2-hydroxybenzoic), p-aminosalicylic, isethionic, lactobionic, succinic oxalic and citric acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids, C1-C6 alkylsulfonic, benzenesulfonic, p-toluenesulfonic, cyclohexanesulfamic, and the like. Preferred salts include mesylate and HCl.

The compounds of this invention include the solvates formed with the compounds of formula (A) and their salts, such as for example hydrates, alcoholates and the like. The compositions herein comprise compounds of the invention in their un-ionized, as well as zwitterionic form, and combinations with stoichiometric amounts of water as in hydrates.

Also included within the scope of this invention are the salts of the compounds of formula (A) with one or more amino acids as described above. The amino acid typically is one bearing a side chain with a basic or acidic group, e.g., lysine, arginine or glutamic acid, or a neutral group such as glycine, serine, threonine, alanine, isoleucine, or leucine.

Salts of acids or bases which are not physiologically acceptable may also find use, for example, in the preparation or purification of a compound of formula (A). All salts, whether or not derived form a physiologically acceptable acid or base, are within the scope of the present invention.

Isomers

The term "isomers" as used herein means all possible isomeric forms, including tautomeric and stereochemical forms, which the compounds of formula (A) may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formula (A) may have one or more chiral centers), as well as the stereochemically pure or enriched isomers. More particularly, stereogenic centers may have either the R- or S-configuration, and double or triple bonds optionally are in either the cis- or trans-configuration.

Enriched isomeric forms of a compound of this invention are defined as a single isomer substantially free of the compound's other enantiomers or diastereomers. In particular, the term "stereoisomerically enriched" or "chirally enriched" relates to compounds having a single stereoisomeric proportion of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" contain undetectable levels of any other isomer.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing an acidic functionality, such as carboxylic acid and sulfonic acid.

The diastereomeric salts optionally are induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994). Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990). "Optical resolution of dihydropyridine enantiomers by High-performance liquid chromatography using phenylcarbamates of polysaccharides as a chiral stationary phase", J. of Chromatogr. 513:375-378).

Metabolites

The present invention also provides the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. C14 or H3) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no antiviral activity of their own.

Formulations

The compounds of the invention optionally are formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer.

It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Synthetic Methods

The compounds of formula (A) are prepared using a series of chemical reactions well known to those skilled in the art, altogether making up the process for preparing said compounds and exemplified further. The processes described further are only meant as examples and by no means are meant to limit the scope of the present invention.

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

Exemplary methods for the preparation of the compositions of the invention are provided below. These methods are intended to illustrate the nature of such preparations, and are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

General aspects of these exemplary methods are described below. Each of the products of the following processes is optionally separated, isolated, and/or purified prior to its use in subsequent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modification of the exemplified schemes and examples leads to various analogs of the specific exemplary materials produced above. The above citations describing suitable methods of organic synthesis are applicable to such modifications.

In the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Suitable methods for making the compounds of this invention also are found in WO 2004/005286, in particular schemes 1-13 therein.

Another synthetic route to 5-benzyl-2-phenyl-5H-imidazo[4,5-c]pyridine and analogues is shown in scheme 1.

Scheme 1:

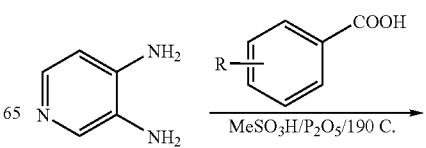

-continued
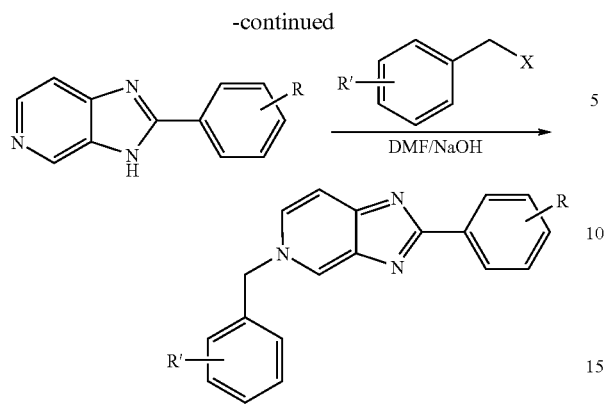
The following list includes carboxylic acid reactants which may be employed in the condensation, ring closure reaction of Scheme 1. The compounds so produced will bear the residue of the acid at the site of $YR^1$. Optionally, the remainder of the molecule will be as in any of the compounds of examples 2-7.
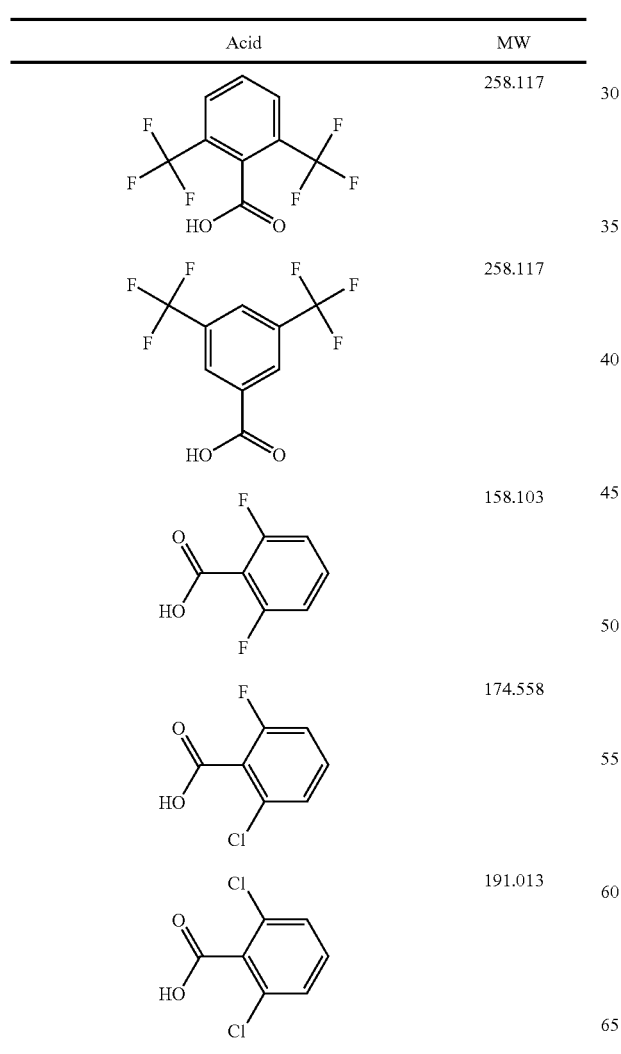
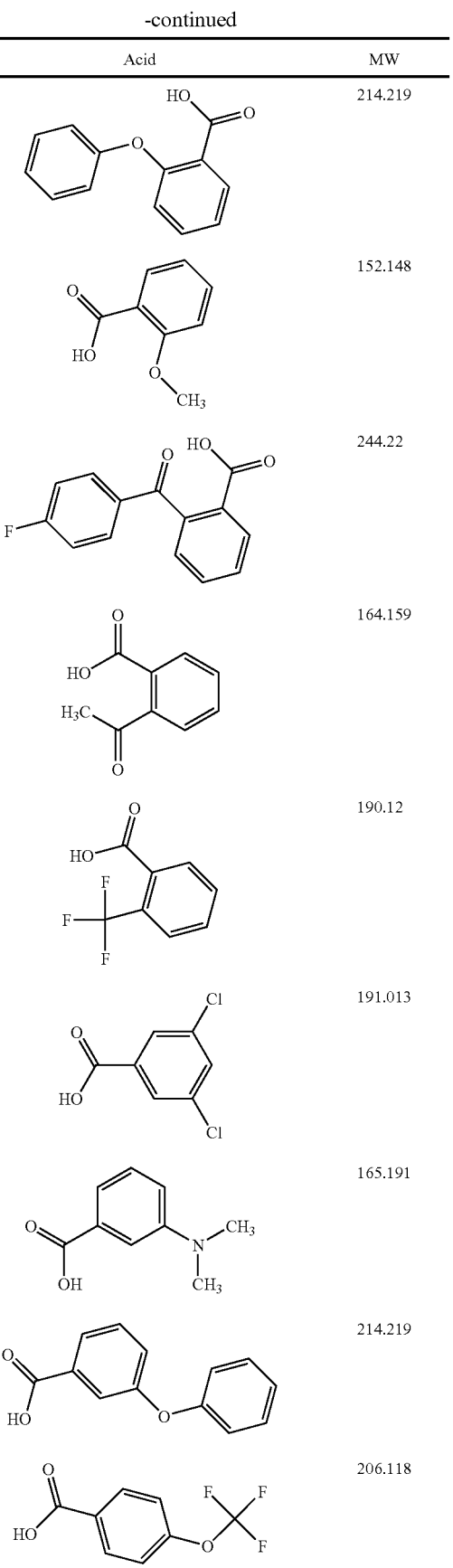

| Acid | MW |
|---|---|
| 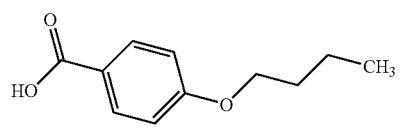 | 194.229 |
| 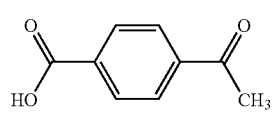 | 164.159 |
| 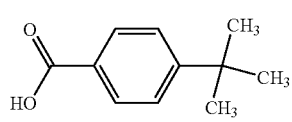 | 178.23 |
| 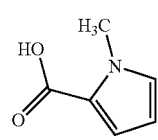 | 125.126 |
| 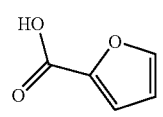 | 112.084 |
| 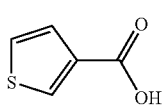 | 128.151 |
| 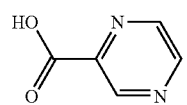 | 124.099 |
| 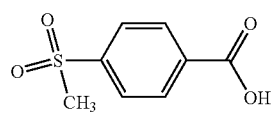 | 200.213 |
| 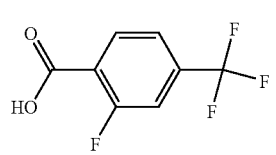 | 201.201 |
| 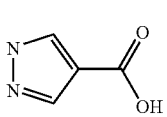 | 112.088 |
| 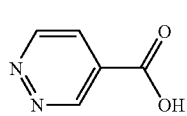 | 124.099 |
| 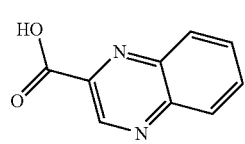 | 174.158 |
| Acid | MW |
|---|---|
| 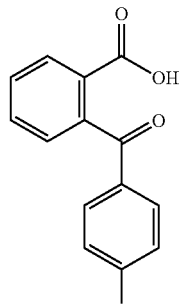 | 240.257 |
| 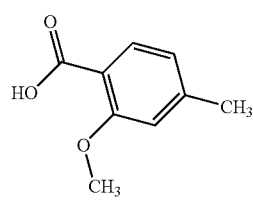 | 166.175 |
| 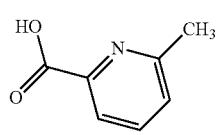 | 137.137 |
| 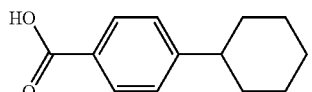 | 204.267 |
| 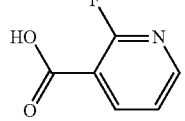 | 141.101 |
| 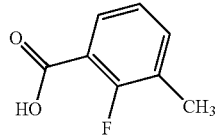 | 154.139 |
| 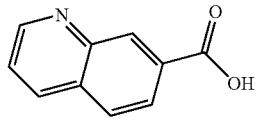 | 173.17 |
| 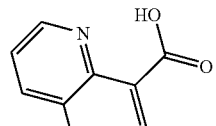 | 173.17 |
| 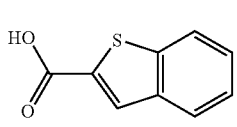 | 178.21 |

-continued
| Acid | MW |
|---|---|
| 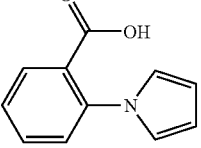 | 187.197 |
| 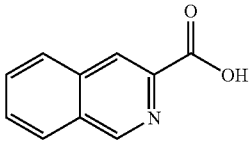 | 173.17 |
|  | 154.139 |
| 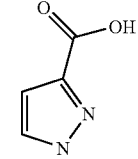 | 112.088 |
| 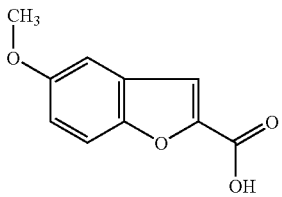 | 192.169 |
| 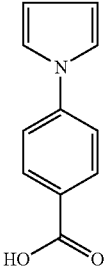 | 187.197 |
| 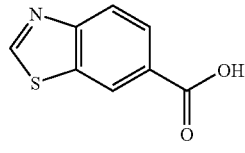 | 179.199 |
| 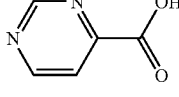 | 124.099 |
| 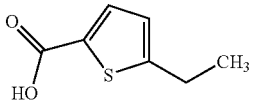 | 156.204 |
-continued
| Acid | MW |
|---|---|
| 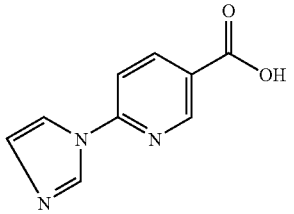 | 189.173 |
| 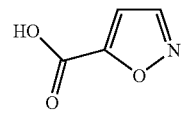 | 113.072 |
| 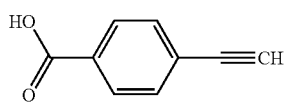 | 146.144 |
| 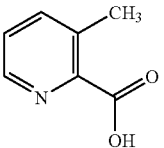 | 137.137 |
| 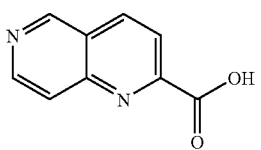 | 174.158 |
| 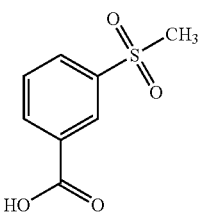 | 200.213 |
| 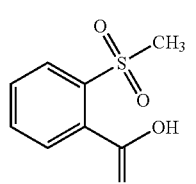 | 200.213 |
| 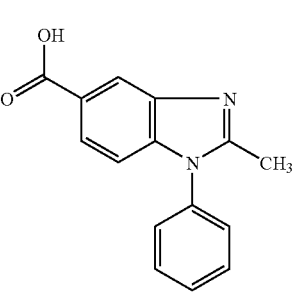 | 252.272 |

-continued
| Acid | MW |
|---|---|
| 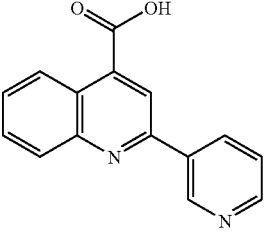 | 250.256 |
| 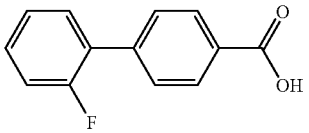 | 216.21 |
| 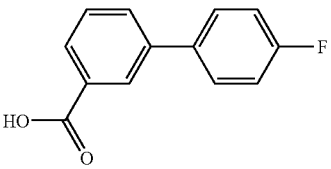 | 216.21 |
| 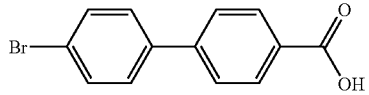 | 277.116 |
| 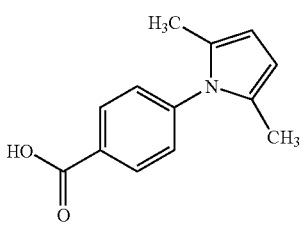 | 215.251 |
| 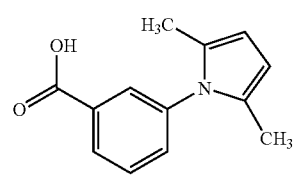 | 215.251 |
| 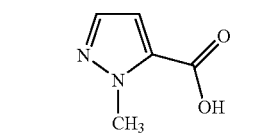 | 126.114 |
| 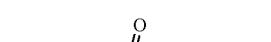 | 129.139 |
| 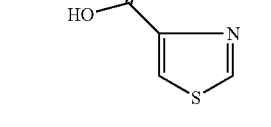 | 143.165 |
-continued
| Acid | MW |
|---|---|
| 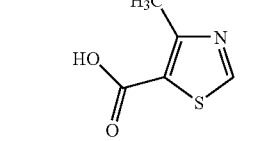 | 124.099 |
| 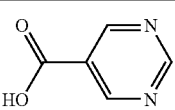 | 127.099 |
| 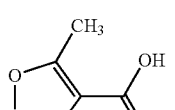 | 126.114 |
| 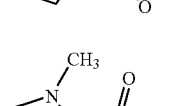 | 222.238 |
| 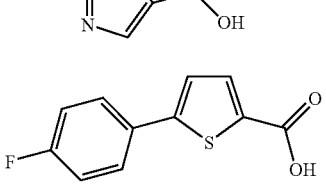 | 174.158 |
| 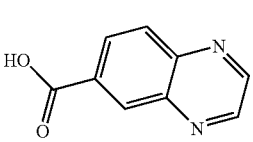 | 230.266 |
| 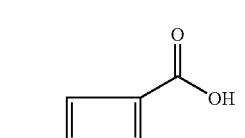 | 221.279 |
| 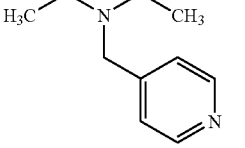 | 257.107 |
| 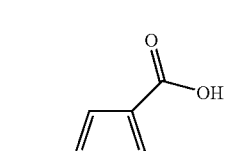 | 223.614 |

-continued

| Acid | MW |
|---|---|
| 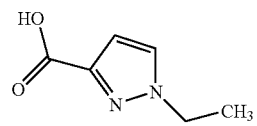 | 140.141 |
| 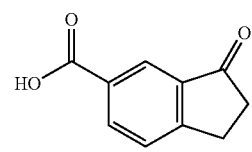 | 176.17 |
| 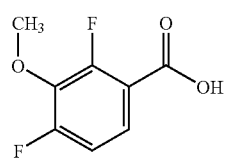 | 188.128 |
| 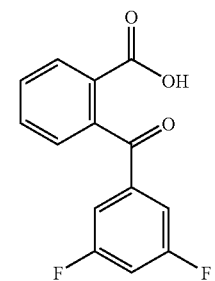 | 262.21 |
| 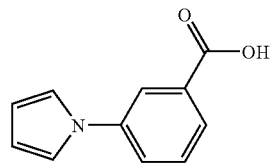 | 187.197 |
| 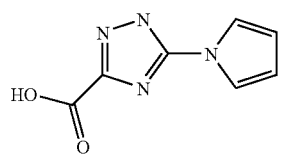 | 178.15 |
| 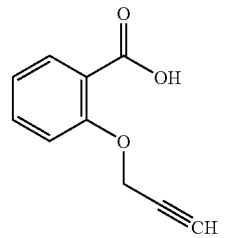 | 176.17 |
| 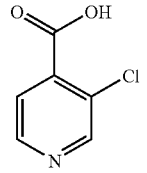 | 157.556 |

-continued

| Acid | MW |
|---|---|
| 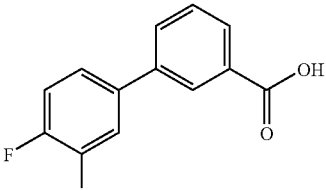 | 234.2 |
| 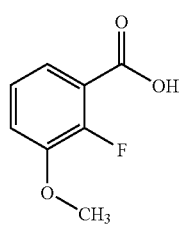 | 170.138 |

The following list includes alkylating reagents which may be employed in the pyridyl alkylation reaction of Scheme 1. Here, the residue of the alkylating agent is located at the $XR^3$ site of the compound of this invention. Optionally, the remainder of the compound will be as found in any of the compounds of examples 2-7.

| Alkylating reagent | MW |
|---|---|
| 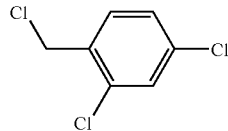 | 195.475 |
| 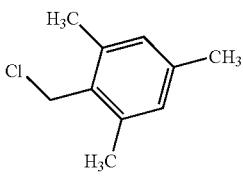 | 168.666 |
| 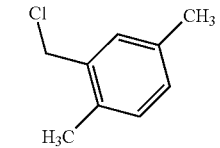 | 154.639 |
| 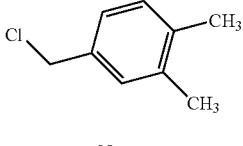 | 154.639 |
| 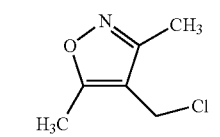 | 145.588 |

| Alkylating reagent | MW |
|---|---|
| 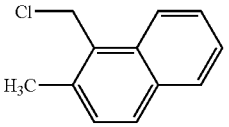 | 190.672 |
| 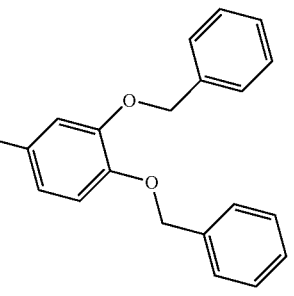 | 338.832 |
| 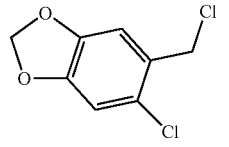 | 205.039 |
| 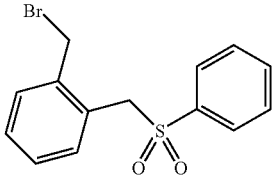 | 325.225 |
| 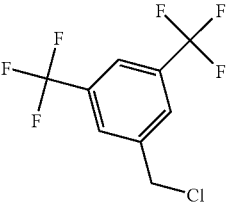 | 262.579 |
| 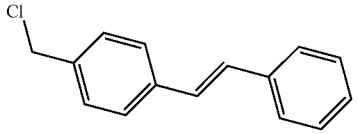 | 228.721 |
| 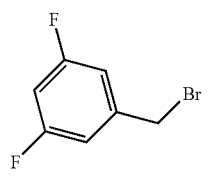 | 207.016 |
| 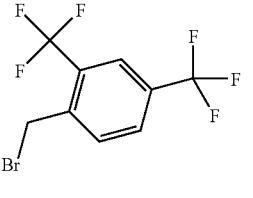 | 307.03 |
| Alkylating reagent | MW |
|---|---|
| 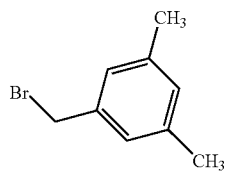 | 199.09 |
| 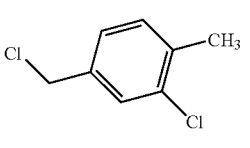 | 175.057 |
| 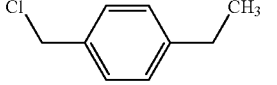 | 154.639 |
| 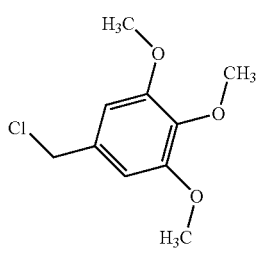 | 216.663 |
| 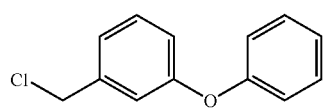 | 218.682 |
| 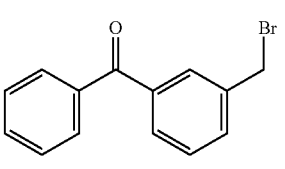 | 275.144 |
| 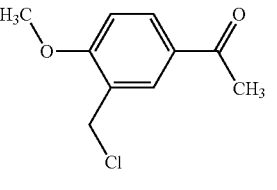 | 198.648 |
| 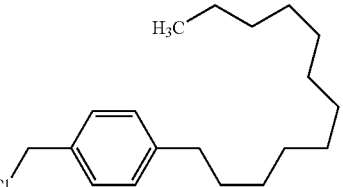 | 294.907 |
| 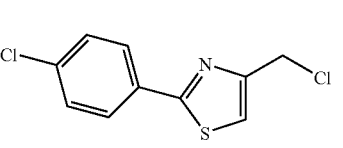 | 244.144 |

-continued
| Alkylating reagent | MW |
|---|---|
|  | 222.084 |
|  | 152.623 |
| 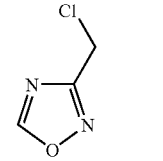 | 118.523 |
| 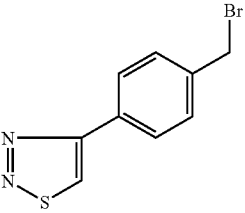 | 255.138 |
| 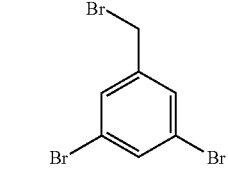 | 328.828 |
| 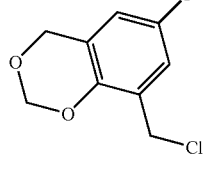 | 202.611 |
| 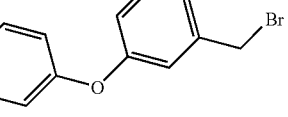 | 281.123 |
| 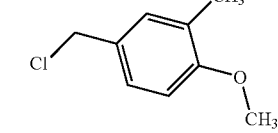 | 170.638 |
| 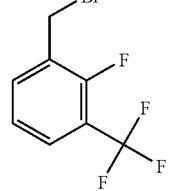 | 257.023 |
-continued
| Alkylating reagent | MW |
|---|---|
| 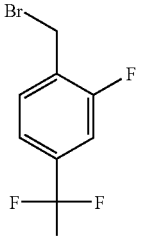 | 257.023 |
| 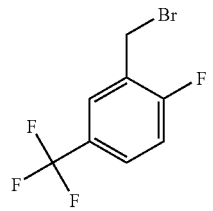 | 257.023 |
| 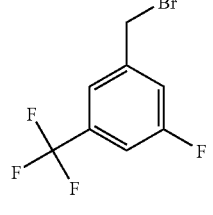 | 257.023 |
| 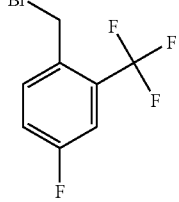 | 257.023 |
| 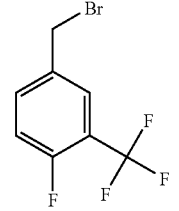 | 257.023 |
| 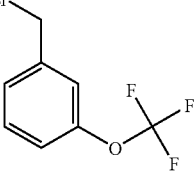 | 255.032 |
| 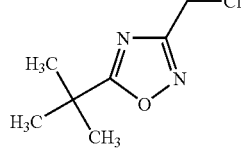 | 174.63 |

| Alkylating reagent | MW |
|---|---|
| 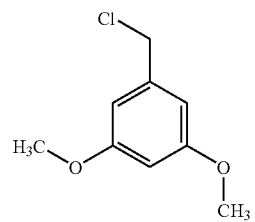 | 186.637 |
| 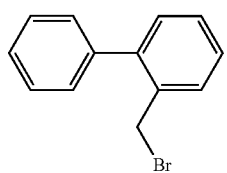 | 247.134 |
| 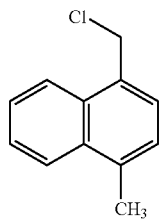 | 190.672 |
| 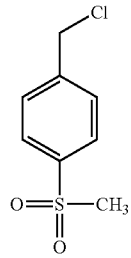 | 204.676 |
| 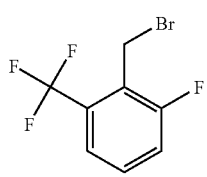 | 257.023 |
| 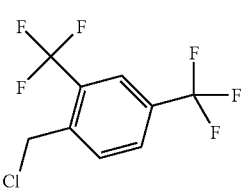 | 262.579 |
| 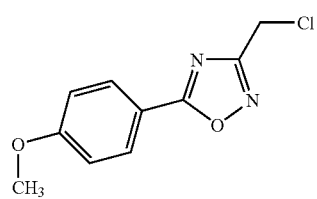 | 224.646 |
| Alkylating reagent | MW |
|---|---|
| 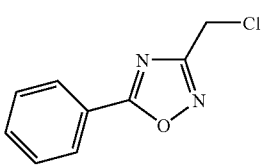 | 194.62 |
| 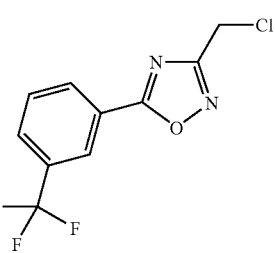 | 262.617 |
| 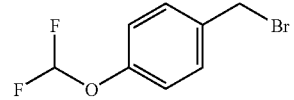 | 237.042 |
| 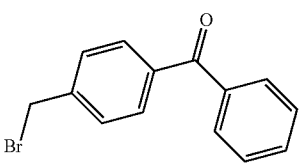 | 275.144 |
| 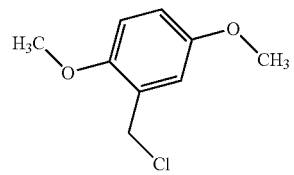 | 186.637 |
| 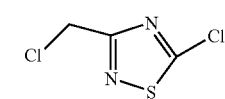 | 169.035 |
| 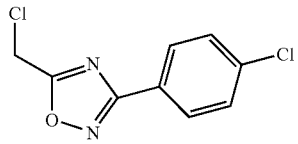 | 229.065 |
| 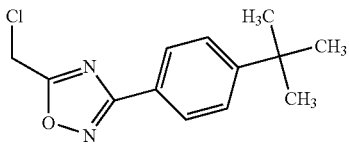 | 250.727 |
| 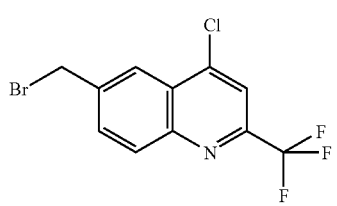 | 324.526 |

| Alkylating reagent | MW |
|---|---|
| 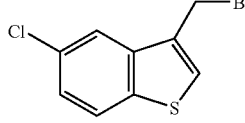 | 261.569 |
| 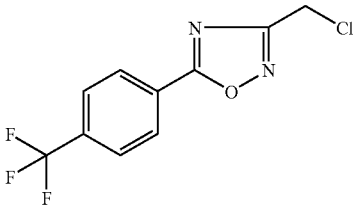 | 262.617 |
| 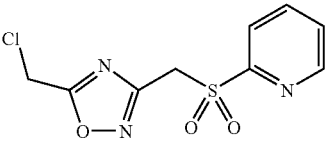 | 273.699 |
| 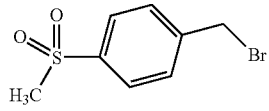 | 249.127 |
| 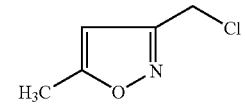 | 131.561 |
| 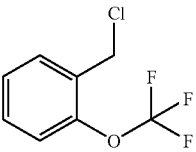 | 210.581 |
| 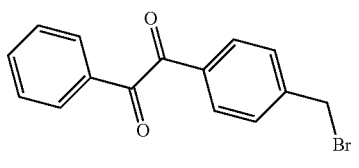 | 303.154 |
| 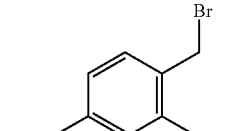 | 223.471 |
| 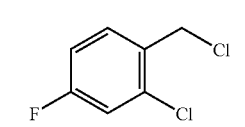 | 179.02 |
| 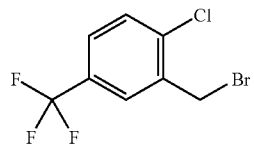 | 273.478 |
| Alkylating reagent | MW |
|---|---|
| 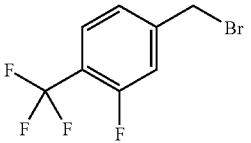 | 257.023 |
|  | 257.023 |
| 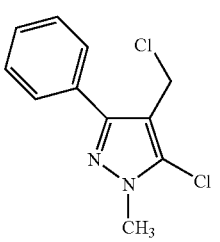 | 241.12 |
| 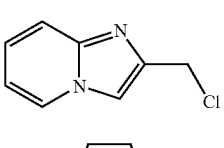 | 166.61 |
| 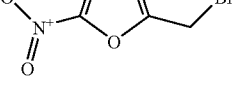 | 205.995 |
| 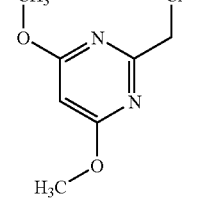 | 188.613 |
| 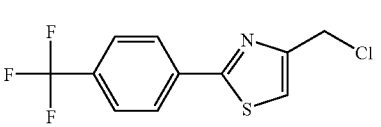 | 277.696 |
| 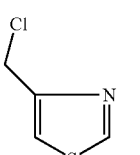 | 133.602 |
| 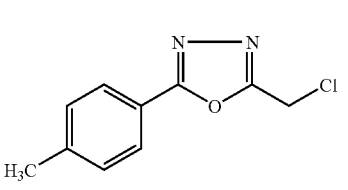 | 208.647 |

-continued
| Alkylating reagent | MW |
|---|---|
| 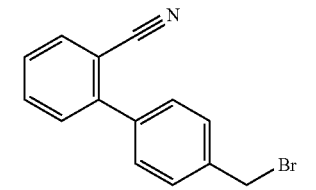 | 272.144 |
| 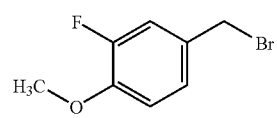 | 219.052 |
| 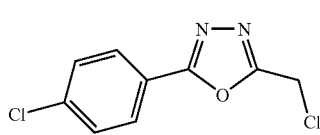 | 229.065 |
| 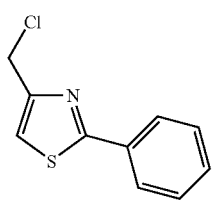 | 209.699 |
| 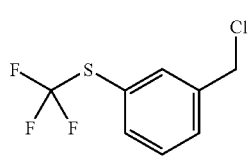 | 226.648 |
| 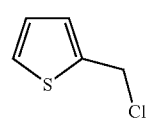 | 132.613 |
| 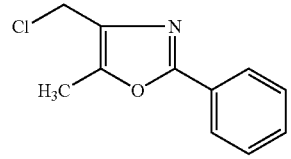 | 207.659 |
|  | 223.471 |
| 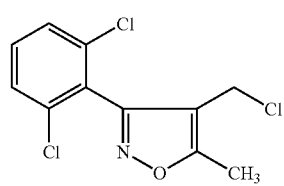 | 276.549 |
-continued
| Alkylating reagent | MW |
|---|---|
| 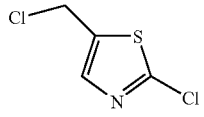 | 168.047 |
| 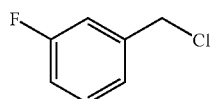 | 162.566 |
| 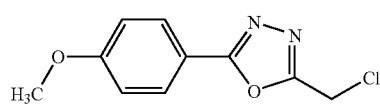 | 224.646 |
| 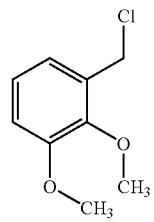 | 186.637 |
| 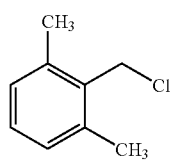 | 154.639 |
| 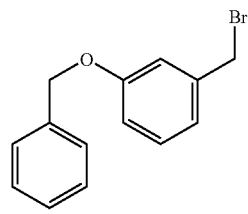 | 277.16 |
| 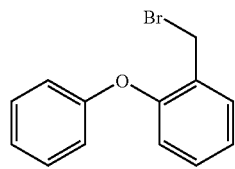 | 263.133 |
| 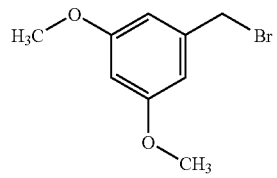 | 231.088 |
| 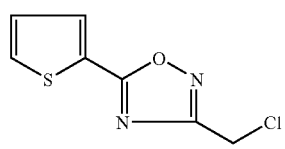 | 200.648 |

-continued
| Alkylating reagent | MW |
|---|---|
| 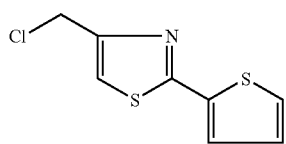 | 215.727 |
| 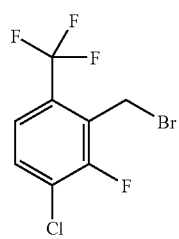 | 291.469 |
| 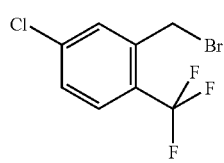 | 273.478 |
| 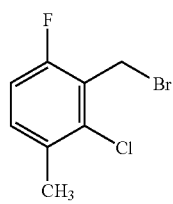 | 237.498 |
| 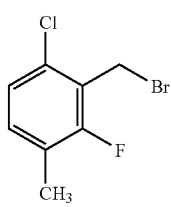 | 237.498 |
| 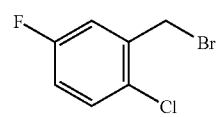 | 223.471 |
| 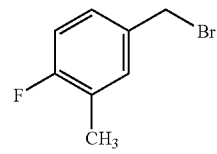 | 203.053 |
| 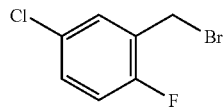 | 223.471 |
| 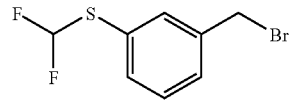 | 253.109 |
-continued
| Alkylating reagent | MW |
|---|---|
| 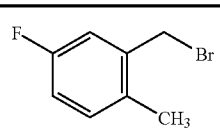 | 203.053 |
| 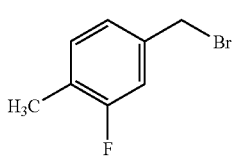 | 203.053 |
| 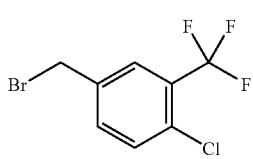 | 273.478 |
| 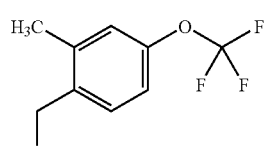 | 269.059 |
| 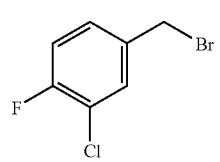 | 223.471 |
| 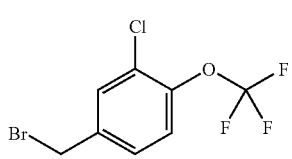 | 289.478 |
| 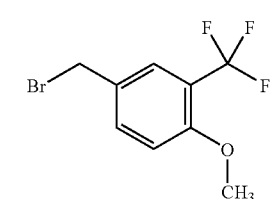 | 269.059 |
| 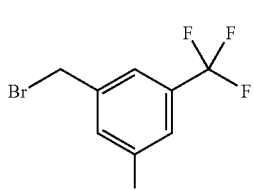 | 253.06 |
| 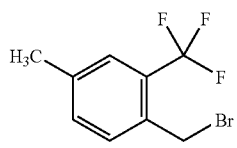 | 253.06 |

| Alkylating reagent | MW |
|---|---|
| 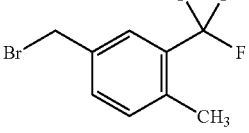 | 253.06 |
| 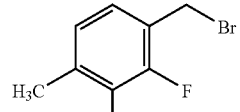 | 221.043 |
| 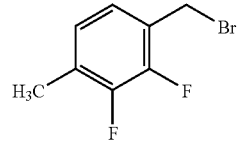 | 285.567 |
| 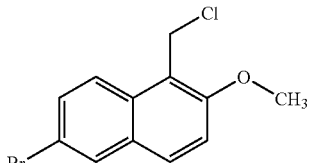 | 344.203 |
| 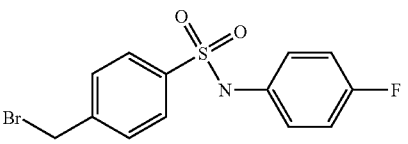 | 261.569 |
| 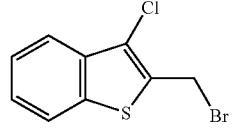 | 212.078 |
| 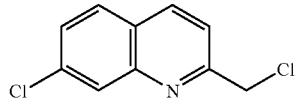 | 195.57 |
| 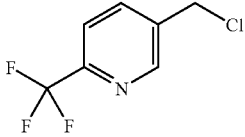 | 299.113 |
| 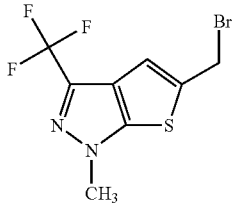 | 228.077 |
| 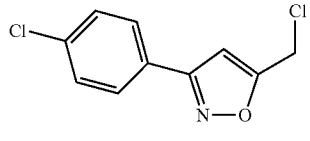 | 193.632 |
| Alkylating reagent | MW |
|---|---|
| 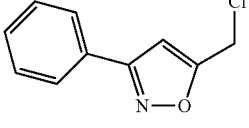 | 223.471 |
| 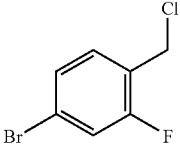 | 255.961 |
| 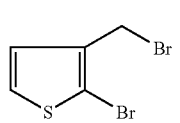 | 252.11 |
| 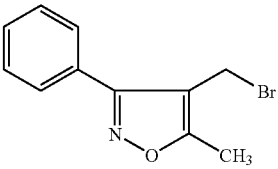 | 190.039 |
| 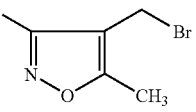 | 176.012 |
| 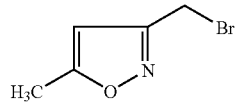 | 237.099 |
| 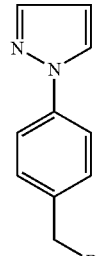 | 238.087 |
| 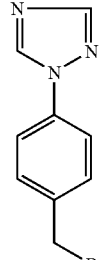 | 239.623 |
| 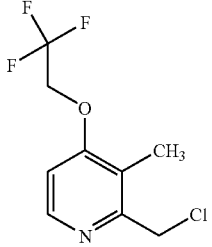 | |

-continued
| Alkylating reagent | MW |
|---|---|
| 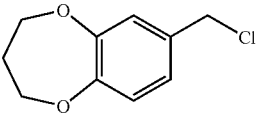 | 198.648 |
| 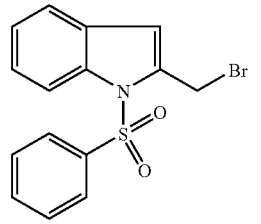 | 350.235 |
| 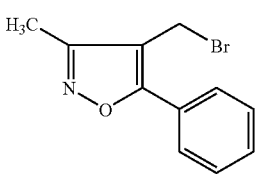 | 252.11 |
| 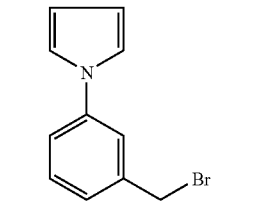 | 236.111 |
| 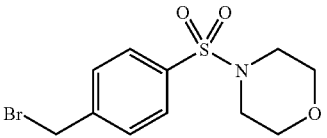 | 320.206 |
| 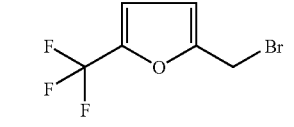 | 228.995 |
| 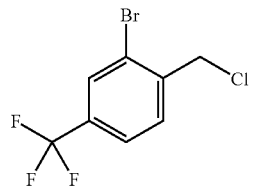 | 273.478 |
| 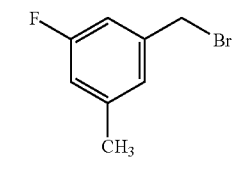 | 203.053 |
-continued
| Alkylating reagent | MW |
|---|---|
| 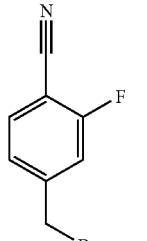 | 214.036 |
| 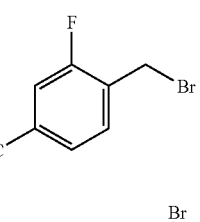 | 203.053 |
| 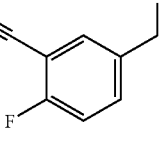 | 214.036 |
| 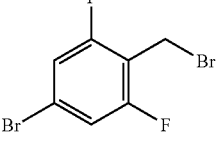 | 285.913 |
| 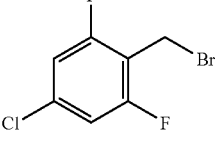 | 241.462 |
| 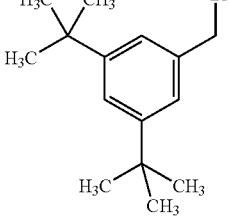 | 283.251 |
| 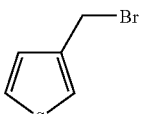 | 177.064 |
| 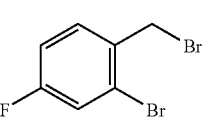 | 267.922 |

-continued
| Alkylating reagent | MW |
|---|---|
| 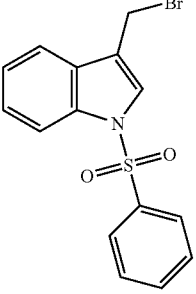 | 350.235 |
| 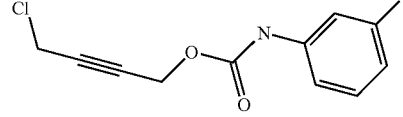 | 350.235 |
| 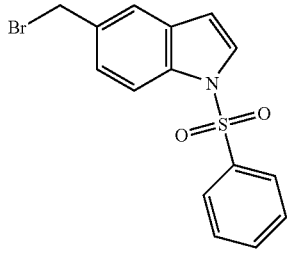 | 196.7 |
| 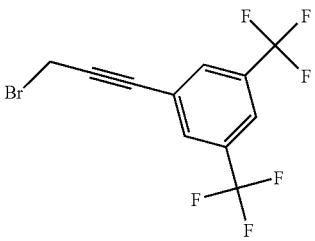 | 199.09 |
| 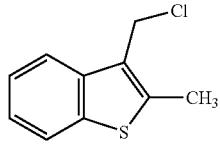 | 199.09 |
| 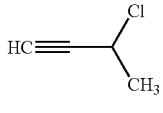 | 199.09 |
| 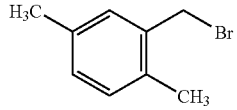 | 199.09 |
| 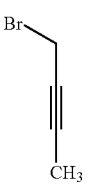 | 253.06 |
-continued
| Alkylating reagent | MW |
|---|---|
| 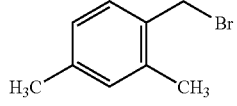 | 258.103 |
| 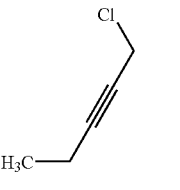 | 331.052 |
| 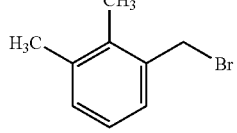 | 88.5365 |
| 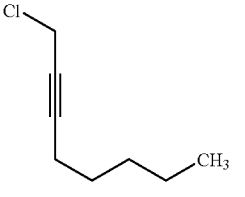 | 132.988 |
| 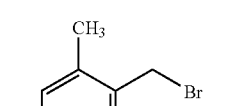 | 102.563 |
| 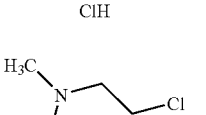 | 144.644 |
| 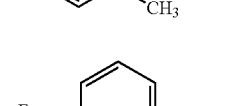 (hydrochloride salt) | 144.044 |
| 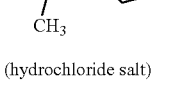 | 296.239 |

61
-continued
| Alkylating reagent | MW |
|---|---|
| ClH | 172.098 |
| 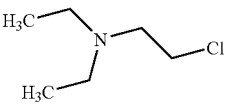 | |
| ClH | 158.071 |
| 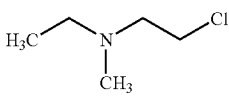 | |
| ClH | 170.082 |
| 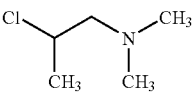 | |
| ClH | 186.081 |
| 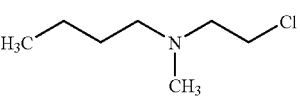 | |
| ClH | 184.109 |
| 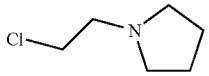 | |
| 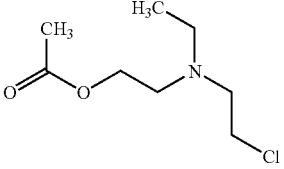 | 149.663 |
| ClH | 248.195 |
|  | |
| ClH | 313.064 |
| 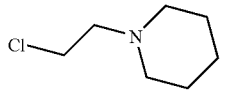 | |
62
-continued
| Alkylating reagent | MW |
|---|---|
| ClH | 158.071 |
|  | |
| ClH | 186.124 |
| 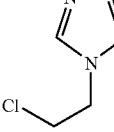 | |
| ClH | 230.133 |
| 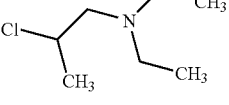 | |
| | 129.589 |
| 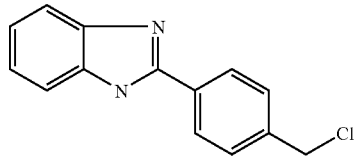 | |
| | 167.038 |
| 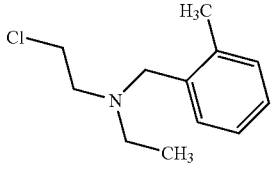 | |
| ClH | |
| 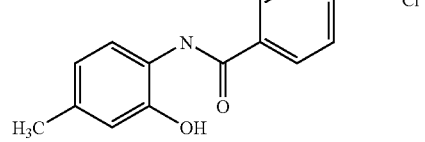 | |
| 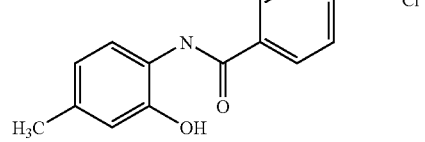 | |

| Alkylating reagent | MW |
|---|---|
| 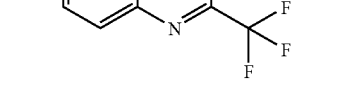 | |
| 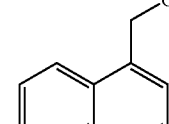 | |
| 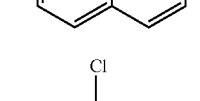 | |
| 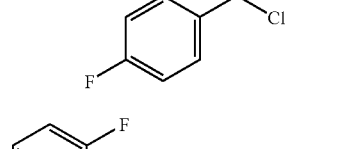 | |
| 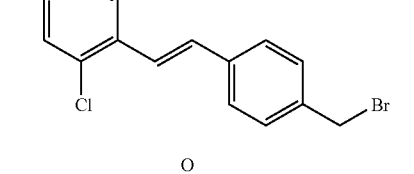 | |
| 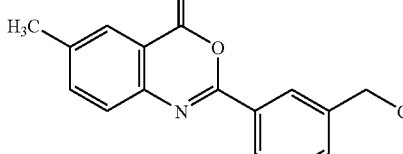 | |
| 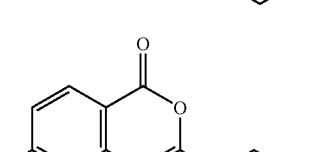 | |
| 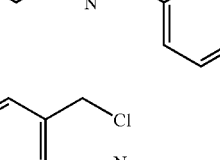 | |

| Alkylating reagent | MW |
|---|---|

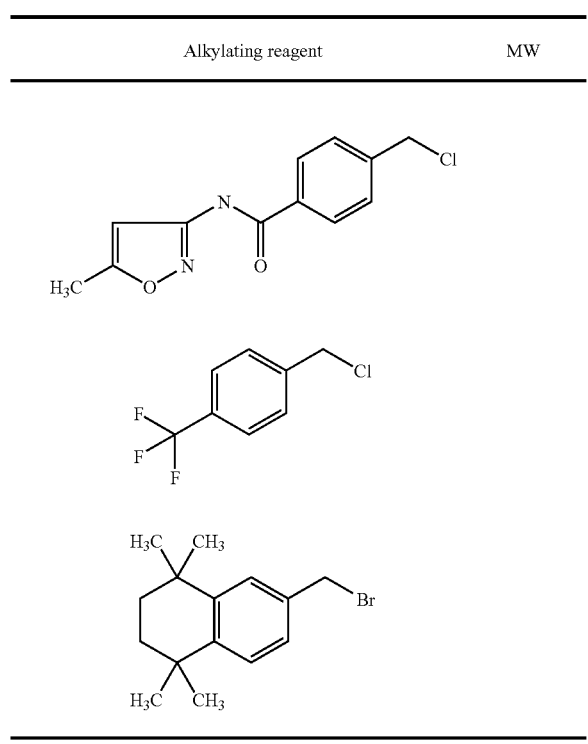

Scheme 2 shows a synthetic route to 5-biarylmethyl-2-phenyl-5H-imidazo[4,5-c]pyridines and 5-benzyl-2-biaryl-5H-imidazo[4,5-c]pyridines.

Scheme 2:

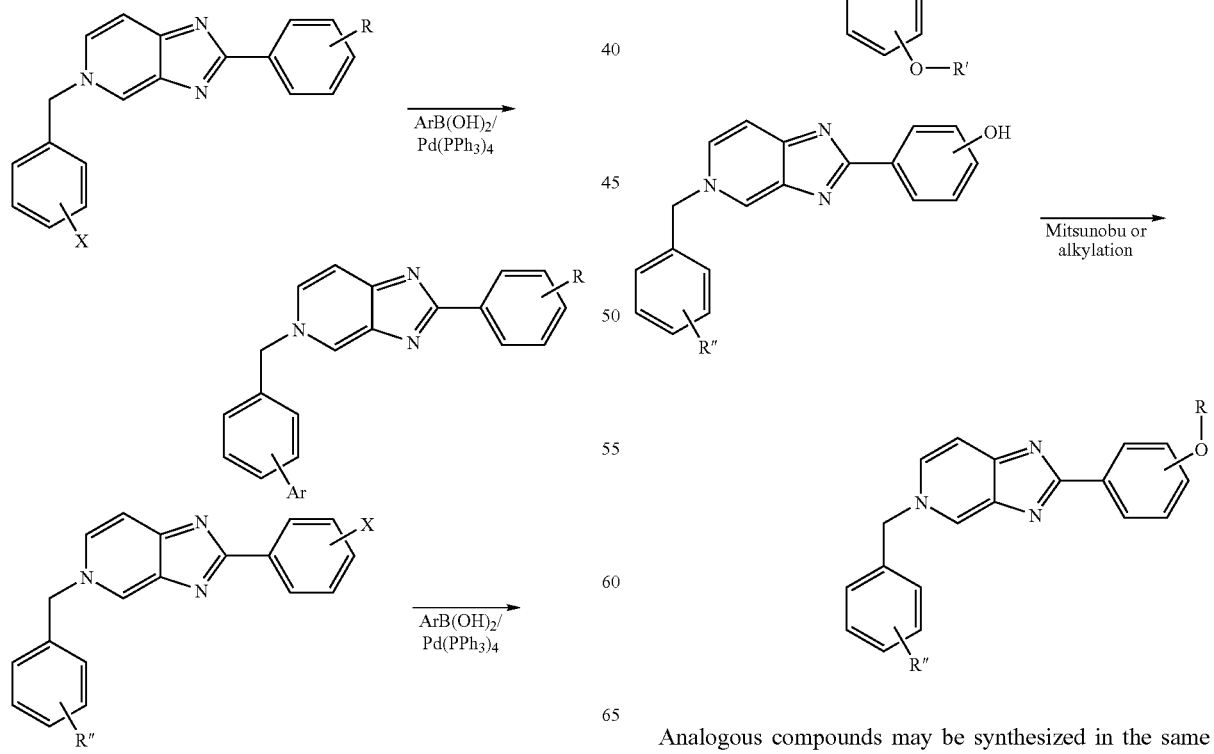

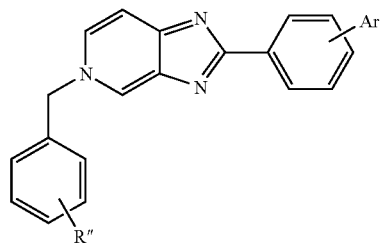

Scheme 3 shows a synthetic route to 5-(alkoxybenzyl)-2-phenyl-5H-imidazo[4,5-c]pyridines and 5-benzyl-2-alkoxybenzyl-5H-imidazo[4,5-c]pyridines. R, R', and R" can be any alkyl, benzylic or heterobenzylic groups.

Scheme 3:

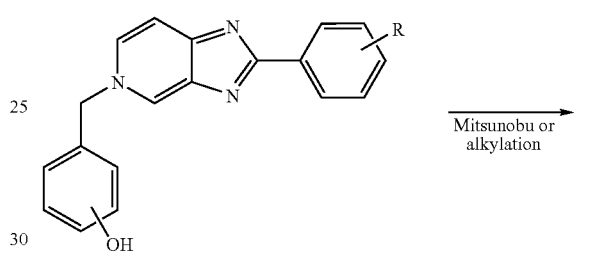

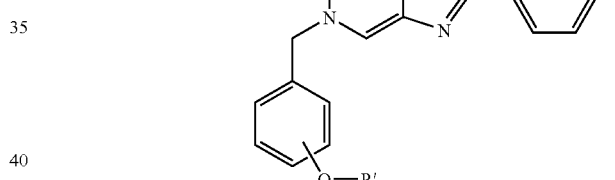

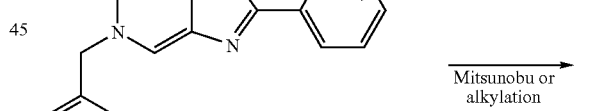

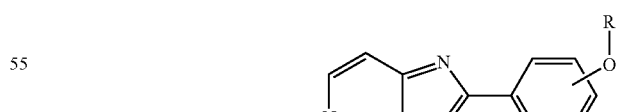

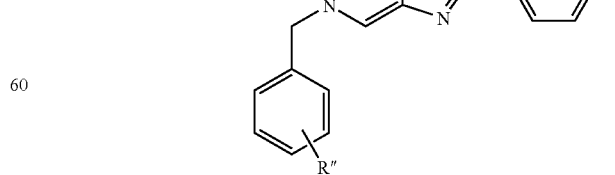

Analogous compounds may be synthesized in the same fashion as in the foregoing schemes by varying the starting

EXAMPLES

Part A

Compound Synthesis

Example 1

2-(2,3-difluorophenyl)-3H-imidazo[4,5-c]pyridine

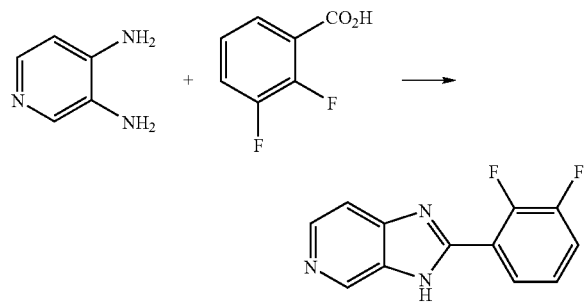

Phosphorous pentoxide (24.56 g) was dissolved in methanesulfonic acid (165.8 mL) at 50° C. with stirring. To the solution, 3,4-diaminopyridine (12.3 g, 0_11 moles) and 2,3-difluorobenzoic acid (19.4 g, 0.12 moles) were added. The reaction mixture was heated to 190° C. for 3 hours. The reaction was done three times. The reaction mixtures was cooled to 50° C. and poured into ice with stirring. At this stage, all three batches were combined. The reaction mixture was neutralized by the addition of NaOH with stirring until the pH is 8. Solid material precipitated out of solution, was collected by filtration and air-dried. The final product was re-crystallized from ethanol/water twice to yield 36 g of 2-(2,3-difluorophenyl)-3H-imidazo[4,5-c]pyridine. 1H 300 Mhz (CD$_3$OD) sigma 7.3-7.42 (m, 1p); 7.43-7.58 (m, 1p); 7.70 (d, 1p); 8.0 (m, 1p); 8.34 (d, 1p); and 8.95 (s, 1p). LC/MS data M/z=232.

Following the above taught procedure and substituting 2-fluorobenzoic acid in place of 2,3-difluorobenzoic acid, the compound 2-(2-fluorophenyl)-3H-imidazo[4,5-c]pyridine can be prepared.

Example 2

5-((3-(4-chlorophenyl)isoxazol-5-yl)methyl)-2-(2-fluorophenyl)-5H-imidazo[4,5-c]pyridine

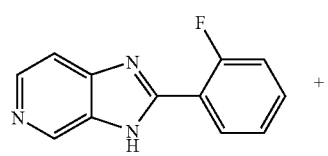

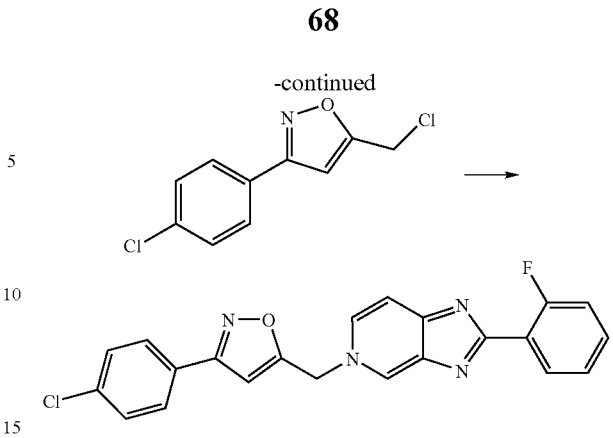

To a suspension of 2-(2-fluorophenyl)-3H-imidazo[4,5-c]pyridine (11.0 g, 50.0 mmoles) in DMF was added a 10% (w/v) solution of aqueous NaOH. To this solution, 5-(chloromethyl)-3-(4-chlorophenyl)isoxazole (13.68 g, 60.0 mmoles) dissolved in DMF was added. The reaction mixture was stirred at room temperature and monitored every half hour by LCMS. The reaction was stopped at 4 hours, after LCMS showed no progress between at 2 hour and 4 hour monitor points. The reaction product was triturated with first with water and then with EtoAc (3×). The material was crystallized by dissolving the material in MeOH with heat, followed by precipitation with water. This crystallization process was then repeated yielding 5-((3-(4-chlorophenyl)isoxazol-5-yl)methyl)-2-(2-fluorophenyl)-5H-imdazo[4,5-c]pyridine (15.385 g, 38 mmole) as white crystal at a yield of 74%. 1H 300 Mhz (d$_6$-DMSO) sigma 6.02 (s, 2p); 7.13 (s, 1p); 7.26-7.35 (m, 2p); 7.43-7.52 (m, 1p); 7.56 (d, 2p); 7.84 (d, 1); 7.89 (d, 2p); 8.24 (d, 1); 8.28-8.36 (m, 1p); and 9.19 (s, 1p). LCMS data M/Z=405.31

Example 3A 5-(4-(trifluoromethoxy)benzyl)-2-(2,3-difluorophenyl)-5H-imidazo[4,5-c]pyridine

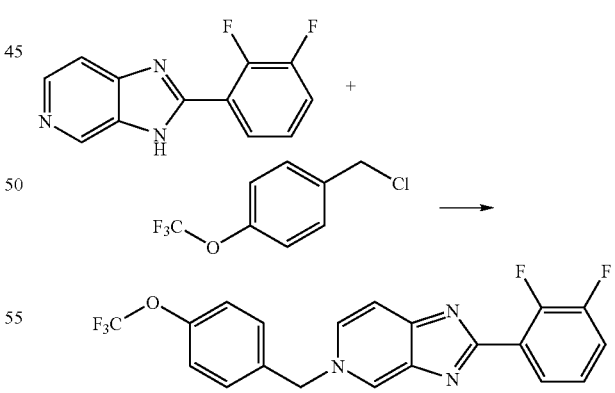

First, 2-(2,3-difluorophenyl)-3H-imidazo[4,5-c]pyridine (20 g, 86.6 mmole) was added to 430 mL of DMF. Some of the solid material did not dissolve. To this solution was added 43 mL of a 10% NaOH (w/v) solution. With vigorous stirring, the un-dissolved material went into solution. The resulting solution was divided into 30 equal portions of 16.3 mL, 3 mmole of 2-(2,3-difluorophenyl)-3H-imidazo[4,5-c]pyridine so as to fit into a microwave reaction vessel. To each reaction vessel was added of 1-(chloromethyl)-4-(trifluoromethoxy) benzene (693 mg, 3 mmole). Each reaction mixture was microwaved for 1 minute at 110° C. Following the completion of all the microwave reactions, all of the reaction vessels were combined (one was lost due to breakage of the vessel) into three batches for workup. For each batch, DMF was removed by vacuum, and the resulting material washed three times with deionized water. The resulting crude material was dissolved in CH$_2$Cl$_2$, Purified using a 330 g SiO$_2$ column (Redisep (Isco) 0% to 0%/5 min to 10% B/30 min to 20%/5 min), and the resulting material was re-crystallized from ethanol/H$_2$O. The three batches yielded 14 g, 33.5 mmole of 5-(4-(trifluoromethoxy)benzyl)-2-(2,3-difluorophenyl)-5H-imidazo[4,5-c]pyridine. 1H 300 Mhz (CD$_3$OD) sigma 5.79 (s, 2p); 7.25-7.35 (m, 1p); 7.37 (d, 2p); 7.38-7.42 (m, 2p); 7.55 (d, 2p); 7.88-7.95 (m, 1p); 8.25 (d, 1p); and 9.05 (s, 1p). LC/MS M/z=406.23.

Example 3B

Following the above-taught procedure, and substituting 1-(chloromethyl)-2,4 difluorobenzene in place of 1-(chloromethyl)-4-(trifluoromethoxy)benzene, the compound 5-(4-iodobenzyl)-2-(2,3-difluorophenyl)-5H-imidazo[4,5-c]pyridine can be prepared.

Example 4

5-(2,4-difluoro-biphenyl)methyl-2-(2,3-difluorophenyl)-5H-imidazo[4,5-c]pyridine

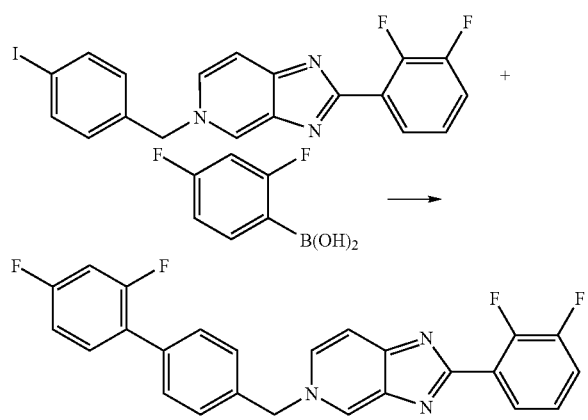

2,4-difluorophenylboronic acid (196 mg, 1.24 mmole) was added to a solution of 5-(4-iodobenzyl)-2-(2,3-difluorophenyl)-5H-imidazo[4,5-c]pyridine (460 mg, 1.03 mmole) in DMF (10 mL). Na$_2$CO$_3$ was dissolved in H$_2$O, added to the DMF solution and stirred. Pd(PPh3)$_4$ was then added to the DMF reaction mixture. The reaction mixture was heated in a microwave at 200° C. for 2 minutes. After extractive work-up using ethyl acetate/water, the crude product was purified in two batches using an Isco 40 g SiO$_2$ column (0 to 10% B/20 min, A=CH$_2$Cl$_2$, B=MeOH, flow rate=40 ml/min) for each purification. The pure product fractions were combined and concentrated. The resulting solid was re-crystallized from CH$_2$Cl/hexane. The collected crystals were dried under high vacuum overnight resulting in 5-(2,4-difluoro-biphenyl)methyl-2-(2,3-difluorophenyl)-5H-imidazo[4,5-c]pyridine (223 mg, 0.515 mmole) at 50% yield. 1H 300 Mhz (CD3OD) sigma 5.8 (s, 2p); 7.0-7.1 (m, 2p); 7.25-7.35 (m, 1p); 7.35- 7.45 (m, 1p); 7.45-7.60 (m, 5p); 7.85 (d, 1p); 7.85-8.0 (m, 1p); 8.3 (d, 1p); and 9.10 (s, 1p). LC/MS data M/z=434.18.

Example 5

5-((3-(4-chlorophenyl)isoxazol-5-yl)methyl)-2-(2,3-difluorophenyl)-5H-imidazo[4,5-c]pyridine

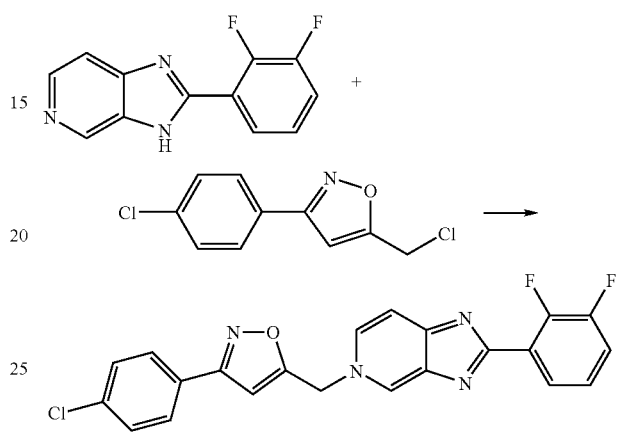

To a solution of azabelizimidazole (10 g, 43.3 mmole) in DMF was added 10% (w/v) aqueous NaOH followed by a solution of 5-(chloromethyl)-3-(4-chlorophenyl)-isoxazole (11.8 g, 51.9 mmole) in DMF. The reaction mixture was stirred at room temperature for 7 hours, and then concentrated. The solid material was treated with EtOAc/H$_2$O, and collected by filtering. The solid material was then tritrated with H$_2$O and EtoAc, and air-dried. The solid was further purified by re-crystallization from MeOH to obtain 5-((3-(4-chlorophenyl)isoxazol-5-yl)methyl)-2-(2,3-difluorophenyl)-5H-imidazo[4,5-c]pyridine (8.5 g, 20.1 mmole) at 46.6% yield. 1H 300 Mhz (DMSO-d6) sigma 6.03 (s, 2p); 7.12 (s, 1p); 7.25-7.35 (m, 1p); 7.44-7.53 (m, 1p); 7.55 (d, 2p); 7.88 (d, 3p); 8.11-8.18 (m, 1p); 8.24-8.29 (dd, 1p); and 9.23 (s, 1p). LC/MS data M/z=423.34, 425.22

Example 6

5-((3-(2,4-trifluoromethyphenyl)isoxazol-5-yl)methyl)-2-(2-fluorophenyl)-5H-imidazo[4,5-c]pyridine

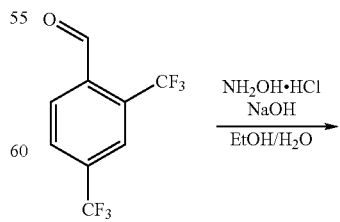

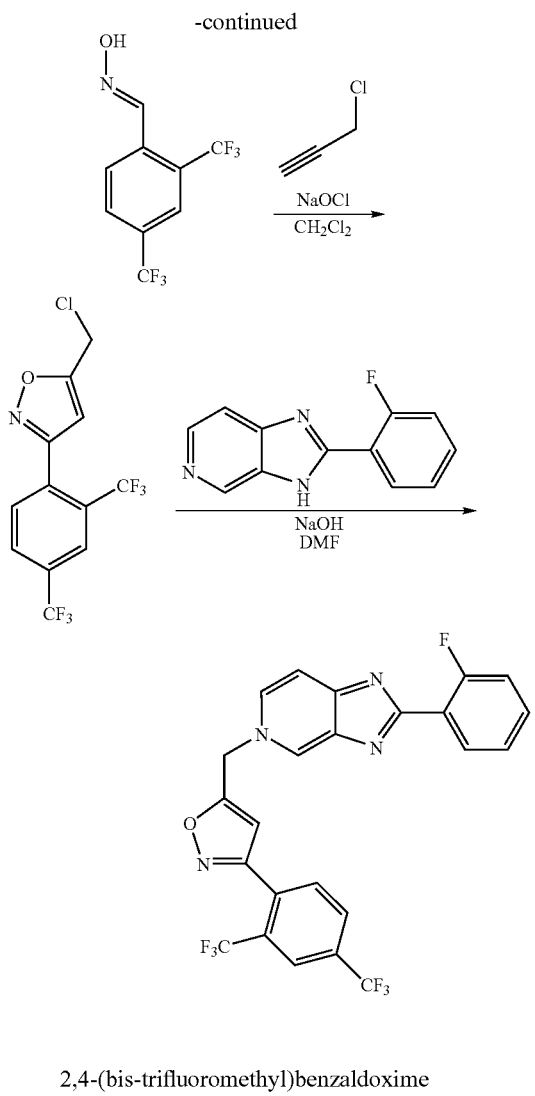

2,4-(bis-trifluoromethyl)benzaldoxime

To aromatic aldehyde (0.021 mol) suspended in EtOH/H$_2$O (1:2, 230 mL, 0.09 M) was added hydroxylamine hydrochloride (1.58 g, 0.023 mol) and cooled to 4° C. To this solution was added aqueous NaOH 50% w/w (4.13 mL, 0.052 mol) dropwise. After stirring for 1.5 h at room temperature, the reaction mixture was acidified with 2N aqueous HCl and extracted with CH$_2$Cl$_2$ (3×50 mL). The organic solution was washed with saturated aqueous NaCl and dried over sodium sulfate. Removal of solvent gave crude oxime (5.3 g, quant.) that was used directly in the next step.

2,4-(bis-trifluoromethyl)phenyl chloromethyl isoxazole 2,4-(bis-trifluoromethyl)benzaldoxime (9.75 g, 0.038 mol) was suspended in CH$_2$Cl$_2$ (45 mL, 0.85 M) and cooled to 4° C. Propargyl chloride (2.72 mL, 0.038 mol) was added to the reaction solution followed by dropwise addition of NaOCl (10-13% free chlorine, 37.6 mL, 0.061 mol). The reaction mixture was stirred at 4° C. for 15 min then heated to reflux for 3 h. After cooling to room temperature, the reaction was partitioned between CH$_2$Cl$_2$ and H$_2$O. The organic layer was separated, washed with saturated aqueous NaCl, and dried over sodium sulfate. After removal of solvent, the crude product chloromethylisoxazole was purified by column chromatography on silica (10% CH$_2$Cl$_2$/hexanes) (6.5 g, 0.020 mol).

5-((3-(2,4-trifluoromethyphenyl)isoxazol-5-yl)methyl)-2-(2-fluorophenyl)-5H-imidazo[4,5-c]pyridine To imidazopyridine (14.28 g, 0.067 mol) suspended in DMF (40 mL) was added aqueous NaOH 10% w/w (32.2 mL, 0.080 mol) dropwise followed by addition of the chloromethyl isoxazole from the previous step (26.3 g, 0.080 mol) in DMF (16 mL). After stirring for 12 h at room temperature, solvents were evaporated to give crude product as a tan solid. The crude solid was triturated with H$_2$O (7×) and crystallized (2×) from MeOH/H$_2$O (2:1) to provide pure title product.

NMR; 300 Mhz D$_6$MSO

Chemical shift, multiplicity, # of protons:
6.1, s, 2
7.0, s, 1
7.3, t, 2
7.4-7.5, m, 1
7.8-7.9, d, 1
7.9-8.0, d, 1
8.2-8.4, m, 4
9.2, s, 1

Example 7

5-((3-(4-trifluoromethyl-2-fluorophenyl)isoxazol-5-yl)methyl)-2-(2-fluorophenyl)-5H-imidazo[4,5-c]pyridine Isoxazole Synthesis

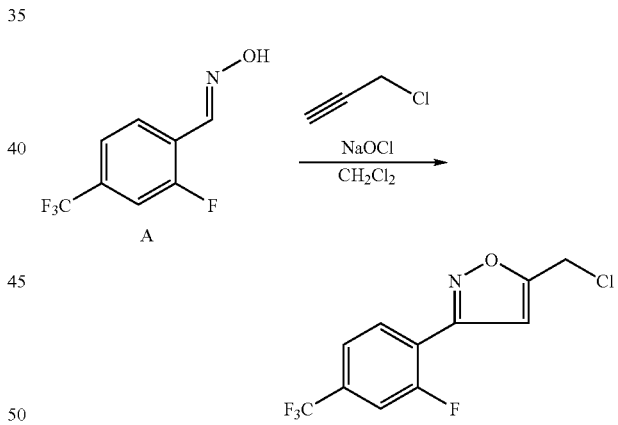

| Compound | MW | Amount | Moles | Equivalents |
|---|---|---|---|---|
| A | 207.13 | 9.3 g | 0.044 | 1 |
| NaOCl (10% free Cl) | 74.44 | 43.0 mL | 0.44 | 1.6 |
| Propargyl chloride | 74.51 | 3.14 mL | 0.044 | 1 |
| Dichloromethane | | 48.7 mL | | |

"A" was suspended in dichloromethane at 0° C. and NaOCl was added at 0° C. with vigorous stirring, followed by propargyl chloride. Reaction stirred at 0° C. for 5 min and then heated to reflux for 2 h. It was then cooled to room temperature, washed with water, dried over sodium sulfate and concentrated in vacuo to obtain a yellow solid. It was purified on the combiflash on a silica gel column, eluting with 3-50% ethyl acetate-hexanes. 4.5 g of shiny white solid obtained.

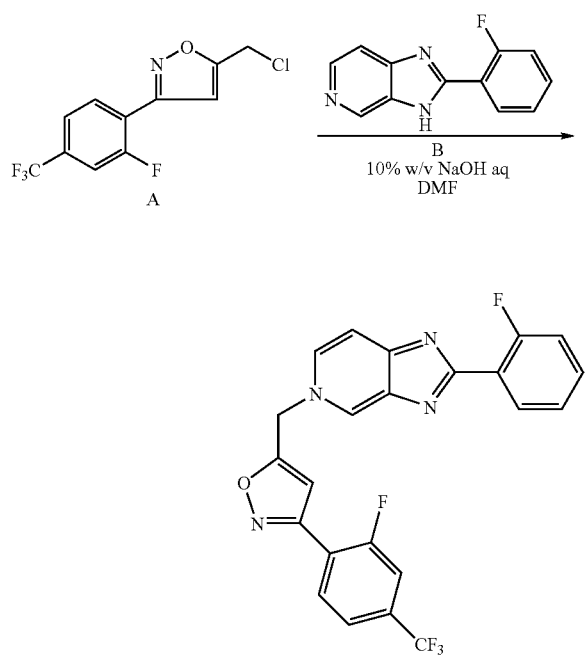

| Compound | MW | Amount | mMoles | Equivalents |
|---|---|---|---|---|
| A | 279.62 | 2.0 g | 7.6 | 1.2 |
| B | 213.21 | 1.373 g | 6.4 | 1 |
| 10% w/v aq NaOH | | 2.26 mL | | |
| DMF | | 13.73 mL + 6.56 mL | | |

"B" was suspended in 13.73 mL DMF and 10% (w/v) aq. NaOH was added to it. "A" was dissolved in 6.56 mL DMF and this solution was added to the above with stirring. The reaction was stirred at room temperature for 5 hours. DMF was removed by concentrating in vacuo and the solid obtained was triturated with water two times and then with ethyl acetate. The solid thus obtained was recrystallized from methanol-water to obtain 533 mg of the desired compound.

NMR (DMSO) Data:

Chemical shift, multiplicity, # of protons:

6.14, s, 2
7.18, d, 1
7.28-7.36, m, 2
7.44-7.54, m, 1
7.70-7.76, d, 1
7.86-7.90, d, 1
7.90-7.96, d, 1
8.08-8.16, t, 1
8.28-8.36, t, 2
9.24, s, 1

Example 8A 5-((3-(2-trifluoromethyl-4-fluorophenyl)isoxazol-5-yl)methyl)-2-(2-fluorophenyl)-5H-imidazo[4,5-c]pyridine

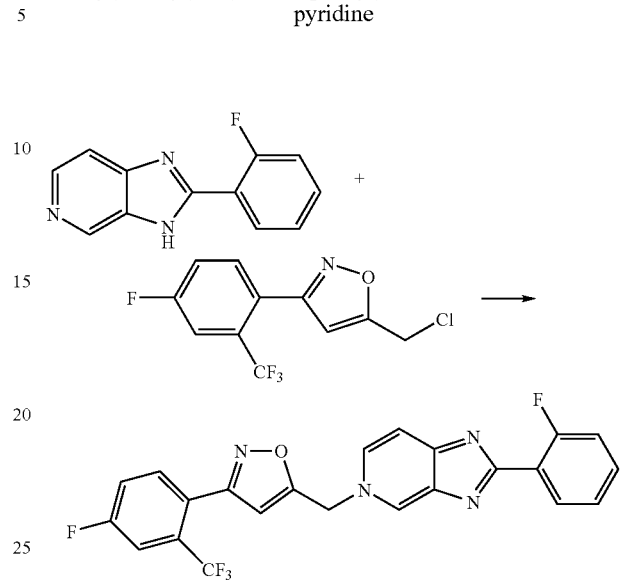

To a solution of azabenzimidazole (12.7 g, 59.6 mmole) in DMF (120 mL) was added 10% (w/v) aqueous NaOH (30.5 mL, 76.6 mmole) followed by a solution of 5-(chloromethyl)-3-(2-trifluoromethyl-4-fluorophenyl)-isoxazole (21.3 g, 76.6 mmole) in DMF (60 mL). The reaction mixture was stirred at room temperature for 18 hours, and then concentrated. The material was precipitated from MeOH/H₂O, and collected by filtering. The solid material was recrystallized from EtoAc/hexanes to obtain 5-((3-(2-trifluoromethy-4-fluorophenyl)isoxazol-5-yl)methyl)-2-(2-fluorophenyl)-5H-imidazo[4,5-c]pyridine in 69% yield.

NMR Data 300 Mhz $D_6$MSO

Chemical shift, multiplicity, #of protons:

6.15, s, 2
6.91, s, 1
7.3, t, 2
7.42-7.52, m, 1
7.65-7.9, m, 2
7.84-7.9, m, 2
8.22-8.45, m, 2
9.19, S, 1

Example 8B

Salts of 5-((3-(2-trifluoromethyl-4-fluorophenyl)isoxazol-5-yl)methyl)-2-(2-fluorophenyl)-5H-imidazo[4,5-c]pyridine Methanesulfonic Acid Salt 5-((3-(2-trifluoromethyl-4-fluorophenyl)isoxazol-5-yl)methyl)-2-(2-fluorophenyl)-5H-imidazo[4,5-c]pyridine free base (200 mg) was slurried in 2.0 mL acetone. Methanesulfonic acid (42.6 mg) was added and the mixture was warmed to ~60° C. Water was added in small increments until a solution was formed (110 μL required). The solution was cooled to ambient temperature and stirred overnight. The slurry was cooled in an ice bath before being filtered and washed with acetone. The solid obtained was dried at 40° C. to give 149 mg of the desired salt. DSC endotherm 213.1° C. NMR was consistent with the desired structure.

HCl Salt 5-((3-(2-trifluoromethyl-4-fluorophenyl)isoxazol-5-yl)methyl)-2-(2-fluorophenyl)-5H-imidazo[4,5-c]pyridine free base (200 mg) was slurried in 2.0 mL acetone. Concentrated hydrochloric acid (46 mg) was added and the mixture was warmed to ~60° C. Water was added to the thick slurry in small increments until a solution was formed (100 μL required). The solution was cooled to ambient temperature and stirred overnight. The slurry was cooled in an ice bath before being filtered and washed with acetone. The solid obtained was dried at 40° C. to give 80 mg of the desired salt. DSC endotherm 241.5° C. NMR consistent with the desired structure.

Example 8B

Formulation of 5-((3-(2-trifluoromethyl-4-fluorophenyl)isoxazol-5-yl)methyl)-2-(2-fluorophenyl)-5H-imidazo[4,5-c]pyridine salts Either salt of Example 7B was mixed 1:1 by weight in dry pregelatinized starch. 100 mg of the mixture was loaded into a hard gel capsule.

Additional compounds of this invention were made by the methods of procedures A, C, D, E and F.

Procedure A; Alkylation

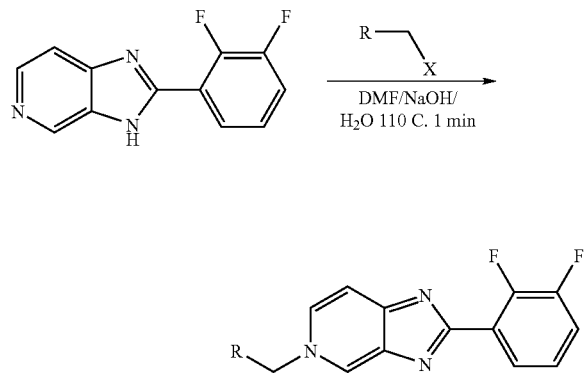

For compounds prepared in an array format, 100 um of the scaffold (in this case 2-(2,3-Difluoro-phenyl)-3H-imidazo[4,5-c]pyridine) was used for each reaction. The total amount of 2-(2,3-Difluoro-phenyl)-3H-imidazo[4,5-c]pyridine was dissolved in enough DMF to give 500 ul/reaction. To each solution was added 60 μL of 10% (w/v)NaOH/H₂O. The alkylating agents were dissolved in DMF at a concentration 480 μmole/mL and 250 μL of these solutions were added to the respective reaction. Each reaction was then heated to 110° C. for 1 min using microwave irradiation. After cooling, the reactions were filtered through a 0.45 um filter. Each compound was then purified by mass based fractionation on a C-18 reverse phase column using 0.1% TFA/H₂O and 0.1% TFA/Acetonitrile as the eluting solvents. Each compound was identified by its mass spectrum and purity was determined by UV absorbance at 254 nm. The HPLC fractions were concentrated by centrifugal evaporation and weighed to determine quantity collected.

Procedure C; Suzuki Boronic Acid

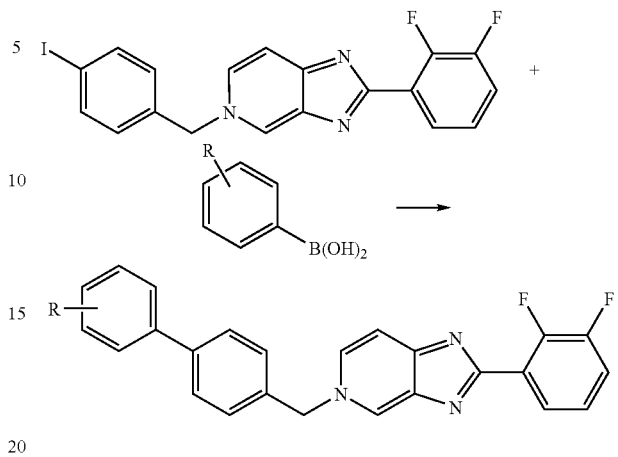

The aryl boronic acid (1.2 eq.) was added to a solution of 5-(4-iodobenzyl)-2-(2,3-difluorophenyl)-5H-imidazo[4,5-c]pyridine (1 eq.) in DMF. Na₂CO₃ (2 eq) was dissolved in H₂O, added to the DMF solution and stirred. Pd(PPh3)4 (5 mole %) was then added to the DMF reaction mixture. The reaction mixture was heated in a microwave at 200° C. for 2 minutes. The reaction mixture was applied to a 1 g solid phase extraction cartridge (C-18) and the column washed with 3×2 mL of methanol. The eluents were filtered through a 0.45 um filter and then concentrated to dryness. The resulting material was redissolved in DMF, and purified by reverse phase HPLC/MS.

Procedure D

General Procedure for Oxime Formation

To aromatic aldehyde suspended in EtOH/H₂O (1:2) was added hydroxylamine hydrochloride (1.1 equiv.) and cooled to 4° C. To this solution was added aqueous NaOH 50% w/w (2.5 equiv.) dropwise. After stirring for 1.5 h at room temperature, the reaction mixture was acidified with 2N aqueous HCl and extracted with CH₂Cl₂. The organic solution washed with saturated aqueous NaCl and dried over sodium sulfate. Removal of solvent gave crude oxime that was used directly in the next step.

General Procedure for Cycloaddition

Oxime was suspended in CH₂Cl₂ and cooled to 4° C. Propargyl chloride (1 equiv.) was added to the reaction solution followed by dropwise addition of NaOCl (10-13% free chlorine, 1 equiv.). The reaction mixture was stirred at 4° C. for 15 min then heated to reflux for 3 h. After cooling to room temperature, the reaction was partitioned between CH₂Cl₂ and H₂O. The organic layer was separated, washed with saturated aqueous NaCl, and dried over sodium sulfate. After removal of solvent, the crude product was purified by trituration (hexanes) or by column chromatography on silica (10% CH₂Cl₂/hexanes).

General Procedure for Alkylation

To imidazopyridine suspended in DMF was added aqueous NaOH 10% w/w (1.2 equiv.) dropwise followed by addition of chloromethyl isoxazole (1.2 equiv.) in DMF. After stirring for 12 h at room temperature, solvents were evaporated to give crude product as a tan solid. The crude solid was triturated with H₂O and crystallized from MeOH/H₂O (2:1) to provide pure final product.

Procedure E; Suzuki Bromides

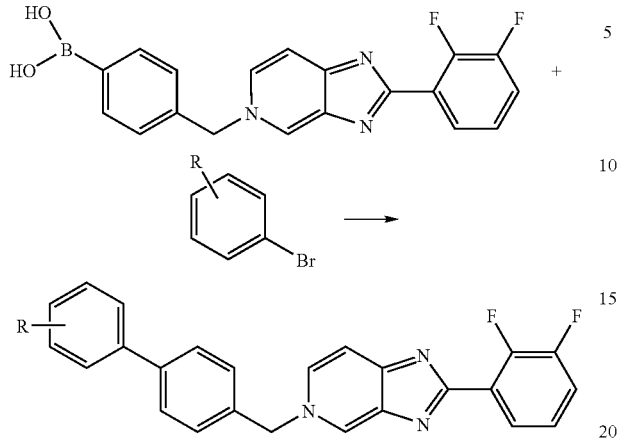

The aryl bromide (1.2 eq.) was added to a solution of 4-((2-(2,3-difluorophenyl)-5H-imidazo[4,5-c]pyridin-5-yl)methyl)phenylboronic acid (1 eq.) in DMF. $Na_2CO_3$ (2 eq) was dissolved in $H_2O$, added to the DMF solution and stirred. $Pd(PPh_3)_4$ (5 mole %) was then added to the DMF reaction mixture. The reaction mixture was heated in a microwave at 200° C. for 2 minutes. The reaction mixture was applied to a 1 g solid phase extraction cartridge ($C_{1-18}$) and the column washed with 3×2 mL of methanol. The eluents were filtered through a 0.45 um filter and then concentrated to dryness. The resulting material was redissolved in DMF, and purified by reverse phase HPLC/MS.

Procedure F

Preparation of Biphenyl Array

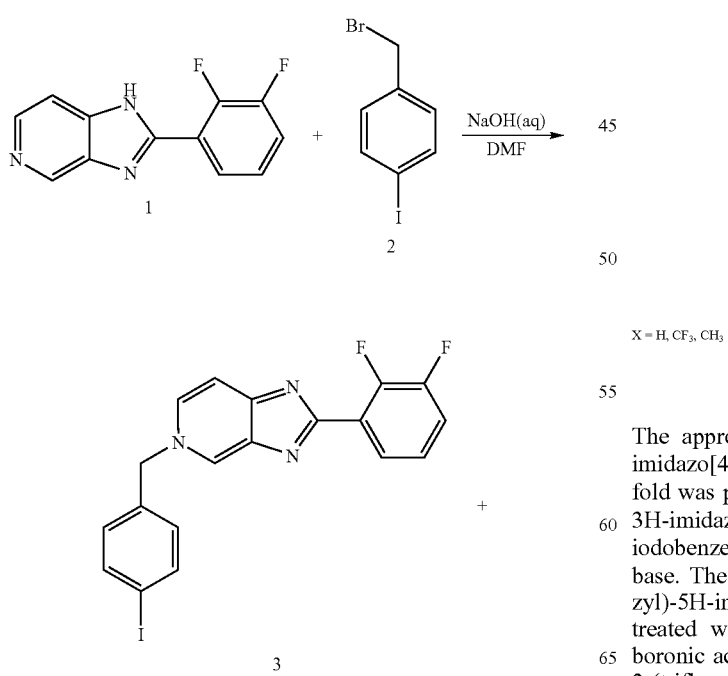

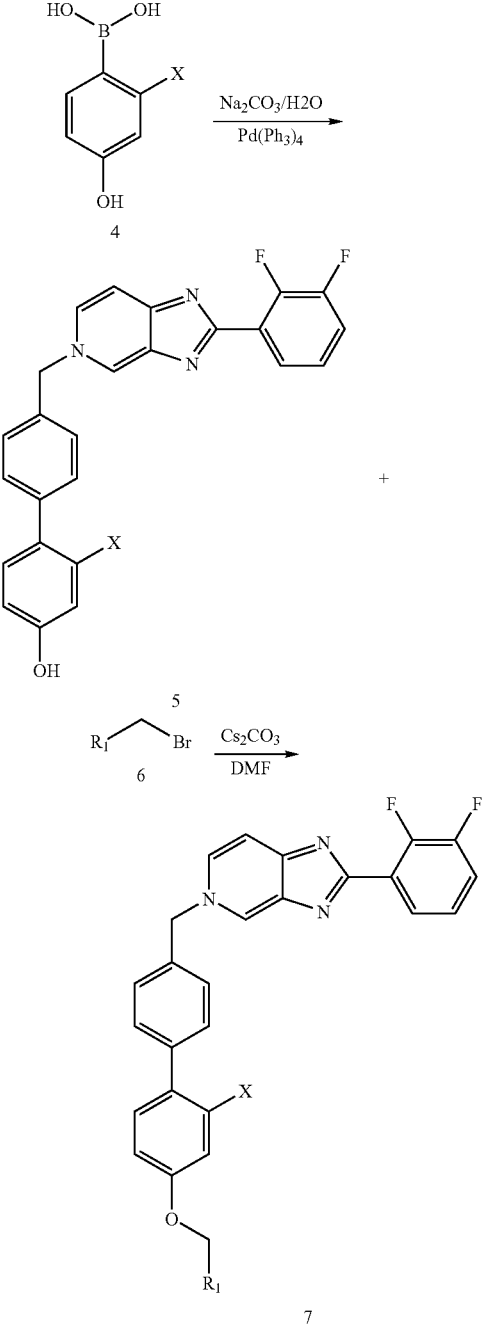

X = H, CF₃, CH₃

The appropriately substituted 4'-[2-(2,3-Difluoro-phenyl)-imidazo[4,5-c]pyridin-5-ylmethyl]-biphenyl-4-ol (5) scaffold was prepared by first treating 2-(2,3-Difluoro-phenyl)-3H-imidazo[4,5-c]pyridine) (1) with 1-bromomethyl-4-iodobenzene (2) in DMF using aqueous sodium hydroxide as base. The resulting 2-(2,3-Difluoro-phenyl)-5-(4-iodo-benzyl)-5H-imidazo[4,5-c]pyridine (3) (1 equivalent) was treated with three different substituted 4-hydroxyphenyl boronic acids ((4-hydroxyphenyl)boronic acid, 4-Hydroxy-2-(trifluoromethyl)phenyl boronic acid and (4-hydroxy-2-methylphenyl)boronic acid) and (4-Fluoro-2-hydroxy)phenylboronic acid (1.1 equivalents) under Suzuki coupling conditions (sodium carbonate, water, palladium tetrakis (triphenyl)phosphine) to afford the appropriately substituted 4'-[2-(2,3-Difluoro-phenyl)-imidazo[4,5-c]pyridin-5-ylmethyl]-biphenyl-4-ol or -[2-(2,3-Difluoro-phenyl)-imidazo[4,5-c]pyridin-5-ylmethyl]-biphenyl-2-ol. The products were precipitated in ethyl acetate and filtered over a medium frit followed by washing with water to afford the pure product (5).

For compounds prepared in array format of the general type (7), 50 µM of the scaffold (5) in 250 µL DMF was used for each reaction. To each reaction was added 1.4 equivalents of Cesium Carbonate. The alkylating agents (6) were added as a 0.4M solution (0.05 mMoles) in DMF. The reactions were shaken at 60° C. for 4 hours and monitored by analytical LC/MS. Each reaction was filtered through a 0.45 µM filter and purified by mass-based fractionation on a C-18 reverse phase column using 0.1% TFA/water and 0.1% TFA/acetonitrile as the eluting solvents. Each compound was identified by its mass spectrum and purity was determined by its UV absorbance at 254 nm. The HPLC fractions were concentrated in vacuo and weighed to afford the product (7) as its trifluoroacetate salt.

The compounds produced according to these procedures and examples, and certain of their properties, are described in the Table below. The substituent designated "C" is methyl.

| Structures | Purity | MW | Obs. MW | Method |
| --- | --- | --- | --- | --- |
| Example 9 | 95 | 387.340 | 388.340 | A |
| Example 10 | 90 | 395.440 | 396.440 | A |
| Example 11 | 90 | 413.431 | 414.431 | A |
| Example 12 | 92 | 404.451 | 405.451 | A |

-continued
| Structures | Purity | MW | Obs. MW | Method |
|---|---|---|---|---|
| Example 13 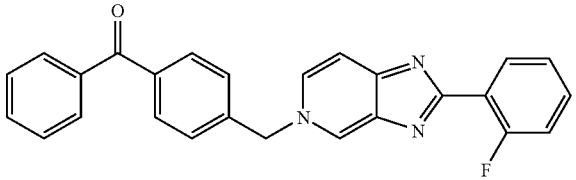 | 95 | 407.451 | 408.451 | A |
| Example 14 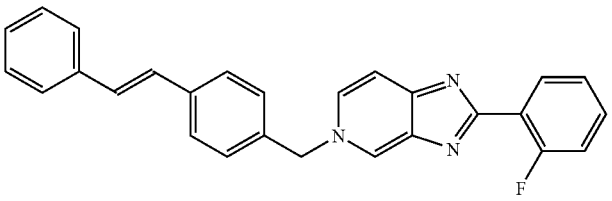 | 85 | 405.479 | 406.479 | A |
| Example 15 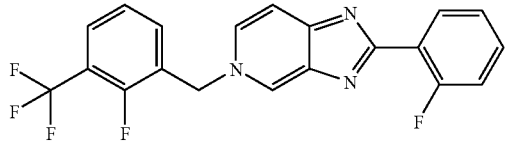 | 90 | 389.331 | 390.331 | A |
| Example 16 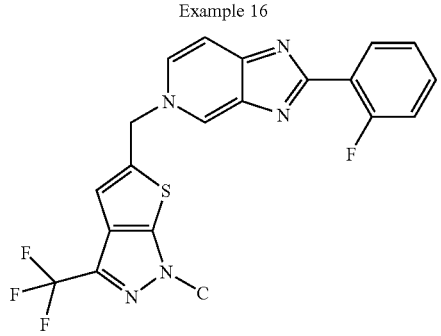 | 90 | 431.418 | 432.418 | A |
| Example 17 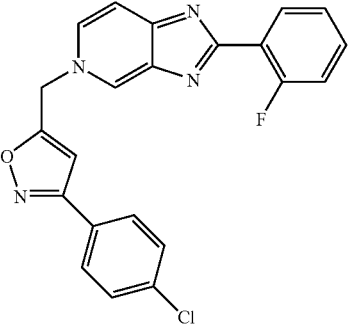 | 93 | 404.834 | 405.834 | A |

-continued
| Structures | Purity | MW | Obs. MW | Method |
|---|---|---|---|---|
| Example 18 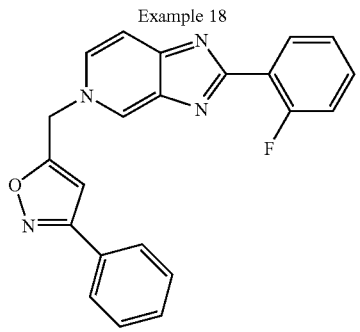 | 90 | 370.389 | 371.389 | A |
| Example 19 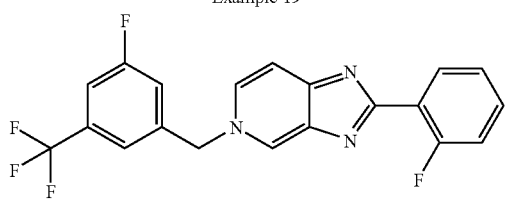 | 95 | 389.331 | 390.331 | A |
| Example 20 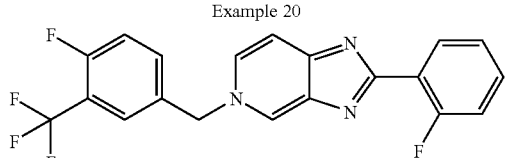 | 95 | 389.331 | 390.331 | A |
| Example 21 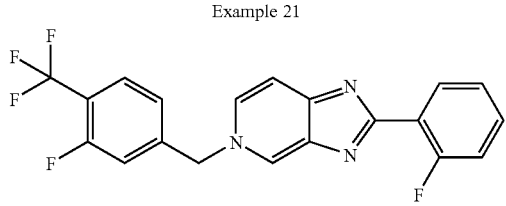 | 95 | 389.331 | 390.331 | A |
| Example 22 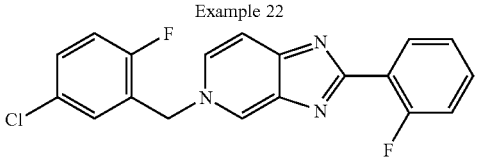 | 97 | 355.777 | 356.777 | A |
| Example 23 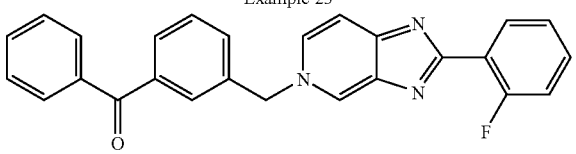 | 90 | 407.451 | 408.451 | A |
| Example 24 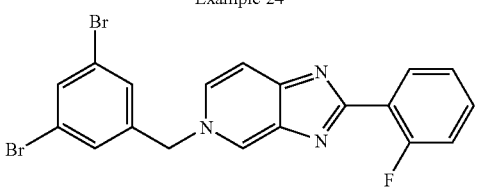 | 90 | 461.134 | 462.134 | A |

-continued

| Structures | Purity | MW | Obs. MW | Method |
|---|---|---|---|---|
| Example 25 | 90 | 401.404 | 402.404 | A |
| Example 26 | 95 | 371.377 | 372.377 | A |
| Example 27 | 95 | 439.375 | 440.375 | A |
| Example 28 | 90 | 405.822 | 406.822 | A |

-continued
| Structures | Purity | MW | Obs. MW | Method |
|---|---|---|---|---|
| Example 29 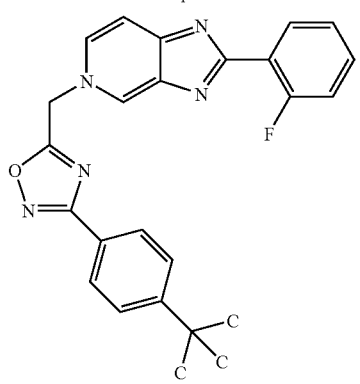 | 90 | 427.485 | 428.485 | A |
| Example 30 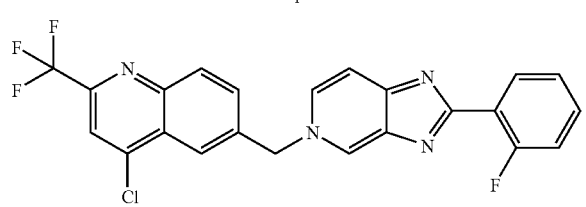 | 85 | 456.833 | 457.833 | A |
| Example 31 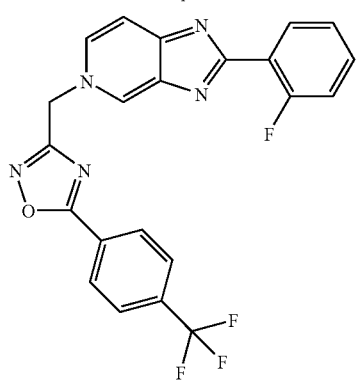 | 95 | 439.375 | 440.375 | A |
| Example 32 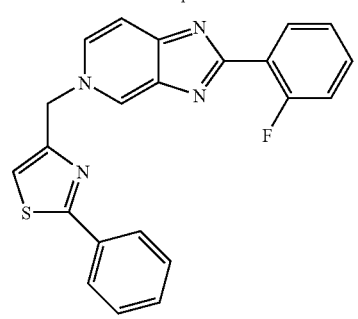 | 90 | 386.454 | 387.454 | A |

-continued

| Structures | Purity | MW | Obs. MW | Method |
|---|---|---|---|---|
| Example 33 | 90 | 392.480 | 393.480 | A |
| Example 34 | 95 | 361.301 | 362.301 | A |
| Example 35 | 92 | 369.804 | 370.804 | A |
| Example 36 | 90 | 405.785 | 406.785 | A |
| Example 37 | 92 | 421.785 | 422.785 | A |
| Example 38 | 90 | 401.367 | 402.367 | A |

-continued

| Structures | Purity | MW | Obs. MW | Method |
|---|---|---|---|---|
| Example 39 | 90 | 351.814 | 352.814 | A |
| Example 40 | 92 | 423.812 | 424.812 | A |
| Example 41 | 98 | 339.391 | 340.391 | A |
| Example 42 | 92 | 449.408 | 450.408 | A |
| Example 43 | 95 | 422.825 | 423.825 | A |

-continued

| Structures | Purity | MW | Obs. MW | Method |
|---|---|---|---|---|
| Example 44 | 93 | 388.380 | 389.380 | A |
| Example 45 | 95 | 479.124 | 480.124 | A |
| Example 46 | 97 | 419.394 | 420.394 | A |
| Example 47 | 94 | 389.367 | 390.367 | A |

-continued

| Structures | Purity | MW | Obs. MW | Method |
|---|---|---|---|---|
| Example 48 | 92 | 457.366 | 458.366 | A |
| Example 49 | 90 | 363.778 | 364.778 | A |
| Example 50 | 92 | 445.476 | 446.476 | A |
| Example 51 | 95 | 457.366 | 458.366 | A |

-continued
| Structures | Purity | MW | Obs. MW | Method |
|---|---|---|---|---|
| Example 52 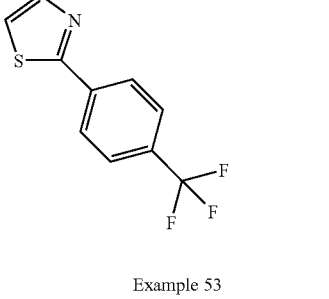 | 95 | 472.443 | 473.443 | A |
| Example 53 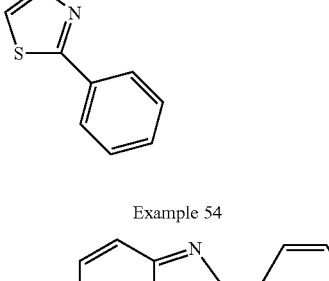 | 95 | 404.444 | 405.444 | A |
| Example 54 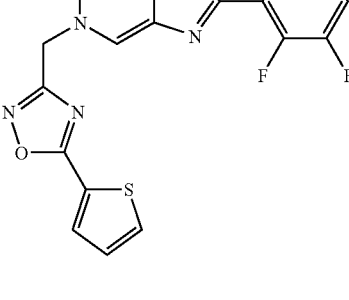 | 95 | 395.393 | 396.393 | A |
| Example 55 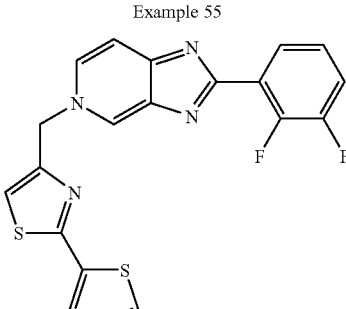 | 90 | 410.470 | 411.470 | A |

-continued

| Structures | Purity | MW | Obs. MW | Method |
|---|---|---|---|---|
| Example 56 | 92 | 457.329 | 458.329 | A |
| Example 57 | 93 | 353.350 | 354.350 | A |
| Example 58 | 95 | 423.776 | 424.776 | A |
| Example 59 | 95 | 439.775 | 440.775 | A |
| Example 60 | 92 | 419.357 | 420.357 | A |
| Example 61 | 90 | 390.222 | 391.222 | A |
| Example 62 | 90 | 405.330 | 406.330 | A |

-continued
| Structures | Purity | MW | Obs. MW | Method |
|---|---|---|---|---|
| Example 63 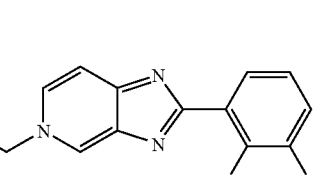 | 90 | 431.421 | 432.421 | A |
| Example 64 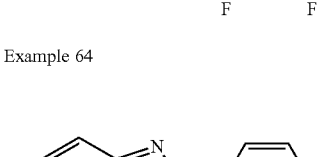 | 0 | 422.441 | 423.441 | A |
| Example 65 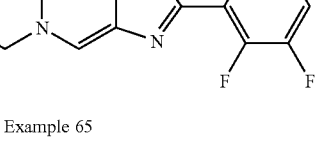 | 90 | 425.442 | 426.442 | A |
| Example 66 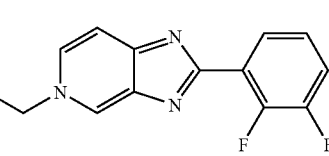 | 95 | 431.876 | 432.876 | C |
| Example 67 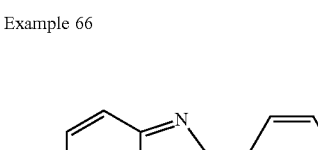 | 95 | 442.429 | 443.429 | C |
| Example 68 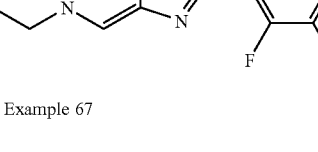 | 95 | 411.458 | 412.458 | C |

-continued

| Structures | Purity | MW | Obs. MW | Method |
|---|---|---|---|---|
| Example 69 | 95 | 411.458 | 412.458 | C |
| Example 70 | 95 | 411.458 | 412.458 | C |
| Example 71 | 95 | 415.422 | 416.422 | C |
| Example 72 | 95 | 403.457 | 404.457 | C |
| Example 73 | 90 | 441.485 | 442.485 | C |
| Example 74 | 95 | 465.430 | 466.430 | C |

-continued
| Structures | Purity | MW | Obs. MW | Method |
|---|---|---|---|---|
| Example 75 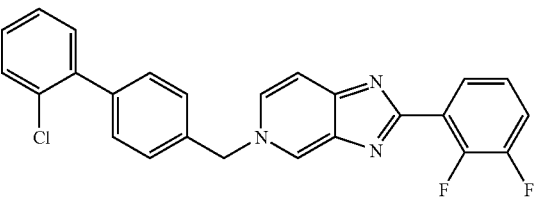 | 95 | 431.876 | 432.876 | C |
| Example 76 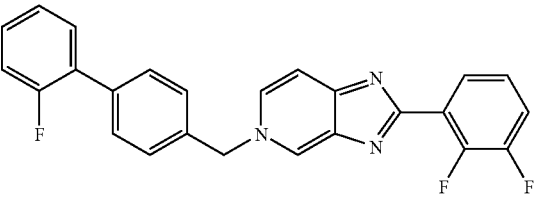 | 95 | 415.422 | 416.422 | C |
| Example 77 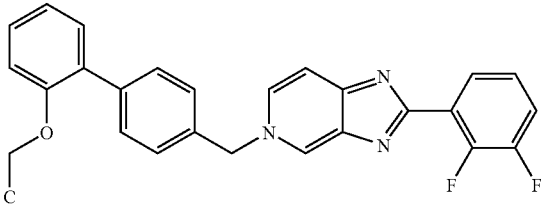 | 95 | 441.485 | 442.485 | C |
| Example 78 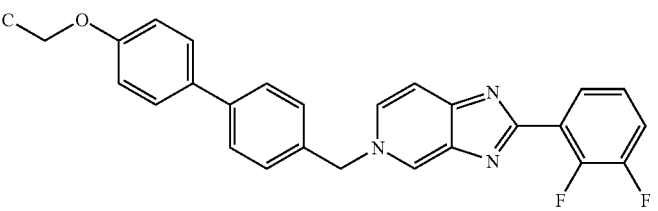 | 95 | 441.485 | 442.485 | C |
| Example 79 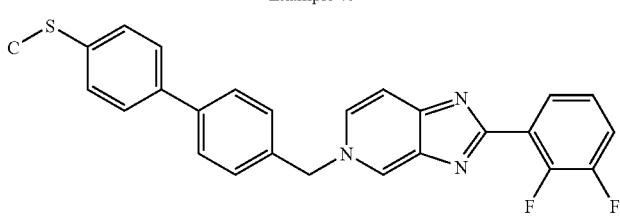 | 95 | 443.522 | 444.522 | C |
| Example 80 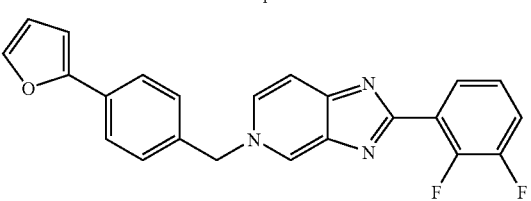 | 95 | 387.392 | 388.392 | C |

-continued

| Structures | Purity | MW | Obs. MW | Method |
|---|---|---|---|---|
| Example 81 | 95 | 433.412 | 434.412 | C |
| Example 82 | 95 | 439.469 | 440.469 | C |
| Example 83 | 95 | 439.469 | 440.469 | C |
| Example 84 | 95 | 425.485 | 426.485 | C |
| Example 85 | 95 | 465.430 | 466.430 | C |

-continued
| Structures | Purity | MW | Obs. MW | Method |
|---|---|---|---|---|
| Example 86 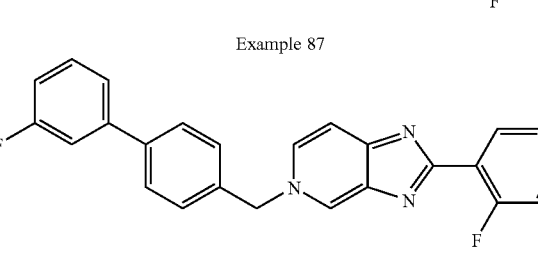 | 95 | 465.430 | 466.430 | C |
| Example 87 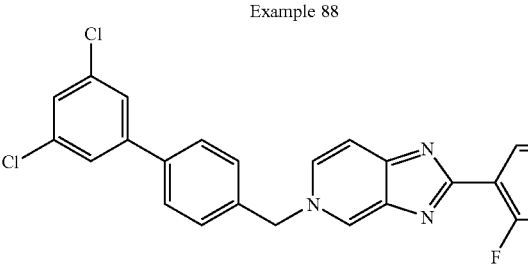 | 95 | 415.422 | 416.422 | C |
| Example 88 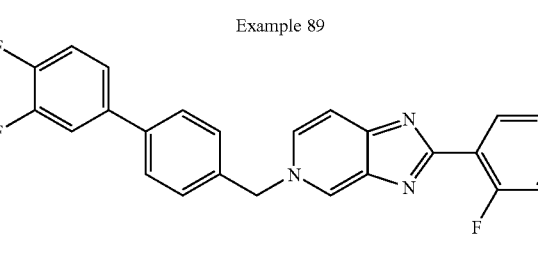 | 95 | 466.321 | 467.321 | C |
| Example 89 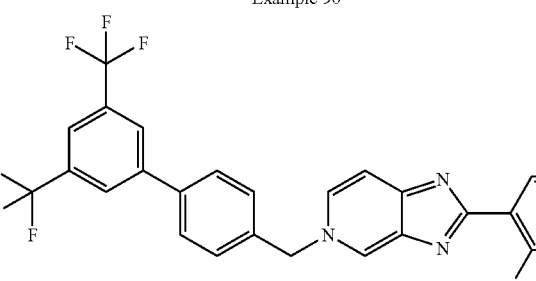 | 95 | 433.412 | 434.412 | C |
| Example 90 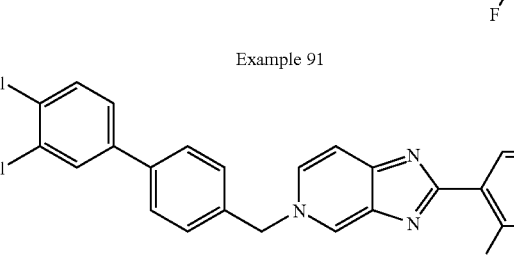 | 95 | 533.428 | 534.428 | C |
| Example 91 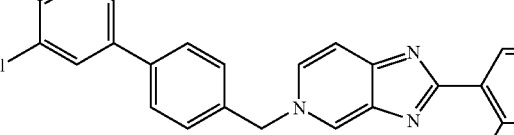 | 95 | 466.321 | 467.321 | C |

-continued

| Structures | Purity | MW | Obs. MW | Method |
|---|---|---|---|---|
| Example 92 | 90 | 425.485 | 426.485 | C |
| Example 93 | 90 | 457.484 | 458.484 | C |
| Example 94 | 90 | 447.492 | 448.492 | C |
| Example 95 | 90 | 489.529 | 490.529 | C |
| Example 96 | 90 | 457.484 | 458.484 | C |
| Example 97 | 90 | 425.485 | 426.485 | C |

-continued

| Structures | Purity | MW | Obs. MW | Method |
|---|---|---|---|---|
| Example 98 | 90 | 425.485 | 426.485 | C |
| Example 99 | 90 | 440.500 | 441.500 | C |
| Example 100 | 90 | 429.449 | 430.449 | C |
| Example 101 | 90 | 437.902 | 438.902 | C |
| Example 102 | 90 | 437.453 | 438.453 | C |
| Example 103 | 90 | 453.517 | 454.517 | C |

-continued

| Structures | Purity | MW | Obs. MW | Method |
|---|---|---|---|---|
| Example 104 | 90 | 481.429 | 482.429 | C |
| Example 105 | 90 | 481.429 | 482.429 | C |
| Example 106 | 90 | 453.517 | 454.517 | C |
| Example 107 | 90 | 449.867 | 450.867 | C |
| Example 108 | 90 | 466.321 | 467.321 | C |

-continued

| Structures | Purity | MW | Obs. MW | Method |
|---|---|---|---|---|
| Example 109 | 90 | 422.441 | 423.441 | C |
| Example 110 | 90 | 433.412 | 434.412 | C |
| Example 111 | 90 | 442.429 | 443.429 | C |
| Example 112 | 90 | 427.458 | 428.458 | C |
| Example 113 | 90 | 427.458 | 428.458 | C |
| Example 114 | 90 | 425.485 | 426.485 | C |

-continued

| Structures | Purity | MW | Obs. MW | Method |
|---|---|---|---|---|
| Example 115 | 90 | 439.512 | 440.512 | C |
| Example 116 | 90 | 466.321 | 467.321 | C |
| Example 117 | 90 | 503.556 | 504.556 | C |
| Example 118 | 90 | 443.522 | 444.522 | C |
| Example 119 | 90 | 422.441 | 423.441 | C |
| Example 120 | 90 | 475.521 | 476.521 | C |

-continued

| Structures | Purity | MW | Obs. MW | Method |
|---|---|---|---|---|
| Example 121 | 90 | 433.412 | 434.412 | C |
| Example 122 | 90 | 503.556 | 504.556 | C |
| Example 123 | 90 | 429.449 | 430.449 | C |
| Example 124 | 90 | 453.540 | 454.540 | C |
| Example 125 | 90 | 466.321 | 467.321 | C |
| Example 126 | 90 | 456.456 | 457.456 | C |

-continued

| Structures | Purity | MW | Obs. MW | Method |
|---|---|---|---|---|
| Example 127 | 90 | 481.429 | 482.429 | C |
| Example 128 | 90 | 483.522 | 484.522 | C |
| Example 129 | 90 | 445.448 | 446.448 | C |
| Example 130 | 90 | 392.870 | 393.870 | A |
| Example 131 | 90 | 358.425 | 359.425 | A |
| Example 132 | 90 | 392.486 | 393.486 | A |
| Example 133 | 90 | 453.540 | 454.540 | C |

-continued

| Structures | Purity | MW | Obs. MW | Method |
|---|---|---|---|---|
| Example 134 | 90 | 546.582 | 547.582 | C |
| Example 135 | 90 | 445.448 | 446.448 | C |
| Example 136 | 0 | 456.378 | 457.378 | A |
| Example 137 | 95 | 472.378 | 473.378 | A |
| Example 138 | 95 | 423.812 | 424.812 | A |

-continued
| Structures | Purity | MW | Obs. MW | Method |
|---|---|---|---|---|
| Example 139 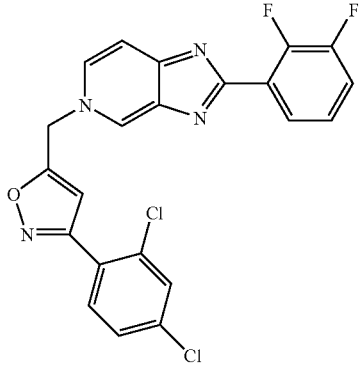 | 99 | 457.270 | 458.270 | D |
| Example 140 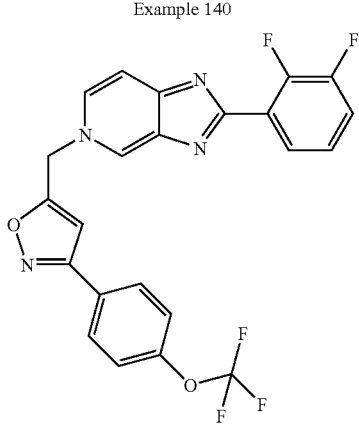 | 98 | 472.378 | 473.378 | D |
| Example 141 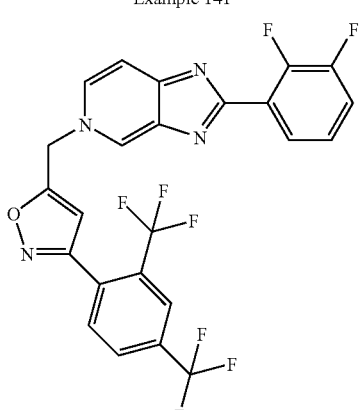 | 98 | 524.377 | 525.377 | D |

-continued
| Structures | Purity | MW | Obs. MW | Method |
|---|---|---|---|---|
| Example 142 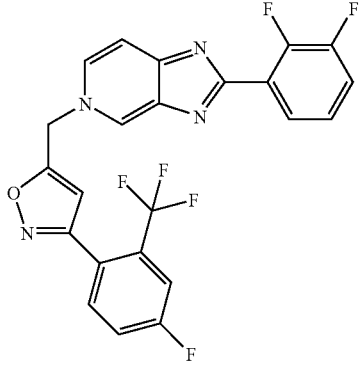 | 0 | 474.369 | 475.369 | D |
| Example 143 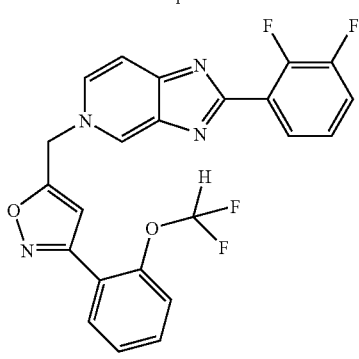 | 99 | 454.387 | 455.387 | D |
| Example 144 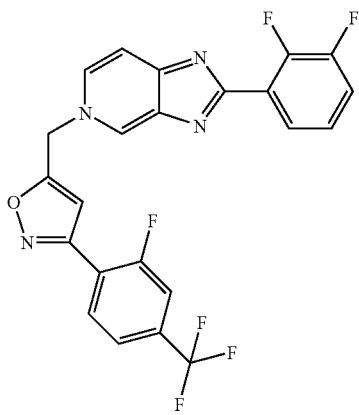 | 98 | 474.369 | 475.369 | D |

-continued

| Structures | Purity | MW | Obs. MW | Method |
|---|---|---|---|---|
| Example 145 | 98 | 485.266 | 486.266 | D |
| Example 146 | 95 | 442.351 | 443.351 | D |
| Example 147 | 90 | 420.397 | 421.397 | D |
| Example 148 | 90 | 402.407 | 403.407 | D |

-continued
| Structures | Purity | MW | Obs. MW | Method |
|---|---|---|---|---|
| Example 149 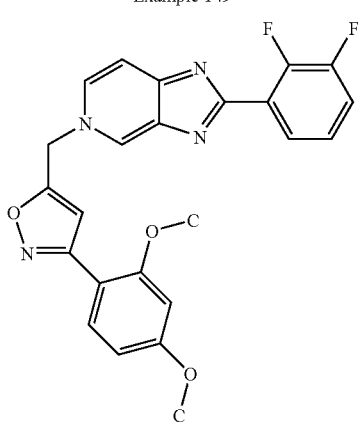 | 98 | 448.433 | 449.433 | D |
| Example 150 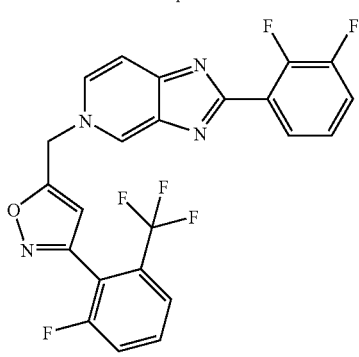 | 98 | 474.369 | 475.369 | D |
| Example 151 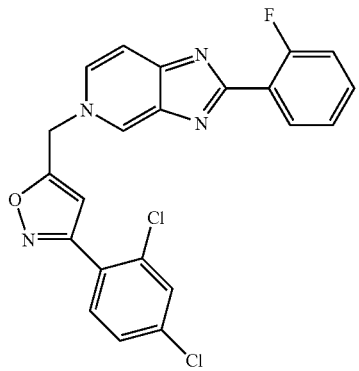 | 96 | 439.280 | 440.280 | D |

-continued
| Structures | Purity | MW | Obs. MW | Method |
|---|---|---|---|---|
| Example 152 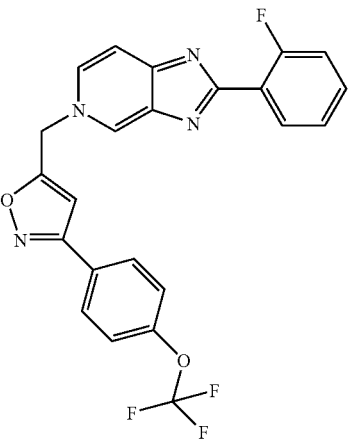 | 98 | 454.387 | 455.387 | D |
| Example 153 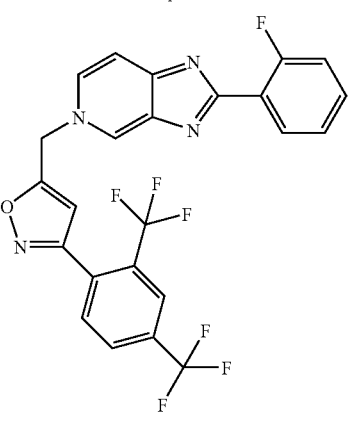 | 98 | 506.386 | 507.386 | D |
| Example 154 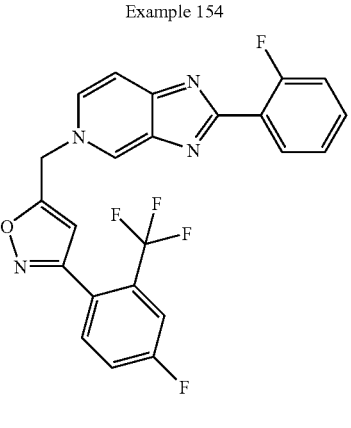 | 98 | 456.378 | 457.378 | D |

-continued

| Structures | Purity | MW | Obs. MW | Method |
|---|---|---|---|---|
| Example 155 | 98 | 436.397 | 437.397 | D |
| Example 156 | 98 | 456.378 | 457.378 | D |
| Example 157 | 98 | 467.276 | 468.276 | D |

-continued
| Structures | Purity | MW | Obs. MW | Method |
|---|---|---|---|---|
| Example 158 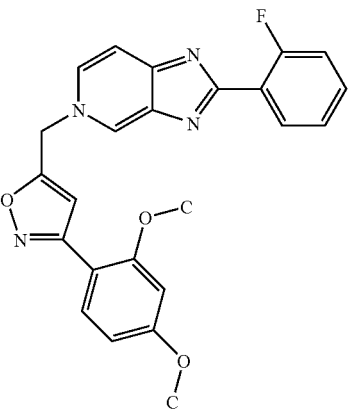 | 98 | 430.442 | 431.442 | D |
| Example 159 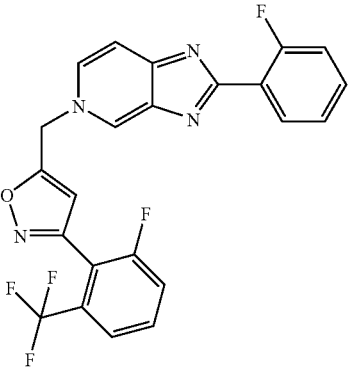 | 98 | 456.378 | 457.378 | D |
| Example 160 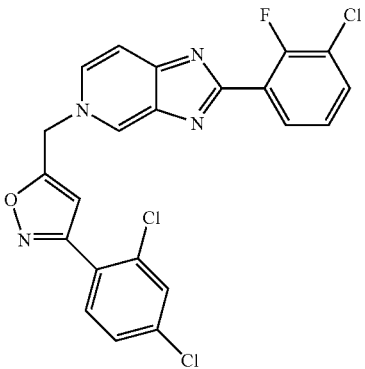 | 85 | 473.725 | 474.725 | D |

-continued
| Structures | Purity | MW | Obs. MW | Method |
|---|---|---|---|---|
| Example 161 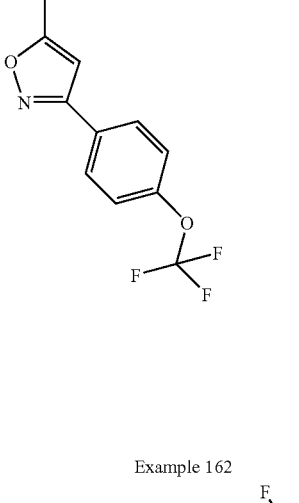 | 98 | 488.832 | 489.832 | D |
| Example 162 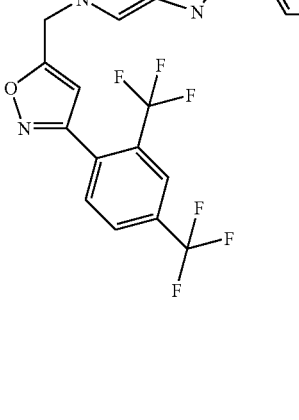 | 98 | 540.831 | 541.831 | D |
| Example 163 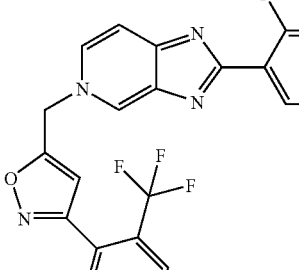 | 98 | 490.823 | 491.823 | D |

-continued
| Structures | Purity | MW | Obs. MW | Method |
|---|---|---|---|---|
| Example 164 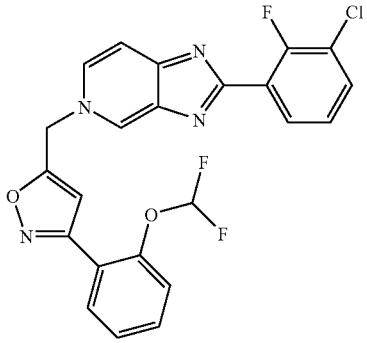 | 98 | 470.842 | 471.842 | D |
| Example 165 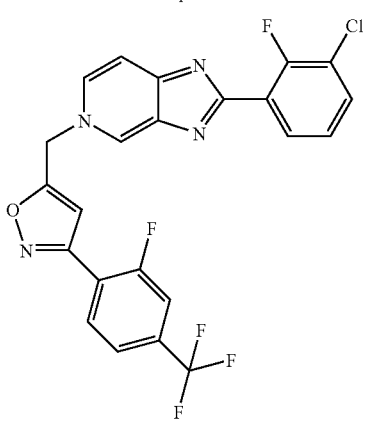 | 98 | 490.823 | 491.823 | D |
| Example 166 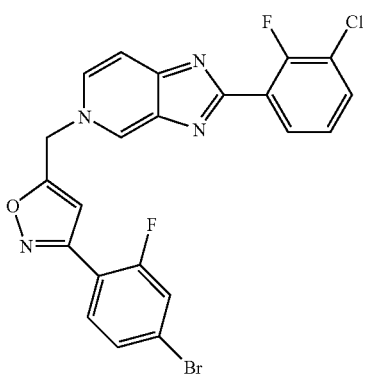 | 98 | 501.721 | 502.721 | D |
| Example 167 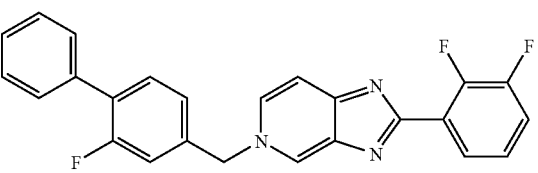 | 90 | 415.422 | 416.422 | C |

| Structures | Purity | MW | Obs. MW | Method |
|---|---|---|---|---|
| Example 168 | 90 | 483.420 | 484.420 | C |
| Example 169 | 90 | 499.419 | 500.419 | C |
| Example 170 | 90 | 445.448 | 446.448 | C |
| Example 171 | 90 | 461.513 | 462.513 | C |
| Example 172 | 90 | 451.402 | 452.402 | C |
| Example 173 | 90 | 465.430 | 466.430 | C |

-continued

| Structures | Purity | MW | Obs. MW | Method |
|---|---|---|---|---|
| Example 174 | 90 | 481.429 | 482.429 | C |
| Example 175 | 90 | 427.458 | 428.458 | C |
| Example 176 | 90 | 443.522 | 444.522 | C |
| Example 177 | 90 | 433.412 | 434.412 | C |
| Example 178 | 90 | 431.876 | 432.876 | C |
| Example 179 | 90 | 515.874 | 516.874 | C |
| Example 180 | 90 | 461.903 | 462.903 | C |

-continued
| Structures | Purity | MW | Obs. MW | Method |
|---|---|---|---|---|
| Example 181 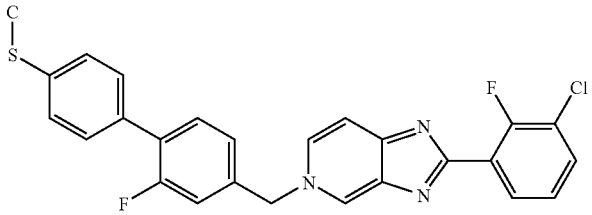 | 90 | 477.967 | 478.967 | C |
| Example 182 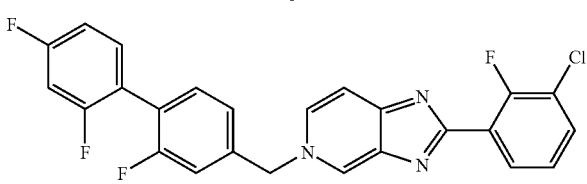 | 90 | 467.857 | 468.857 | C |
| Example 183 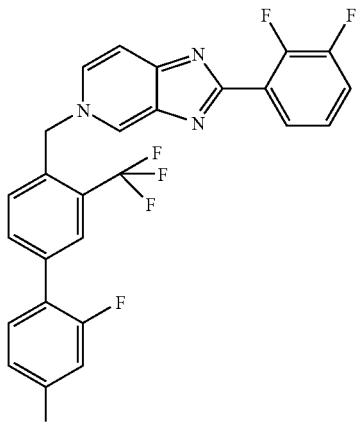 | 90 | 501.410 | 502.410 | C |
| Example 184 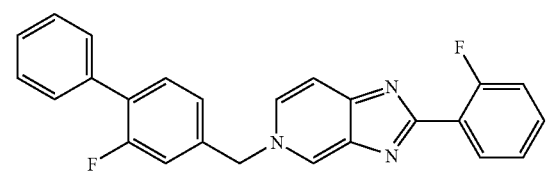 | 90 | 397.431 | 398.431 | C |
| Example 185 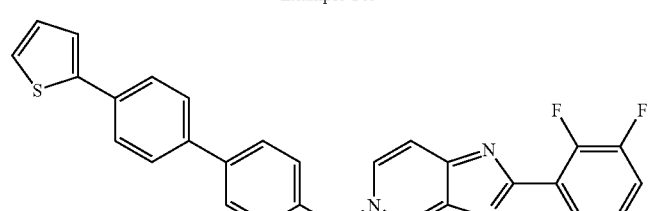 | 95 | 479.556 | 480.556 | E |

-continued

| Structures | Purity | MW | Obs. MW | Method |
|---|---|---|---|---|
| Example 186 | 95 | 423.469 | 424.469 | E |
| Example 187 | 95 | 441.485 | 442.485 | E |
| Example 188 | 95 | 455.468 | 456.468 | E |
| Example 189 | 95 | 469.495 | 470.495 | E |
| Example 190 | 95 | 483.522 | 484.522 | E |
| Example 192 | 95 | 436.468 | 437.468 | E |

-continued
| Structures | Purity | MW | Obs. MW | Method |
|---|---|---|---|---|
| Example 193 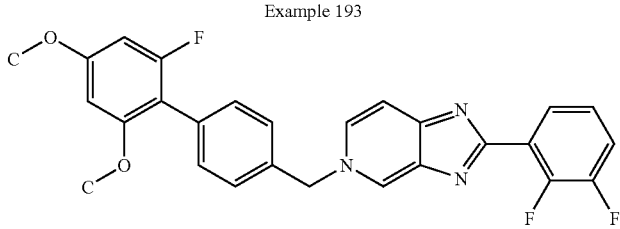 | 95 | 475.475 | 476.475 | E |
| Example 194 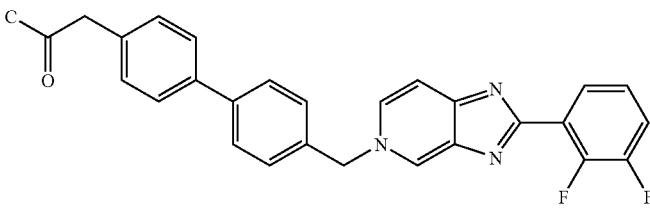 | 95 | 453.496 | 454.496 | E |
| Example 195 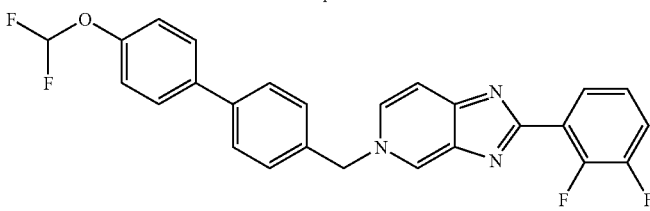 | 95 | 463.438 | 464.438 | E |
| Example 196 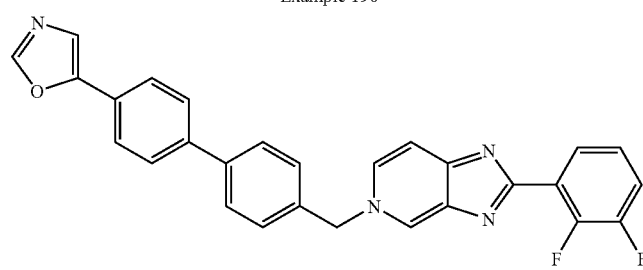 | 95 | 464.479 | 465.479 | E |
| Example 199 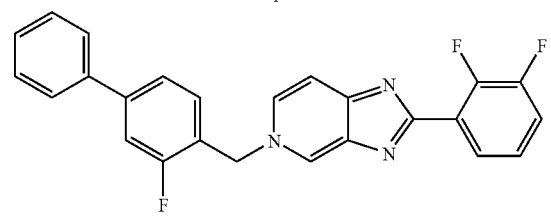 | 90 | 415.422 | 416.422 | C |
| Example 200 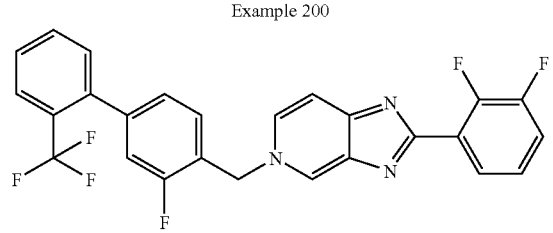 | 90 | 483.420 | 484.420 | C |

-continued

| Structures | Purity | MW | Obs. MW | Method |
|---|---|---|---|---|
| Example 201 | 90 | 499.419 | 500.419 | C |
| Example 202 | 90 | 445.448 | 446.448 | C |
| Example 203 | 90 | 461.513 | 462.513 | C |
| Example 204 | 90 | 451.402 | 452.402 | C |
| Example 205 | 90 | 397.431 | 398.431 | C |
| Example 206 | 90 | 465.430 | 466.430 | C |

-continued

| Structures | Purity | MW | Obs. MW | Method |
|---|---|---|---|---|
| Example 207 | 90 | 481.429 | 482.429 | C |
| Example 208 | 90 | 427.458 | 428.458 | C |
| Example 209 | 90 | 443.522 | 444.522 | C |
| Example 210 | 90 | 433.412 | 434.412 | C |
| Example 211 | 90 | 431.876 | 432.876 | C |
| Example 212 | 90 | 499.875 | 500.875 | C |

-continued
| Structures | Purity | MW | Obs. MW | Method |
|---|---|---|---|---|
| Example 213 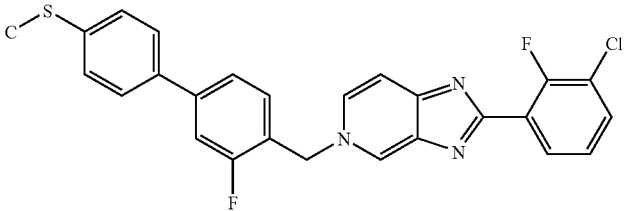 | 90 | 477.967 | 478.967 | C |
| Example 214 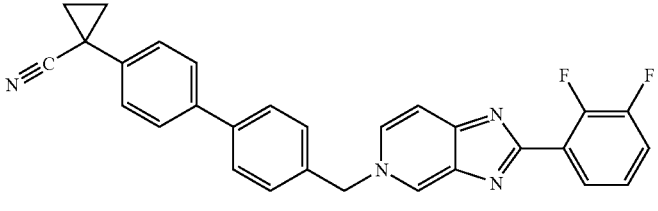 | 95 | 462.506 | 463.506 | E |
| Example 215 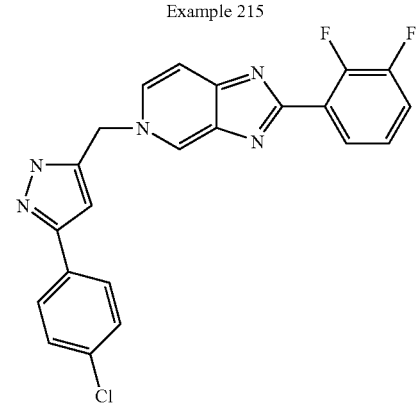 | 95 | 421.840 | 422.840 | A |
| Example 216 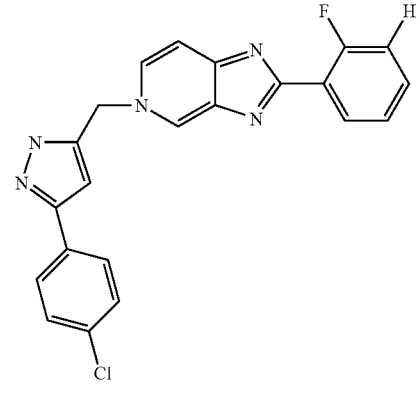 | 95 | 403.850 | 404.850 | A |

| Structures | Purity | MW | Obs. MW | Method |
|---|---|---|---|---|
| Example 217 | 95 | 417.422 | 418.422 | A |
| Example 218 | 95 | 399.431 | 400.431 | A |
| Example 219 | 95 | 434.400 | 435.400 | A |
| Example 220 | 95 | 416.409 | 417.409 | A |

-continued
| Structures | Purity | MW | Obs. MW | Method |
|---|---|---|---|---|
| Example 221 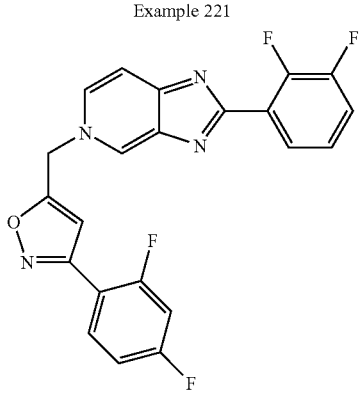 | 98 | 424.361 | 425.361 | D |
| Example 222 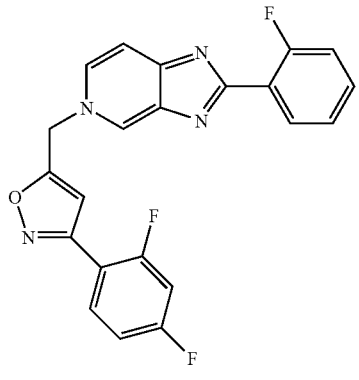 | 85 | 406.370 | 407.370 | D |
| Example 223 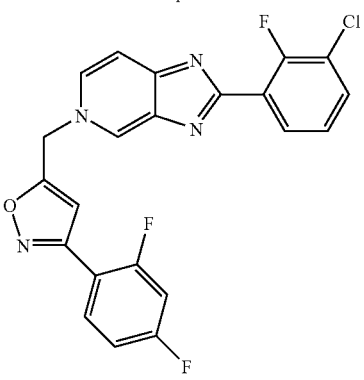 | 98 | 440.815 | 441.815 | D |
| Example 224 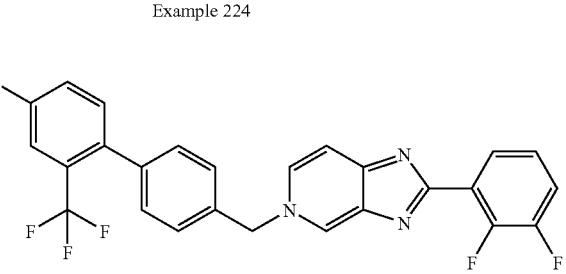 | 90 | 553.493 | 554.493 | F |

-continued

| Structures | Purity | MW | Obs. MW | Method |
|---|---|---|---|---|
| Example 225 | 90 | 567.520 | 568.520 | F |
| Example 226 | 90 | 579.575 | 580.575 | F |
| Example 227 | 84 | 551.521 | 552.521 | F |
| Example 228 | 100 | 537.537 | 538.537 | F |
| Example 229 | 92 | 551.564 | 552.564 | F |

-continued

| Structures | Purity | MW | Obs. MW | Method |
|---|---|---|---|---|
| Example 230 | 100 | 593.646 | 594.646 | F |
| Example 231 | 81 | 567.520 | 568.520 | F |
| Example 232 | 78 | 539.510 | 540.510 | F |
| Example 233 | 77 | 583.563 | 584.563 | F |
| Example 234 | 85 | 549.548 | 550.548 | F |
| Example 235 | 85 | 579.531 | 580.531 | F |

-continued

| Structures | Purity | MW | Obs. MW | Method |
|---|---|---|---|---|
| Example 236 | 82 | 593.558 | 594.558 | F |
| Example 237 | 90 | 535.521 | 536.521 | F |
| Example 238 | 85 | 551.564 | 552.564 | F |
| Example 239 | 85 | 595.574 | 596.574 | F |
| Example 240 | 80 | 551.564 | 552.564 | F |
| Example 241 | 85 | 535.521 | 536.521 | F |

-continued

| Structures | Purity | MW | Obs. MW | Method |
|---|---|---|---|---|
| Example 242 | 85 | 577.603 | 578.603 | F |
| Example 243 | 100 | 595.574 | 596.574 | F |
| Example 244 | 83 | 533.505 | 534.505 | F |
| Example 245 | 90 | 487.529 | 488.529 | F |
| Example 246 | 90 | 501.556 | 502.556 | F |

-continued
| Structures | Purity | MW | Obs. MW | Method |
|---|---|---|---|---|
| Example 247 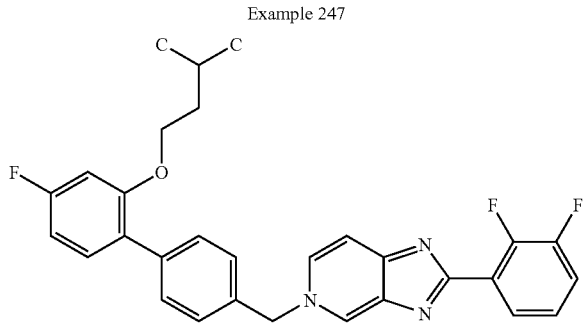 | 90 | 501.556 | 502.556 | F |
| Example 248 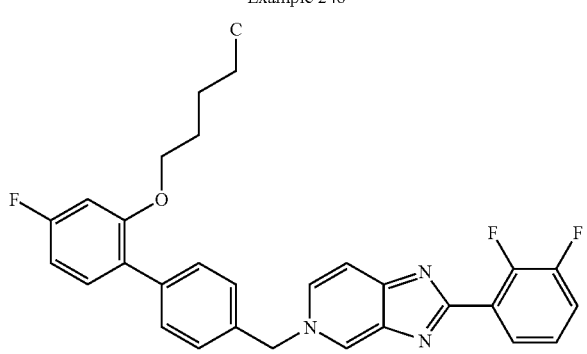 | 90 | 501.556 | 502.556 | F |
| Example 249 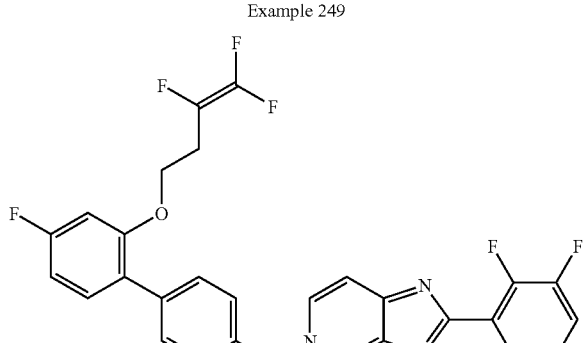 | 90 | 539.485 | 540.485 | F |
| Example 250 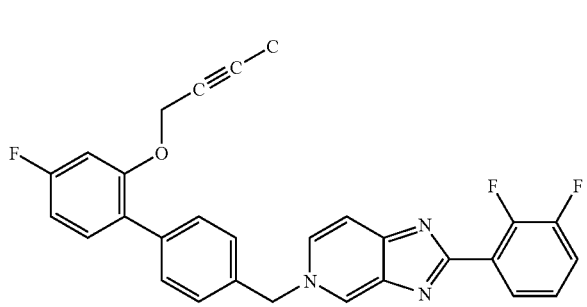 | 90 | 483.497 | 484.497 | F |

-continued
| Structures | Purity | MW | Obs. MW | Method |
|---|---|---|---|---|
| Example 251 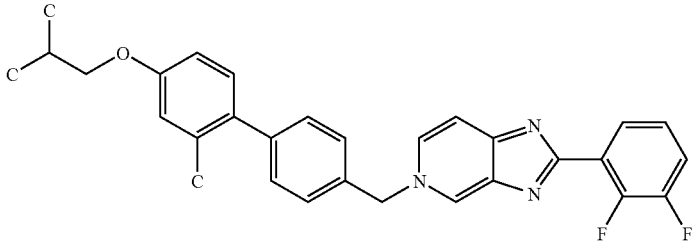 | 90 | 483.566 | 484.566 | F |
| Example 252 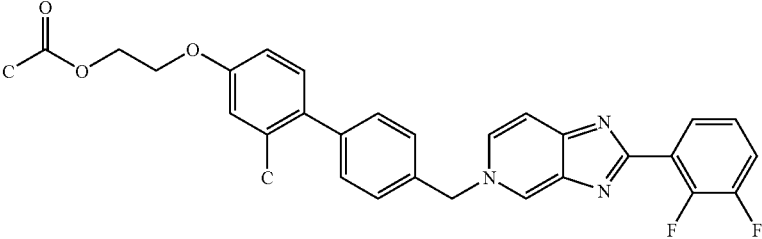 | 90 | 513.549 | 514.549 | F |
| Example 253 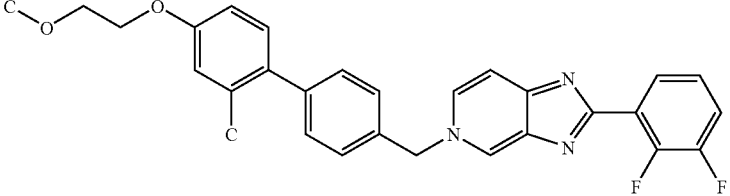 | 90 | 485.538 | 486.538 | F |
| Example 254 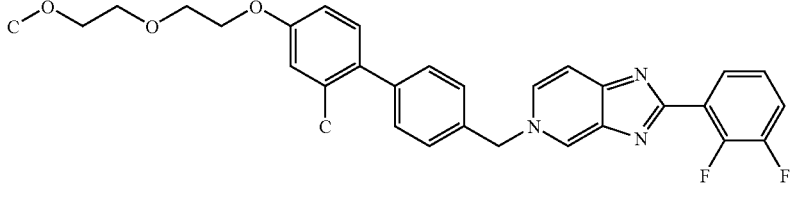 | 90 | 529.592 | 530.592 | F |
| Example 255 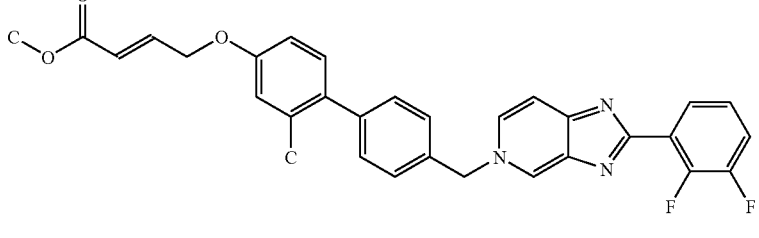 | 90 | 525.560 | 526.560 | F |
| Example 256 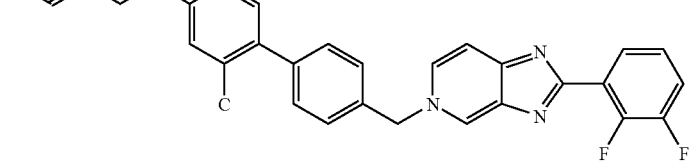 | 90 | 481.550 | 482.550 | F |

-continued
| Structures | Purity | MW | Obs. MW | Method |
|---|---|---|---|---|
| Example 257 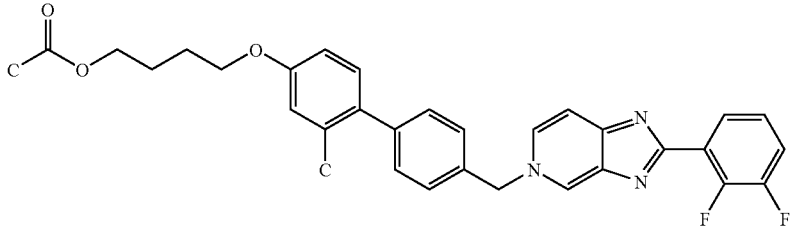 | 90 | 541.603 | 542.603 | F |
| Example 258 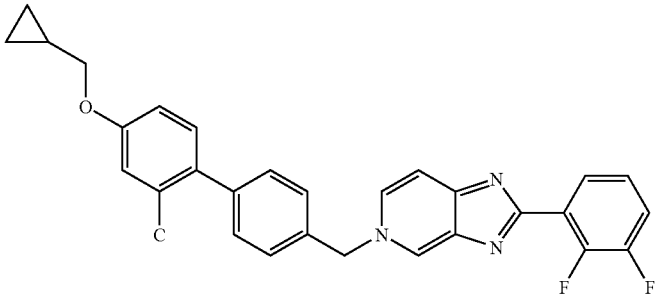 | 90 | 481.550 | 482.550 | F |
| Example 259 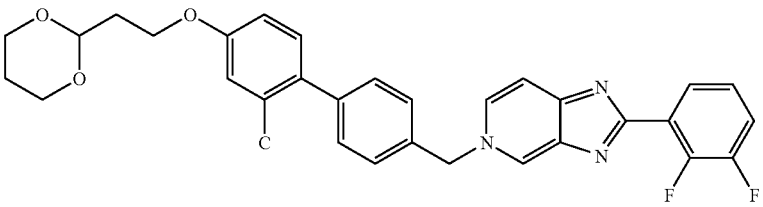 | 90 | 541.603 | 542.603 | F |
| Example 260 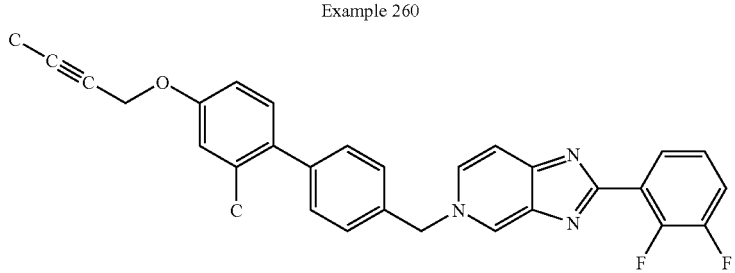 | 90 | 479.534 | 480.534 | F |
| Example 261 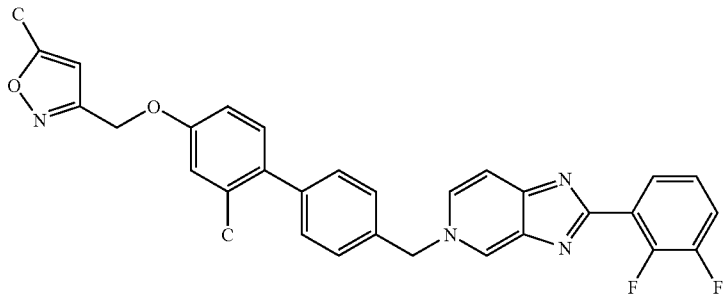 | 90 | 522.559 | 523.559 | F |

| Structures | Purity | MW | Obs. MW | Method |
|---|---|---|---|---|
| Example 262 | 90 | 469.539 | 470.539 | F |
| Example 263 | 90 | 471.511 | 472.511 | F |
| Example 264 | 90 | 515.565 | 516.565 | F |
| Example 265 | 90 | 511.533 | 512.533 | F |
| Example 266 | 90 | 467.523 | 468.523 | F |
| Example 267 | 90 | 527.576 | 528.576 | F |
| Example 268 | 90 | 521.494 | 522.494 | F |

-continued

| Structures | Purity | MW | Obs. MW | Method |
|---|---|---|---|---|
| Example 269 | 80 | 465.507 | 466.507 | F |
| Example 270 | 90 | 453.496 | 454.496 | F |
| Example 271 | 90 | 470.483 | 471.483 | F |
| Example 272 | 90 | 495.577 | 496.577 | F |
| Example 273 | 90 | 481.550 | 482.550 | F |

-continued
| Structures | Purity | MW | Obs. MW | Method |
|---|---|---|---|---|
| Example 274 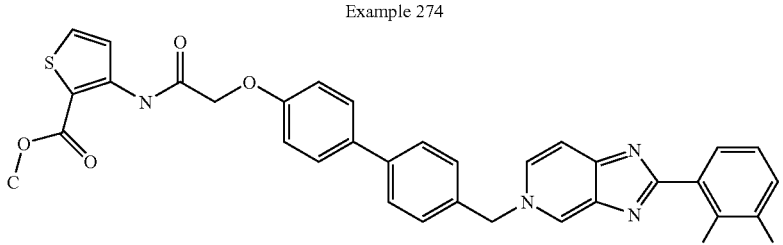 | 90 | 610.644 | 611.644 | F |
| Example 275 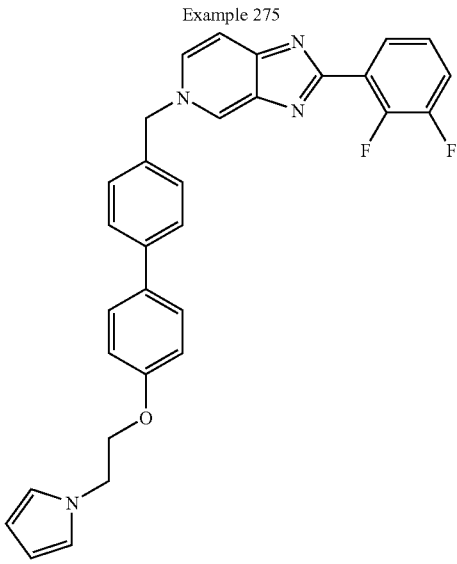 | 90 | 506.560 | 507.560 | F |
| Example 276 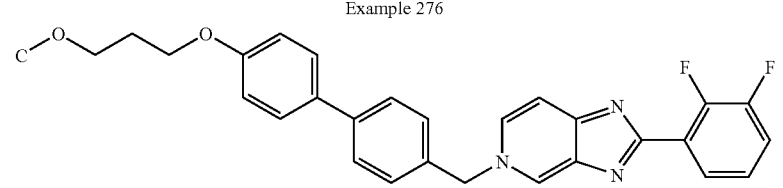 | 90 | 485.538 | 486.538 | F |
| Example 277 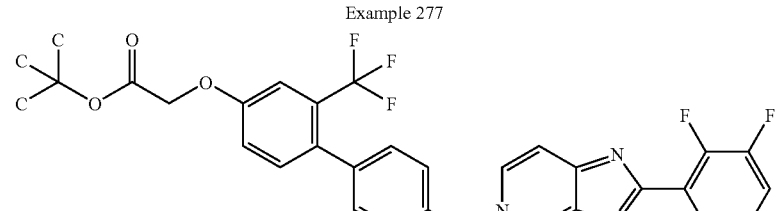 | 90 | 595.574 | 596.574 | F |
| Example 278 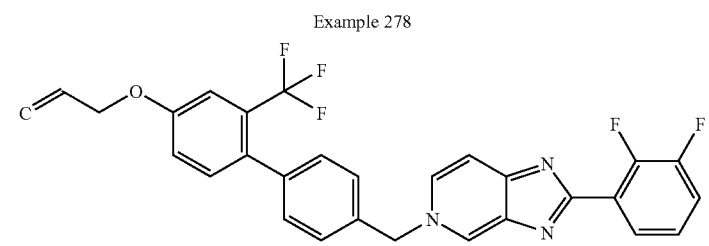 | 90 | 521.494 | 522.494 | F |

-continued

| Structures | Purity | MW | Obs. MW | Method |
|---|---|---|---|---|
| Example 279 | 90 | 538.481 | 539.481 | F |
| Example 280 | 90 | 563.576 | 564.576 | F |
| Example 281 | 85 | 565.548 | 566.548 | F |
| Example 282 | 90 | 580.606 | 581.606 | F |
| Example 283 | 90 | 549.548 | 550.548 | F |
| Example 284 | 85 | 678.643 | 679.643 | F |

-continued

| Structures | Purity | MW | Obs. MW | Method |
|---|---|---|---|---|
| Example 285 | 90 | 574.558 | 575.558 | F |
| Example 286 | 90 | 588.585 | 589.585 | F |
| Example 287 | 90 | 659.599 | 660.599 | F |
| Example 288 | 90 | 617.547 | 618.547 | F |
| Example 289 | 90 | 572.542 | 573.542 | F |

-continued
| Structures | Purity | MW | Obs. MW | Method |
|---|---|---|---|---|
| Example 290 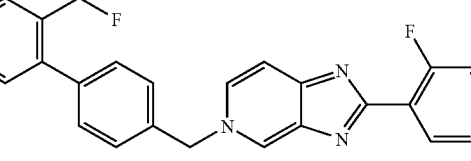 | 90 | 553.537 | 554.537 | F |
| Example 291  | 90 | 629.514 | 630.514 | F |
| Example 292 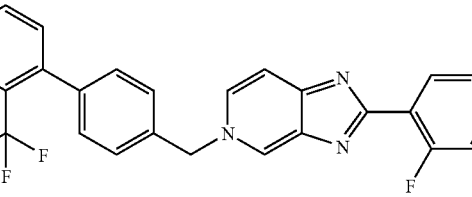 | 85 | 571.502 | 572.502 | F |
| Example 293 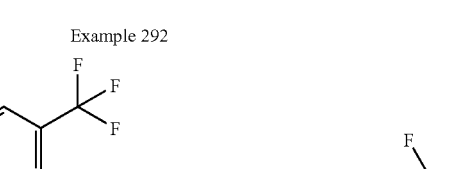 | 80 | 545.566 | 546.566 | F |
| Example 294 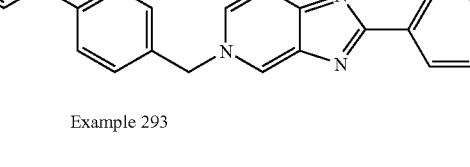 | 90 | 471.486 | 472.486 | F |

-continued

| Structures | Purity | MW | Obs. MW | Method |
|---|---|---|---|---|
| Example 295 | 90 | 488.473 | 489.473 | F |
| Example 296 | 90 | 628.635 | 629.635 | F |
| Example 297 | 90 | 524.550 | 525.550 | F |
| Example 298 | 90 | 538.577 | 539.577 | F |

-continued
| Structures | Purity | MW | Obs. MW | Method |
|---|---|---|---|---|
| Example 300 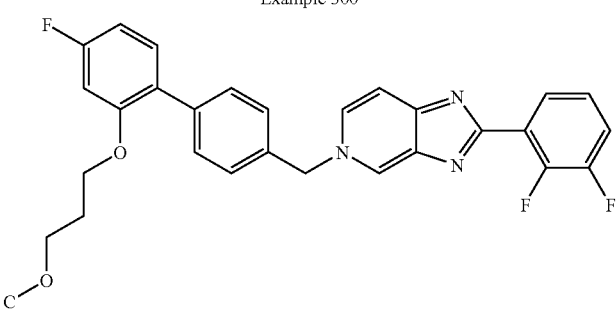 | 90 | 503.529 | 504.529 | F |
| Example 301 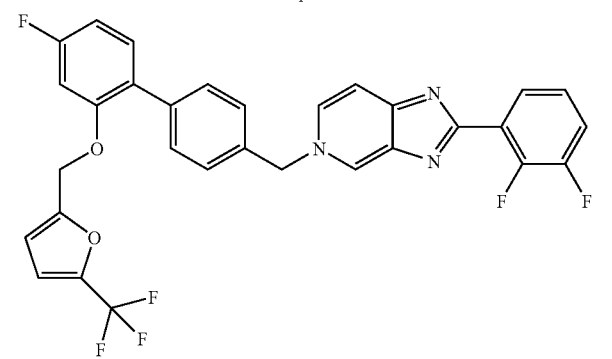 | 90 | 579.506 | 580.506 | F |
| Example 302 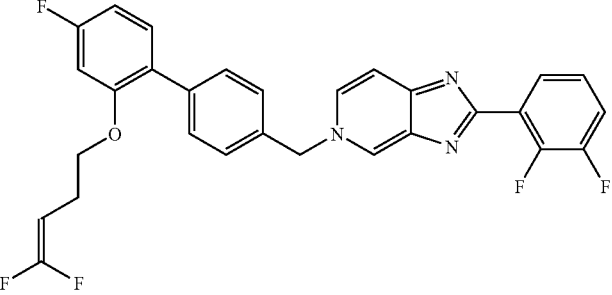 | 90 | 521.494 | 522.494 | F |
| Example 303 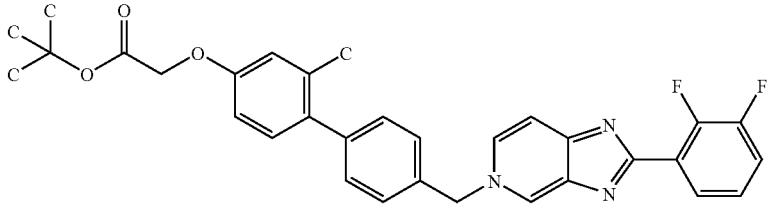 | 90 | 541.603 | 542.603 | F |
| Example 304 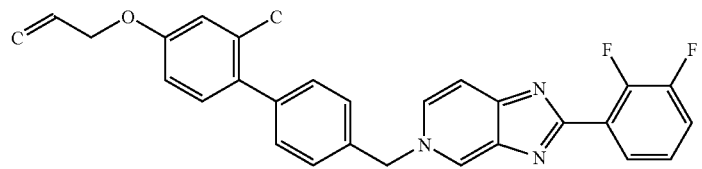 | 90 | 467.523 | 468.523 | F |

-continued

| Structures | Purity | MW | Obs. MW | Method |
|---|---|---|---|---|
| Example 305 | 90 | 483.566 | 484.566 | F |
| Example 306 | 90 | 509.604 | 510.604 | F |
| Example 307 | 90 | 511.577 | 512.577 | F |
| Example 308 | 90 | 495.577 | 496.577 | F |
| Example 309 | 90 | 520.587 | 521.587 | F |

| Structures | Purity | MW | Obs. MW | Method |
|---|---|---|---|---|
| Example 310 | 90 | 534.614 | 535.614 | F |
| Example 311 | 90 | 605.627 | 606.627 | F |
| Example 312 | 90 | 563.576 | 564.576 | F |
| Example 313 | 90 | 499.565 | 500.565 | F |
| Example 314 | 90 | 575.543 | 576.543 | F |

-continued
| Structures | Purity | MW | Obs. MW | Method |
|---|---|---|---|---|
| Example 315 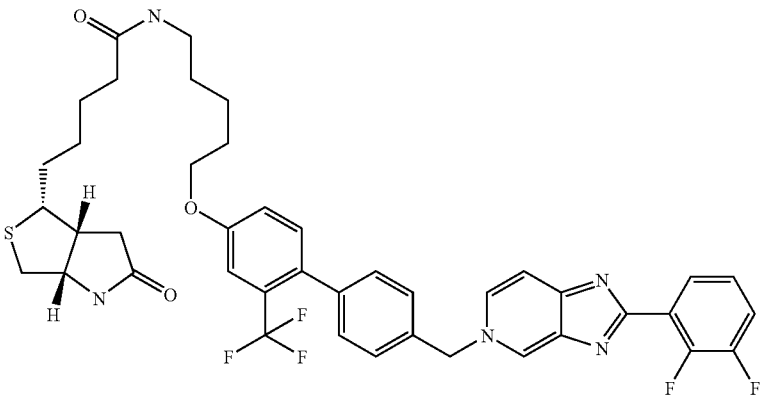 | 90 | 791.891 | 792.891 | F |
| Example 316 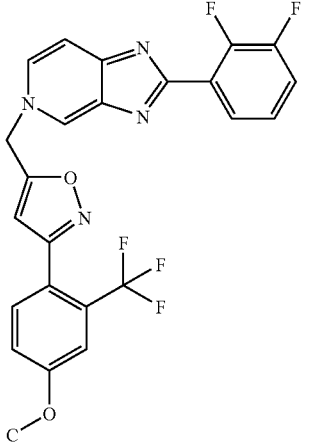 | 95 | 486.405 | 487.405 | D |
| Example 317 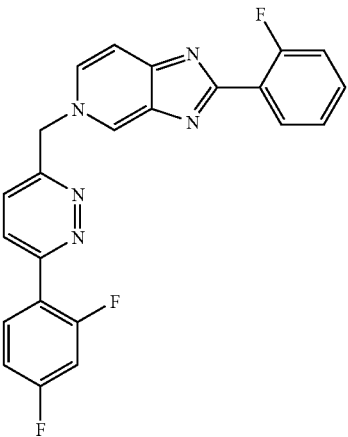 | 90 | 417.397 | 418.397 | A |

-continued

| Structures | Purity | MW | Obs. MW | Method |
|---|---|---|---|---|
| Example 318 | 90 | 396.787 | 397.787 | A |
| Example 319 | 90 | 387.34 | | A |
| Example 320 | 90 | 371.34 | | A |
| Example 321 | 90 | 400.23 | | A |

-continued
| Structures | Purity | MW | Obs. MW | Method |
|---|---|---|---|---|
| Example 322 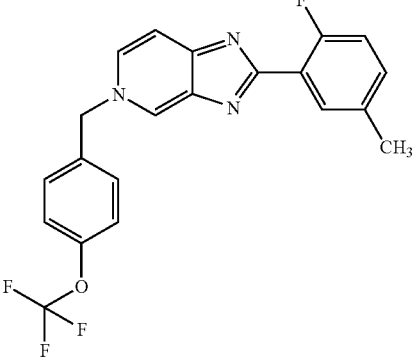 | 90 | 401.37 | | A |
| Example 323 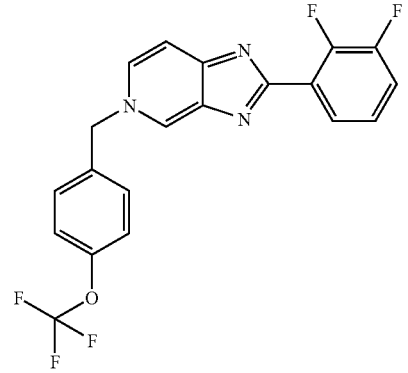 | 90 | 405.33 | | A |
| Example 324 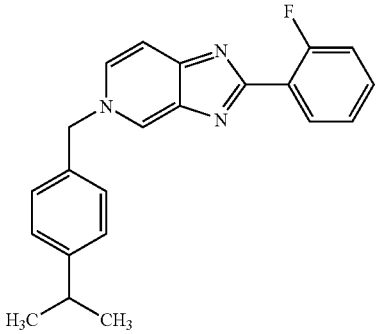 | 90 | 345.42 | | A |

-continued
| Structures | Purity | MW | Obs. MW | Method |
|---|---|---|---|---|
| Example 325 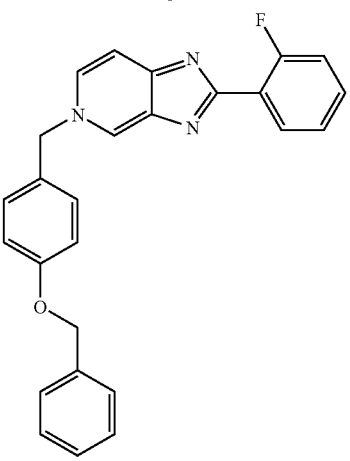 | 90 | 409.47 | | A |
| Example 326 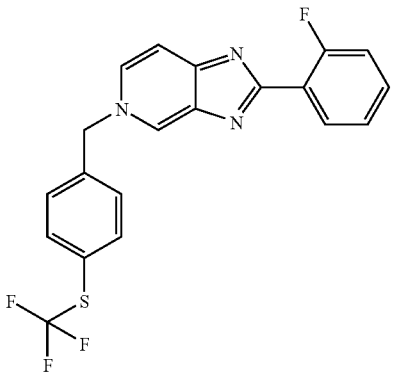 | 90 | 403.40 | | A |
| Example 327 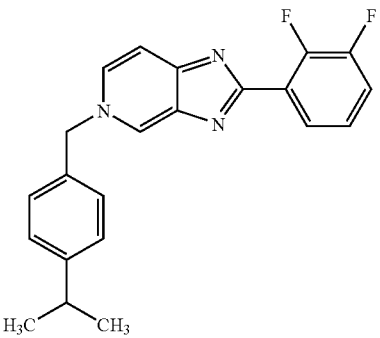 | 90 | 363.41 | | A |

-continued
| Structures | Purity | MW | Obs. MW | Method |
|---|---|---|---|---|
| Example 328 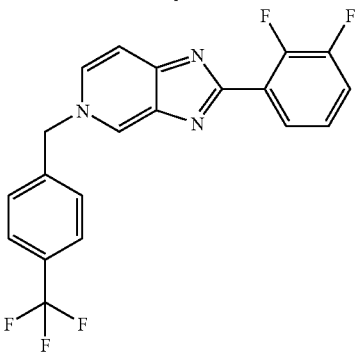 | 90 | 389.33 | | A |
| Example 329 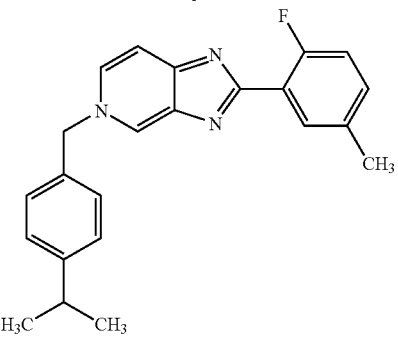 | 90 | 359.45 | | A |
| Example 330 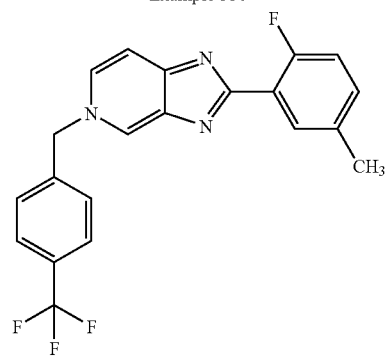 | 90 | 385.37 | | A |
| Example 331 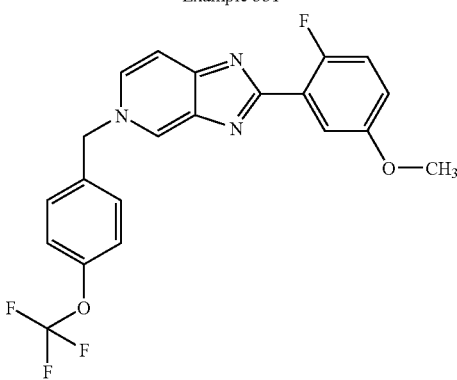 | 90 | 417.37 | | A |

-continued
| Structures | Purity | MW | Obs. MW | Method |
|---|---|---|---|---|
| Example 332 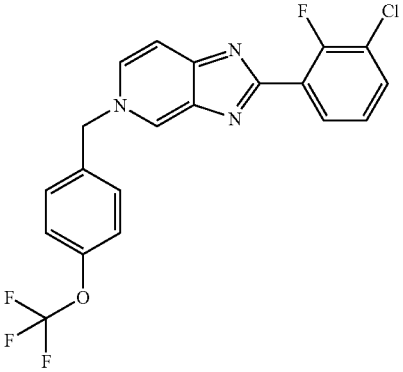 | 90 | 421.78 | | A |
| Example 333 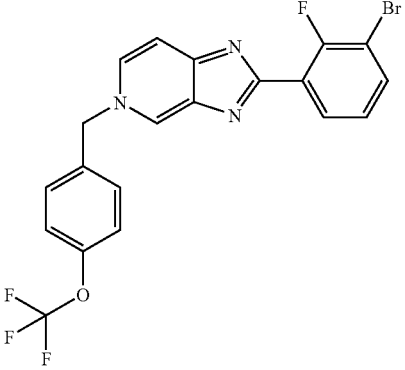 | 90 | 466.24 | | A |
| Example 334 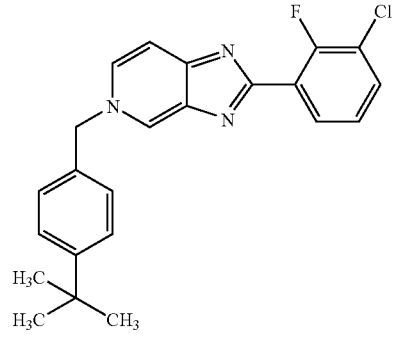 | 90 | 393.90 | | A |
| Example 335 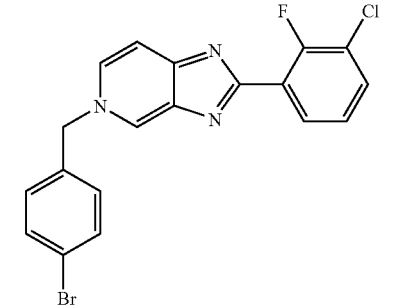 | 90 | 416.68 | | A |

-continued

| Structures | Purity | MW | Obs. MW | Method |
|---|---|---|---|---|
| Example 336 | 90 | 405.79 | | A |
| Example 337 | 90 | 463.68 | | A |
| Example 338 | 90 | 379.87 | | A |
| Example 339 | 90 | 423.81 | | |

-continued

| Structures | Purity | MW | Obs. MW | Method |
|---|---|---|---|---|
| Example 340 | 90 | 419.39 | | |
| Example 341 | 90 | 403.39 | | |
| Example 342 | 90 | 418.41 | | D |

-continued

| Structures | Purity | MW | Obs. MW | Method |
|---|---|---|---|---|
| Example 343 | 90 | 402.41 | | D |
| Example 344 | 90 | 378.34 | | D |
| Example 345 | 90 | 394.41 | | D |
| Example 346 | 90 | 431.45 | | D |

-continued
| Structures | Purity | MW | Obs. MW | Method |
|---|---|---|---|---|
| Example 347 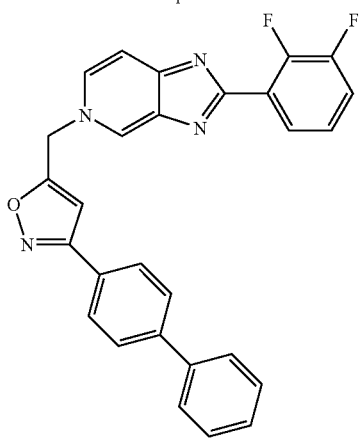 | 90 | 464.48 | | D |
| Example 348 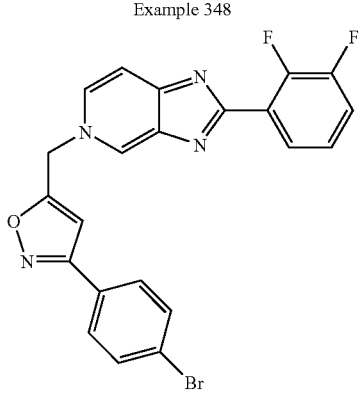 | 90 | 467.28 | | D |
| Example 349 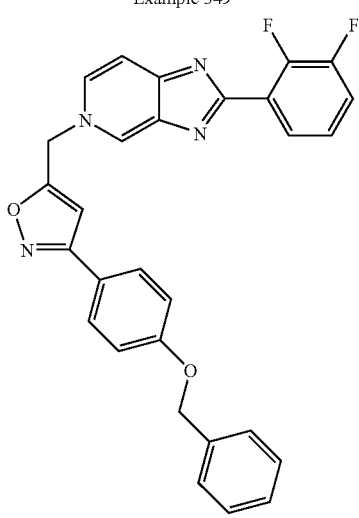 | 90 | 494.51 | | D |

-continued

| Structures | Purity | MW | Obs. MW | Method |
|---|---|---|---|---|
| Example 350 | 90 | 434.47 | | D |
| Example 351 | 90 | 432.43 | | D |
| Example 352 | 90 | 432.43 | | D |
| Example 353 | 90 | 436.40 | | D |

-continued
| Structures | Purity | MW | Obs. MW | Method |
|---|---|---|---|---|
| Example 354 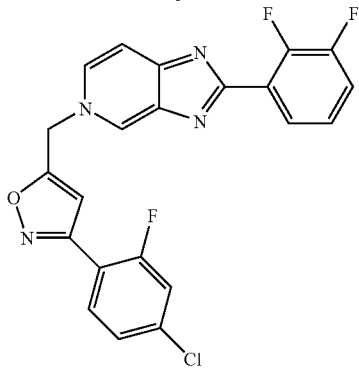 | 90 | 440.82 | | D |
| Example 355 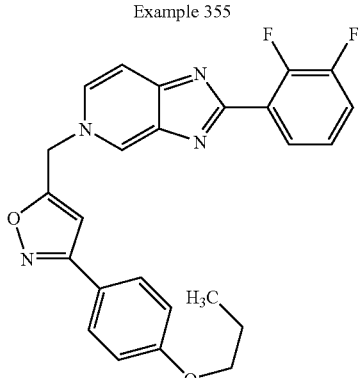 | 90 | 446.46 | | D |
| Example 356 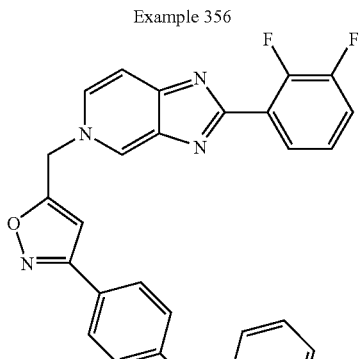 | 90 | 480.48 | | D |
| Example 357 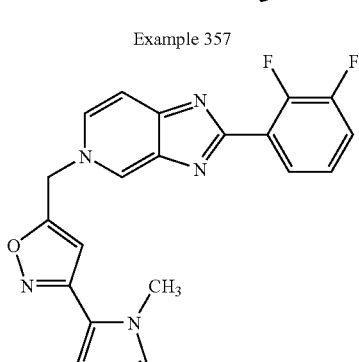 | 90 | 391.38 | | D |

-continued
| Structures | Purity | MW | Obs. MW | Method |
|---|---|---|---|---|
| Example 358 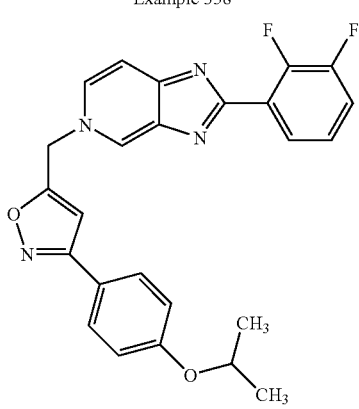 | 90 | 446.46 | | D |
| Example 359 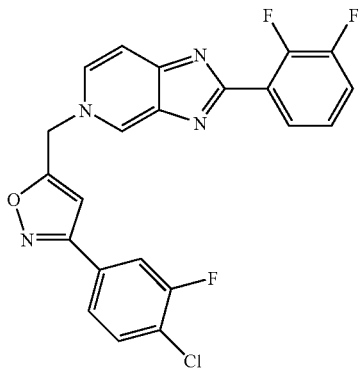 | 90 | 440.82 | | D |
| Example 360 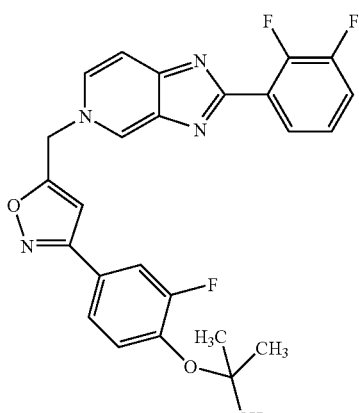 | 90 | 478.48 | | D |

-continued

| Structures | Purity | MW | Obs. MW | Method |
|---|---|---|---|---|
| Example 361 | 90 | 428.85 | | D |
| Example 362 | 90 | 460.49 | | D |
| Example 363 | 90 | 428.47 | | D |

-continued
| Structures | Purity | MW | Obs. MW | Method |
|---|---|---|---|---|
| Example 364 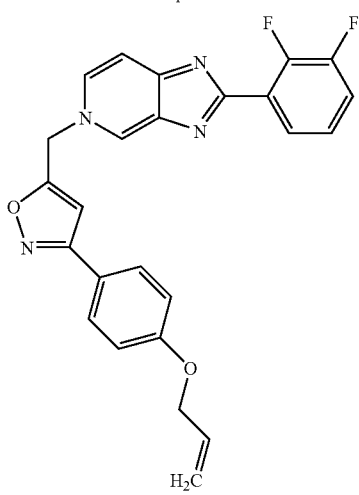 | 90 | 444.44 | | D |
| Example 365 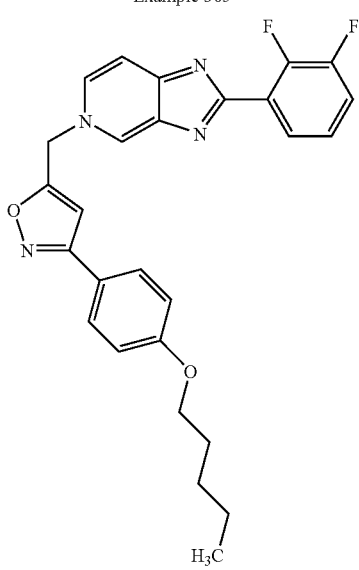 | 90 | 474.51 | | D |
| Example 366 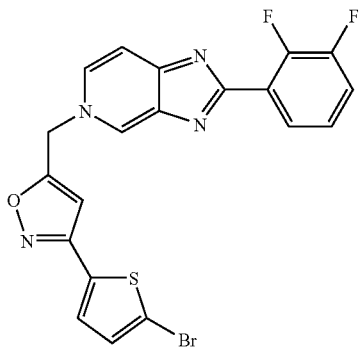 | 90 | 473.30 | | D |

| Structures | Purity | MW | Obs. MW | Method |
|---|---|---|---|---|
| Example 367 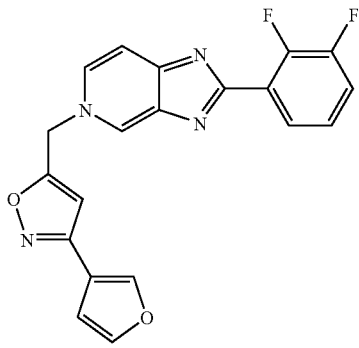 | 90 | 378.34 | | D |
| Example 368 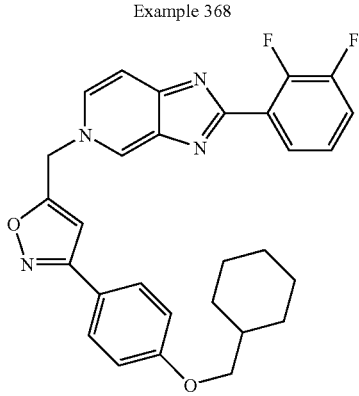 | 90 | 500.55 | | D |
| Example 369 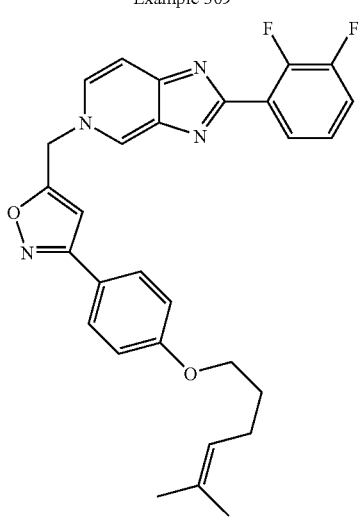 | 90 | 500.55 | | D |

-continued
| Structures | Purity | MW | Obs. MW | Method |
|---|---|---|---|---|
| Example 370 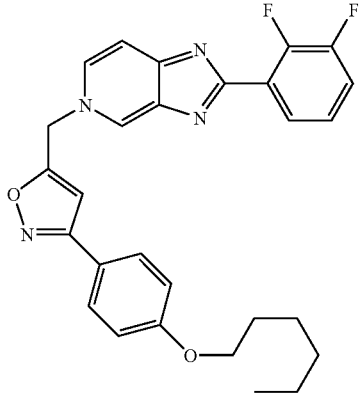 | 90 | 488.54 | | D |
| Example 371 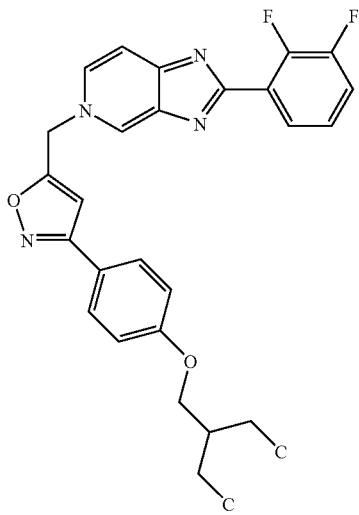 | 90 | 488.53 | | D |
| Example 372 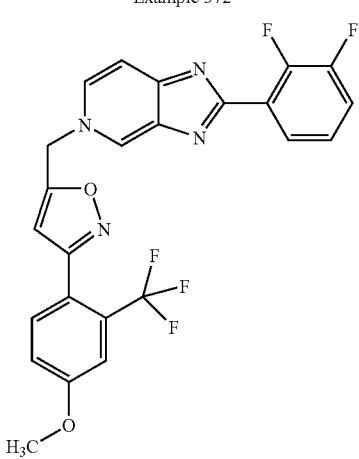 | 90 | 487.4 | | D |

| Structures | Purity | MW | Obs. MW | Method |
|---|---|---|---|---|
| Example 373 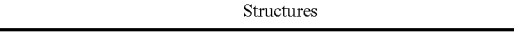 | 90 | 417.4 | | C |

Example 374

Isoxazole Analogues

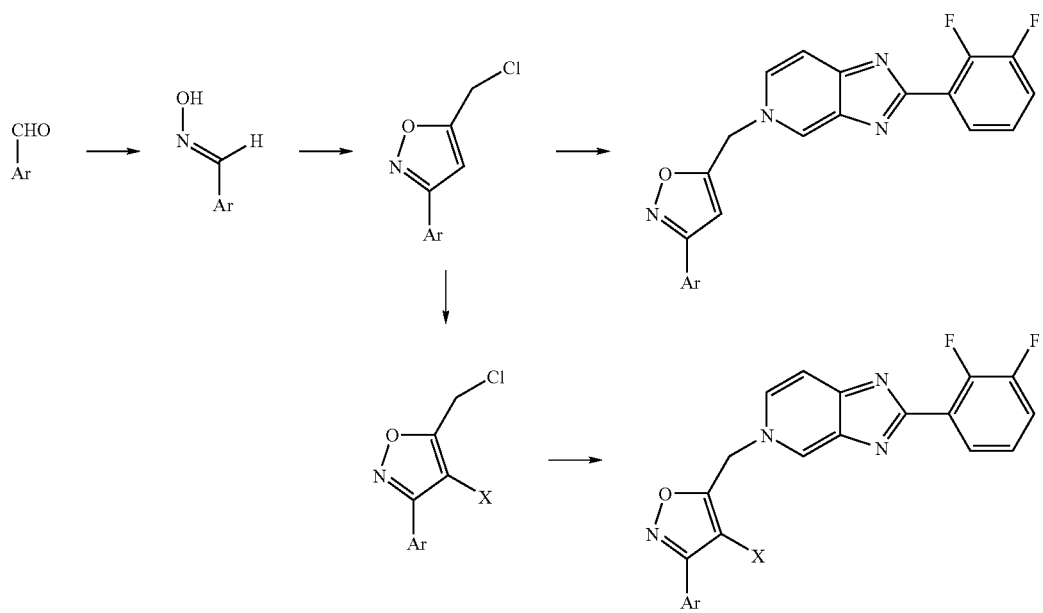

Ar = (subst.) phenyl, (subst.) hetaryl
X = Br, Cl

Synthesis of 374a:

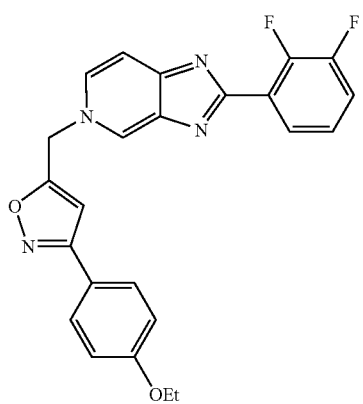

To a stirred solution of 4-ethoxy-benzaldehyde (3.000 g) in 50% ethanol (7 mL) ice (10 g) and hydroxylamine hydrochloride (2.100 g) were added, followed by 30% aqueous sodium hydroxide solution (3.5 mL). After completion of the reaction (1 h) hydrochloric acid was added to adjust pH to 1 and the suspension was cooled on an ice bath and filtered. The crude oxime can be used for the next step without purification. Alternatively, it can be recrystallized from a mixture of diisopropyl ether and ethyl acetate. Yield: 71%.

To a solution of propargyl chloride (655 mg, 1 equ.) and triethylamine (35 mg, 0.1 equ.) in dichloromethane (9.5 mL) were subsequently added with cooling 10% aqueous sodium hypochlorite solution (9.5 mL, 1.5 equ.) and then a solution of the oxime (1.40 g, ~1.3 M in dichloromethane) over a period of 15 minutes and stirring was continued for an additional hour. The reaction was monitored by TLC (silicagel, eluent: 5% MeOH in dichloromethane). After completion the reaction mixture was extracted 3 times with 30 mL dichloromethane. The combined organic phases were dried over anhydrous sodium sulphate and evaporated under reduced pressure. The crude 5-(chloromethyl)-3-(4-ethoxyphenyl)- isoxazole was purified by column chromatography (silicagel, ethyl acetate/petroleum ether=1:9). Yield: 1.1 g.

A mixture of 3,4-diaminopyridine (2.00 g), 2,3-difluorobenzoic acid (1 equivalent) and polyphosphoric acid (50 g) was heated at 180° C. for 4 h with stirring. Then the mixture was cooled to ambient temperature and poured into ice/water. The resulting mixture was neutralized by addition of solid NaOH. The crude 2-(2,3-difluorophenyl)-1(3)H-imidazo[4,5-c]pyridine was collected by filtration, washed with water and dried. It was used in the next step without further purification. Yield: 88%.

2-(2,3-Difluorophenyl)-1(3)H-imidazo[4,5-c]pyridine (0.500 g) was dissolved in dry DMF (5 mL) and the resulting solution was cooled to 0° C. Aqueous 50% sodium hydroxide (1.5 equivalents) was added and the mixture was stirred for 15 min. Then 5-(chloromethyl)-3-(4-ethoxyphenyl)-isoxazole (1.2 equivalents) was added and the resulting mixture was stirred for 24 h at room temperature. Finally, water (50 mL) was added, the precipitate was collected by filtration and dried to give the crude product.

Recrystallized from ethyl acetate; colorless crystals; yield: 35%

$^1$H NMR (200 MHz, DMSO-$d_6$) δ 9.24 (d, 1H, H4, J=1.2 Hz), 8.28 (dd, 1H, H6, J=6.6, 1.2 Hz), 8.15 (m, 1H, phenyl-H), 7.89 (d, 1H, H7, J=6.6 Hz), 7.77 (AA'BB', 2H, benzyl-H), 7.49 (m, 1H, phenyl-H), 7.31 (m, 1H, phenyl-H), 7.07-7.00 (m, 3H, arom. H), 6.02 (s, 2H, CH$_2$), 4.06 (q, 2H, OCH$_2$, J=6.9 Hz), 1.32 (t, 3H, CH$_3$, J=6.9 Hz).

The following examples were prepared by analogy to the above procedure:

374b

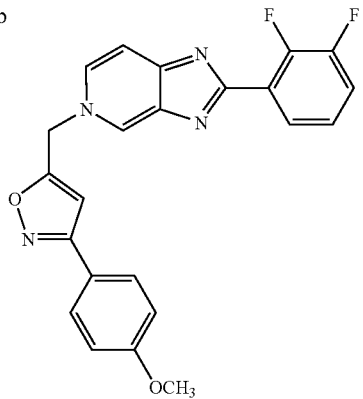

Starting from 4-methoxybenzaldehyde.

$^1$H NMR (200 MHz, DMSO-$d_6$) δ 9.23 (d, 1H, H4, J=1.2 Hz), 8.28 (dd, 1H, H6, J=6.6, 1.2 Hz), 8.15 (m, 1H, phenyl-H), 7.88 (d, 1H, H7, J=6.6 Hz), 7.79 (AA'BB', 2H, benzyl-H), 7.49 (m, 1H, phenyl-H), 7.31 (m, 1H, phenyl-H), 7.09-7.00 (m, 3H, arom. H), 6.01 (s, 2H, CH$_2$), 3.80 (s, 3H, OCH$_3$).

374c

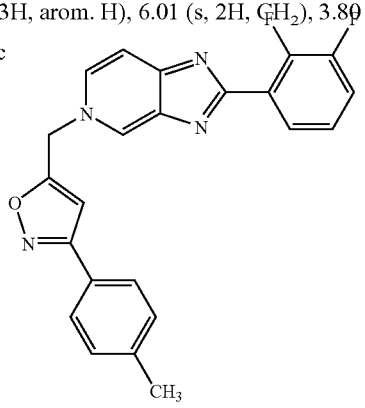

Starting from 4-methylbenzaldehyde.

$^1$H NMR (200 MHz, DMSO-$d_6$) δ 9.24 (br s, 1H, H4), 8.29 (d, 1H, H6, J=6.7 Hz), 8.14 (m, 1H, phenyl-H), 7.88 (d, 1H, H7, J=6.7 Hz), 7.58-7.27 (m, 6H, arom. H), 7.00 (s, 1H, isoxazole-H), 6.04 (s, 2H, CH$_2$), 2.41 (s, 3H, CH$_3$).

374d

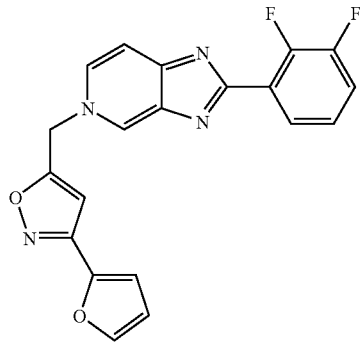

Starting from 2-furaldehyde $^1$H NMR (200 MHz, DMSO-$d_6$) δ 9.24 (br s, 1H, H4), 8.28 (d, 1H, H6, J=6.7 Hz), 8.15 (m, 1H, phenyl-H), 7.90-7.87 (m, 2H, arom. H), 7.51 (m, 1H, phenyl-H), 7.32 (m, 1H, phenyl-H), 7.15 (d, 1H, furane-H, J=3.6 Hz), 6.96 (s, 1H, isoxazole-H), 6.68 (m, 1H, furane-H), 6.02 (s, 2H, CH$_2$).

374e

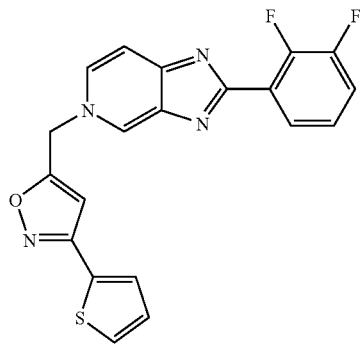

Starting from thiophene-2-carboxaldehyde $^1$H NMR (200 MHz, DMSO-$d_6$) δ 9.23 (d, 1H, H4, J=1.6 Hz), 8.27 (dd, 1H, H6, J=7.0, 1.6 Hz), 8.14 (m, 1H, phenyl-H), 7.88 (d, 1H, H7, J=7.0 Hz), 7.75-7.70 (m, 2H, arom. H), 7.50 (m, 1H, phenyl-H), 7.31 (m, 1H, phenyl-H), 7.19 (dd, 1H, thiophene-H), 7.06 (s, 1H, isoxazole-H), 6.02 (s, 2H, CH$_2$).

374f

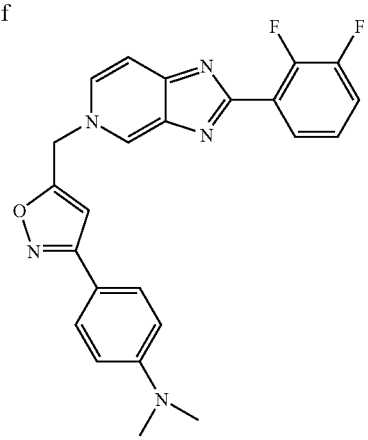

Starting from 4-dimethylanainobenzaldehyde

¹H NMR (200 MHz, DMSO-d₆) δ 9.23 (d, 1H, H4, J=1.6 Hz), 8.27 (dd, 1H, H6, J=7.0, 1.6 Hz), 8.14 (m, 1H, phenyl-H), 7.88 (d, 1H, H7, J=7.0 Hz), 7.65 (AA'BB', 2H, benzyl-H), 7.49 (m, 1H, phenyl-H), 7.31 (m, 1H, phenyl-H), 6.98 (s, 1H, isoxazole-H), 6.76 (AA'BB', 2H, benzyl-H), 5.75 (s, 2H, CH₂), 2.95 (s, 6H, N(CH₃)₂).

374g

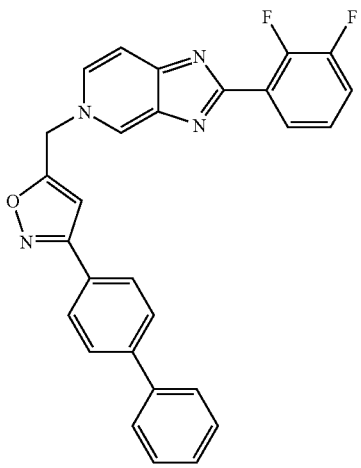

Starting from 4-biphenylcarboxaldehyde

¹H NMR (200 MHz, DMSO-d₆) δ 9.25 (d, 1H, H4, J=1.6 Hz), 8.30 (dd, 1H, H6, J=7.0, 1.6 Hz), 8.16 (m, 1H, phenyl-H), 7.98-7.70 (m, 7H, arom. H), 7.57-7.26 (m, 5H, arom. H), 7.18 (s, 1H, isoxazole-H), 6.05 (s, 2H, CH₂).

374h

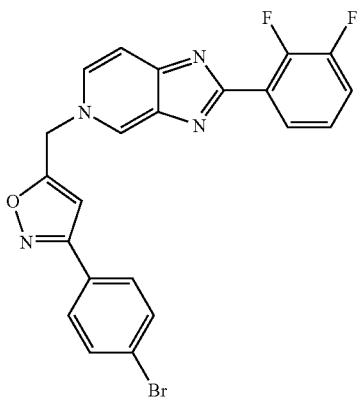

Starting from 4-bromobenzaldehyde

¹H NMR (200 MHz, DMSO-d₆) δ 9.23 (d, 1H, H4, J=1.6 Hz), 8.28 (dd, 1H, H6, J=7.0, 1.6 Hz), 8.16 (m, 1H, phenyl-H), 7.90-7.68 (m, 4H, arom. H), 7.51 (m, 1H, phenyl-H), 7.31 (m, 1H, phenyl-H), 7.15 (s, 1H, isoxazole-H), 6.05 (s, 2H, CH₂).

374i

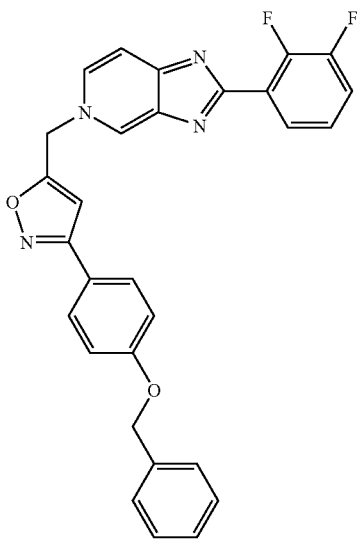

Starting from 4-benzyloxybenzaldehyde

¹H NMR (200 MHz, DMSO-d₆) δ 9.23 (d, 1H, H4, J=1.6 Hz), 8.27 (dd, 1H, H6, J=7.0, 1.6 Hz), 8.15 (m, 1H, phenyl-H), 7.90-7.76 (m, 3H, arom. H), 7.57-7.26 (m, 7H, arom. H), 7.15-7.05 (m, 3H, arom. H), 6.01 (s, 2H, N—CH₂), 5.16 (s, 2H, O—CH₂).

374j

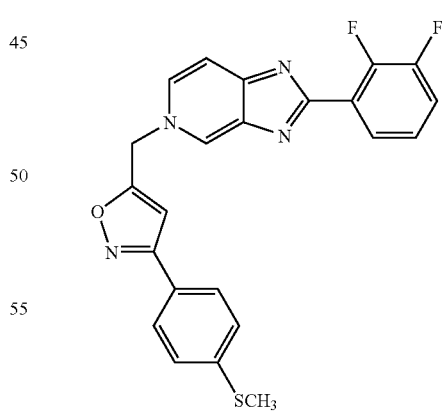

Starting from 4-(methylthio)benzaldehyde

¹H NMR (200 MHz, DMSO-d₆) δ 9.23 (d, 1H, H4, J=1.2 Hz), 8.28 (dd, 1H, H6, J=6.6, 1.2 Hz), 8.15 (m, 1H, phenyl-H), 7.88 (d, 1H, H7, J=6.6 Hz), 7.79 (AA'BB', 2H, benzyl-H), 7.50 (m, 1H, phenyl-H), 7.38-7.25 (m, 3H, arom. H), 7.10 (s, 1H, isoxazole-H), 6.03 (s, 2H, CH₂), 2.51 (s, 3H, SCH₃).

374k

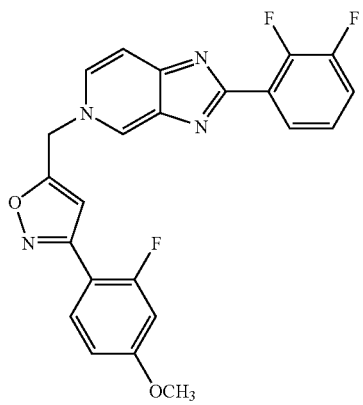

Starting from 2-fluoro-4-methoxybenzaldehyde

¹H NMR (200 MHz, DMSO-d₆) δ 9.26 (d, 1H, H4, J=1.2 Hz), 8.30 (dd, 1H, H6, J=6.6, 1.2 Hz), 8.14 (m, 1H, phenyl-H), 7.88 (d, 1H, H7, J=6.6 Hz), 7.80 (m, 1H, benzyl-H), 7.49 (m, 1H, phenyl-H), 7.31 (m, 1H, phenyl-H), 7.04-6.71 (m, 3H, arom. H), 6.03 (s, 2H, CH₂), 3.82 (s, 3H, OCH₃).

374l

Starting from 4-propoxybenzaldehyde

¹H NMR (200 MHz, DMSO-d₆) δ 9.23 (d, 1H, H4, J=1.2 Hz), 8.29 (dd, 1H, H6, J=6.6, 1.2 Hz), 8.14 (m, 1H, phenyl-H), 7.88 (d, 1H, H7, J=6.6 Hz), 7.78 (AA'BB', 2H, benzyl-H), 7.49 (m, 1H, phenyl-H), 7.31 (m, 1H, phenyl-H), 7.06-7.00 (m, 3H, arom. H), 6.01 (s, 2H, CH₂), 3.97 (t, 2H, OCH₂, J=6.5 Hz), 1.73 (hex, 2H, CH₂), 0.97 (t, 3H, CH₃, J=7.3 Hz).

374w

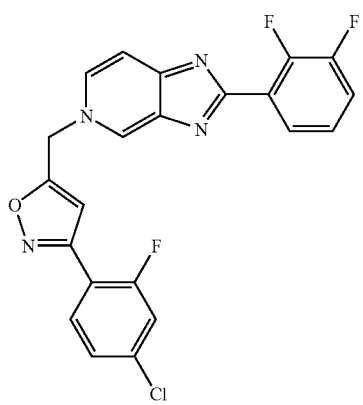

Prepared as described above, starting from 4-chloro-2-fluorobenzaldehyde.

¹H NMR (200 MHz, DMSO-d₆) □ 9.26 (d, 1H, H4, J=1.4 Hz), 8.30 (dd, 1H, H6, J=6.8, 1.4 Hz), 8.14 (m, 1H, phenyl-H), 7.90-7.87 (m, 2H, arom. H), 7.66 (dd, 1H, arom. H, J=10.8, 1.8 Hz), 7.53-7.41 (m, 2H, arom. H), 7.31 (m, 1H, phenyl-H), 7.10 (d, 1H, isoxazole-H, J=2.7 Hz), 6.06 (s, 2H, CH₂).

374m

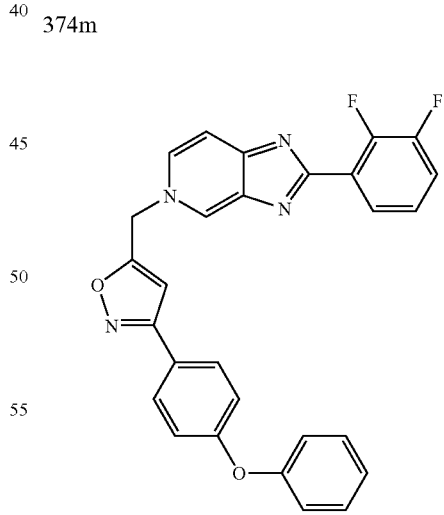

Starting from 4-phenoxybenzaldehyde

¹H NMR (200 MHz, DMSO-d₆) δ 9.25 (d, 1H, H4, J=1.2 Hz), 8.29 (dd, 1H, H6, J=6.6, 1.2 Hz), 8.16 (m, 1H, phenyl-H), 7.92-7.83 (m, 3H, arom. H), 7.58-7.05 (m, 10H, arom. H), 6.04 (s, 2H, CH₂).

374n

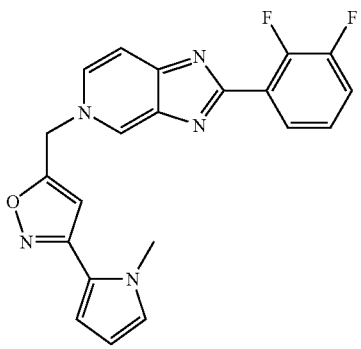

Starting from 1-methylpyrrole-2-carboxaldehyde

¹H NMR (200 MHz, DMSO-d₆) δ 9.24 (d, 1H, H4, J=1.2 Hz), 8.28 (dd, 1H, H6, J=6.8, 1.2 Hz), 8.16 (m, 1H, phenyl-H), 7.89 (d, 1H, H7, J=6.8 Hz), 7.50 (m, 1H, phenyl-H), 7.31 (m, 1H, phenyl-H), 6.98 (dd, 1H, pyrrole-H), 6.92 (s, 1H, isoxazole-H), 6.68 (dd, 1H, pyrrole-H), 6.12 (dd, 1H, pyrrole-H), 6.00 (s, 2H, CH₂).

374p

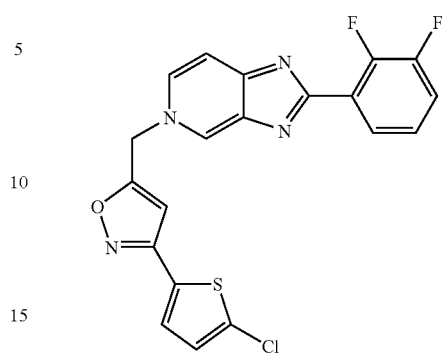

Synthesized as described above, starting from 5-chlorothiophene-2-carboxaldehyde.

¹H NMR (200 MHz, DMSO-d₆) δ 9.23 (d, 1H, H4, J=1.4 Hz), 8.27 (dd, 1H, H6, J=7.0, 1.4 Hz), 8.14 (m, 1H, phenyl-H), 7.89 (d, 1H, H7, J=7.0 Hz), 7.63 (d, 1H, thiophene-H, J=4.0 Hz), 7.51 (m, 1H, phenyl-H), 7.37-7.24 (m, 2H, arom. H), 7.07 (s, 1H, isoxazole-H), 6.03 (s, 2H, CH₂).

374o

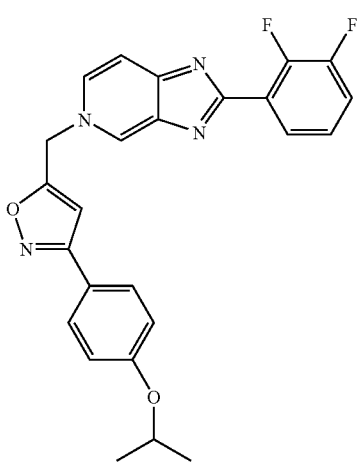

Starting from 4-isopropoxybenzaldehyde.

¹H NMR (200 MHz, DMSO-d₆) δ 9.24 (d, 1H, H4, J=1.4 Hz), 8.28 (dd, 1H, H6, J=7.0, 1.4 Hz), 8.15 (m, 1H, phenyl-H), 7.89 (d, 1H, H7, J=7.0 Hz), 7.76 (AA'BB', 2H, benzyl-H), 7.50 (m, 1H, phenyl-H), 7.31 (m, 1H, phenyl-H), 7.05-6.98 (m, 3H, arom. H), 6.01 (s, 2H, CH₂), 4.67 (hept, 1H, OCH, J=6.2 Hz), 1.26 (d, 6H, (CH₃)₂, J=6.2 Hz).

374q

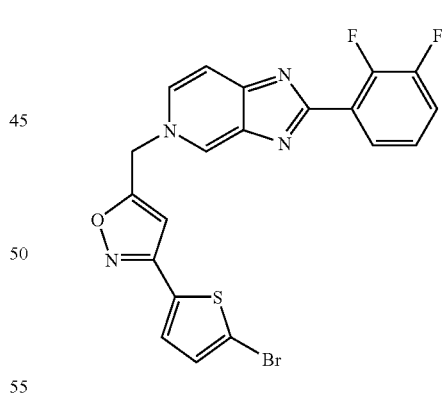

Synthesized as described above, starting from 5-bromothiophene-2-carboxaldehyde.

¹H NMR (200 MHz, DMSO-d₆) δ 9.23 (d, 1H, H4, J=1.4 Hz), 8.27 (dd, 1H, H6, J=6.6, 1.4 Hz), 8.14 (m, 1H, phenyl-H), 7.89 (d, 1H, H7, J=6.6 Hz), 7.59 (d, 1H, thiophene-H, J=3.6 Hz), 7.50 (m, 1H, phenyl-H), 7.36-7.27 (m, 2H, arom. H), 7.06 (s, 1H, isoxazole-H), 6.02 (s, 2H, CH₂).

374r

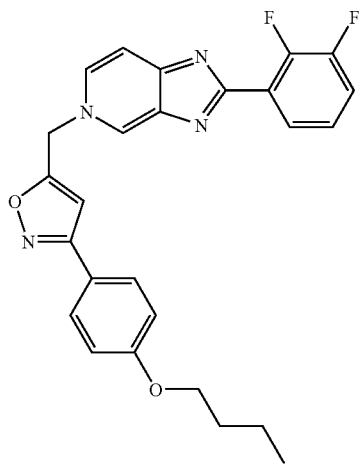

Synthesized as described above, starting from 4-butoxybenzaldehyde (prepared by alklylation of 4-hydroxybenzaldehyde).

$^1$H NMR (200 MHz, DMSO-d$_6$) δ 9.24 (d, 1H, H4, J=1.2 Hz), 8.28 (dd, 1H, H6, J=6.6, 1.2 Hz), 8.15 (m, 1H, phenyl-H), 7.89 (d, 1H, H7, J=6.6 Hz), 7.78 (AA'BB', 2H, benzyl-H), 7.50 (m, 1H, phenyl-H), 7.31 (m, 1H, phenyl-H), 7.07-7.01 (m, 3H, arom. H), 6.01 (s, 2H, CH$_2$), 4.01 (t, 2H, OCH$_2$, J=6.5 Hz), 1.72 (m, 2H, CH$_2$), 1.42 (m, 2H, CH$_2$), 0.93 (t, 3H, CH$_3$, J=7.2 Hz).

374s

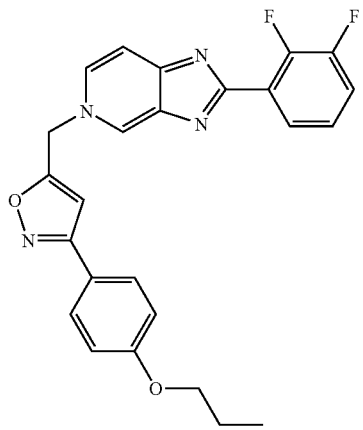

Synthesized as described above, starting from 4-propoxybenzaldehyde and using 2-(2-fluorophenyl)-1(3)H-imidazo[4,5-c]pyridine instead of 2-(2,3-difluorophenyl)-1(3)H-imidazo[4,5-c]pyridine.

$^1$H NMR (200 MHz, DMSO-d$_6$) □ 9.18 (d, 1H, H4, J=1.2 Hz), 8.38-8.23 (m, 2H, arom. H), 7.85 (d, 1H, H7, J=6.6 Hz), 7.78 (AA'BB', 2H, benzyl-H), 7.54-7.25 (m, 3H, phenyl-H), 7.06-7.00 (m, 3H, arom. H), 6.00 (s, 2H, CH$_2$), 3.98 (t, 2H, OCH$_2$, J=6.6 Hz), 1.73 (hex, 2H, CH$_2$), 0.97 (t, 3H, CH$_3$, J=7.3 Hz).

374t

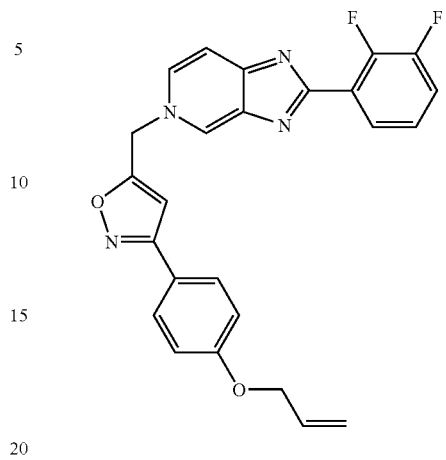

Starting from 4-allyloxybenzaldehyde $^1$H NMR (200 MHz, DMSO-d$_6$) δ 9.23 (d, 1H, H4, J=1.2 Hz), 8.27 (dd, 1H, H6, J=6.7, 1.2 Hz), 8.14 (m, 1H, phenyl-H), 7.89 (d, 1H, H7, J=6.7 Hz), 7.79 (AA'BB', 2H, benzyl-H), 7.50 (m, 1H, phenyl-H), 7.31 (m, 1H, phenyl-H), 7.09-7.00 (m, 3H, arom. H), 6.15-5.98 (m, 3H), 5.45-5.24 (m, 2H), 4.62 (d, 2H, J=4.8 Hz).

374u

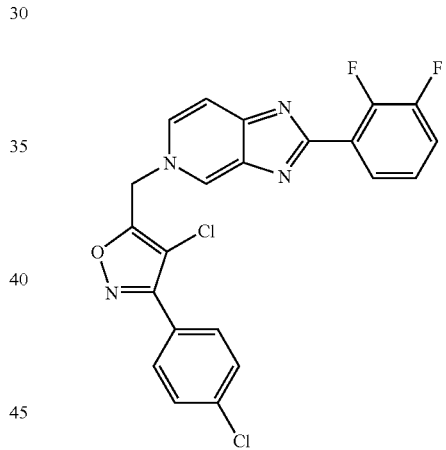

A mixture of 5-(chloromethyl)-3-(4-chlorophenyl)-isoxazole (2.00 g), NCS (11.75 g, 10 equivalents), glacial acetic acid (35 mL) and 20 drops of concentrated sulphuric acid is heated to reflux for 3 days. After cooling to room temperature dichloromethane (100 mL) is added, and the resulting mixture is extracted with water (2×100 mL) and saturated aqueous sodium bicarbonate solution (2×100 mL). Then the organic phase was dried over anhydrous sodium sulphate and evaporated. The crude product, thus obtained, was purified by column chromatography (silica gel, eluent: petroleum ether/ethyl acetate=19/1) to give 1.14 g.

The final step was performed as described above. Recrystallized from a mixture of ethyl acetate and ethanol. Yield: 60%.

$^1$H NMR (200 MHz, DMSO-d$_6$) □ 9.20 (d, 1H, H4, J=1.4 Hz), 8.25 (dd, 1H, H6, J=6.8, 1.4 Hz), 8.15 (m, 1H, phenyl-H), 7.89 (d, 1H, H7, J=6.8 Hz), 7.83 (AA'BB', 2H, benzyl-H), 7.66 (AA'BB', 2H, benzyl-H), 7.51 (m, 1H, phenyl-H), 7.31 (m, 1H, phenyl-H), 6.14 (s, 2H, CH$_2$).

374v

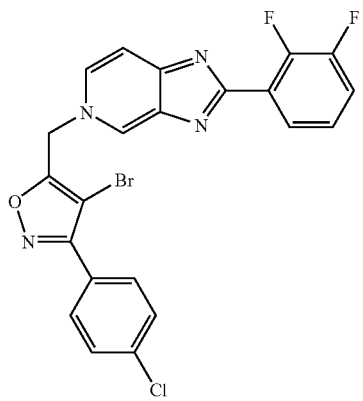

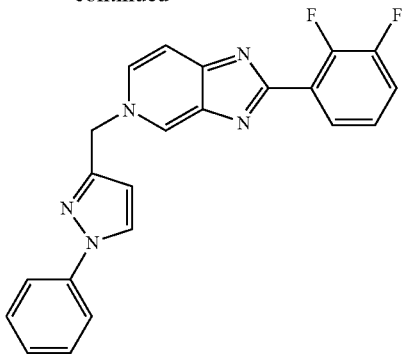

-continued

¹H NMR (200 MHz, DMSO-d$_6$) δ 9.18 (d, 1H, H4, J=1.4 Hz), 8.22 (dd, 1H, H6, J=6.8, 1.4 Hz), 8.14 (m, 1H, phenyl-H), 7.89 (d, 1H, H7, J=6.8 Hz), 7.80 (AA'BB', 2H, benzyl-H), 7.65 (AA'BB', 2H, benzyl-H), 7.49 (m, 1H, phenyl-H), 7.30 (m, 1H, phenyl-H), 6.11 (s, 2H, CH$_2$).

Synthesized in analogy to the chloroisoxazole derivative 374u: 4 equ. NBS, 2.5 h reflux, yield: 91%.

Example 375

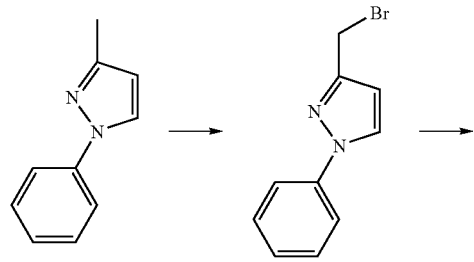

To a solution of 500 mg 3-methyl-1-phenylpyrazole in 4 mL carbontetrachloride is added in portions at 70° C. a mixture of 678 mg (1.2 equi.) NBS and AIBN (62.3 mg, 0.12 equ.). The resulting mixture is heated at reflux for an additional 15 minutes and then cooled to room temperature. The precipitate is filtered off and the filtrate is concentrated to precipitate the crude product (380 mg), which—after collecting by filtration and drying—was used in the next step without further purification The final step was performed as described above. Recrystallized from ethyl acetate. Yield: 35%.

Example 376 imidazo[4,5-c]pyridin-4-one Analogues

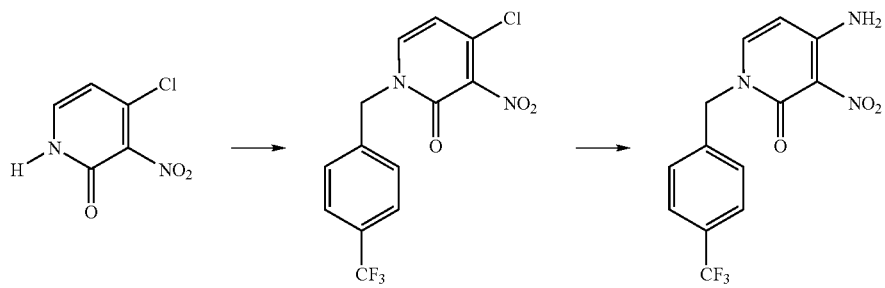

-continued

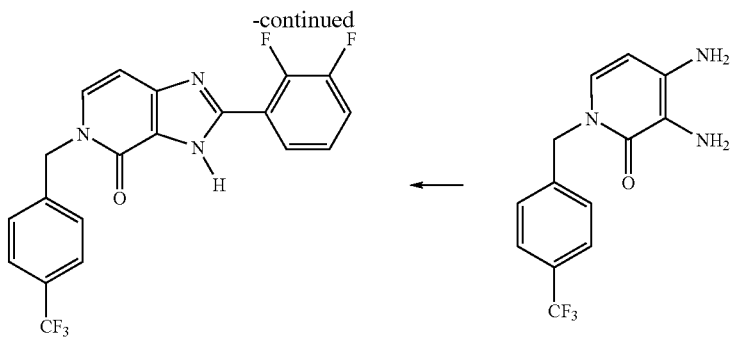

A mixture of 4-chloro-3-nitro-pyridin-2-one (1.00 g), 4-(trifluoromethyl)benzyl chloride (1.226 g), anhydrous potassium carbonate (0.871 g) and anhydrous DMF (10 mL) was stirred at ambient temperature for 24 hours. Then water (100 mL) was added and the resulting precipitate was collected by filtration, washed with water and dried. Yield: 58.2% 4-chloro-3-nitro-1-(4-trifluoromethyl)benzyl-pyridin-2-one.

4-Chloro-3-nitro-1-(4-trifluoromethyl)benzyl-pyridin-2-one (500 mg) was dissolved in anhydrous THF (10 mL). Then concentrated aqueous ammonia (7.5 mL) was added and the resulting mixture was stirred at room temperature for 24 hours. Water (50 mL) was added and the resulting precipitate was collected by filtration, washed with water and dried. Yield: 45.8% of 4-amino-3-nitro-1-(4-trifluoromethyl)benzyl-pyridin-2-one.

A mixture of 4-amino-3-nitro-1-(4-trifluoromethyl)benzyl-pyridin-2-one (1.400 g), saturated aqueous ammoniumchloride solution (9.4 mL), zink powder (1.400 g) and methanol (235 mL) was stirred at room temperature for 1 hour. Then additional zink powder (1.400 g) was added and the resulting mixture was stirred for an additional 23 hours. After evaporation of the solvent water (30 mL) was added and the pH was adjusted to 8-9 by addition of 2N NaOH. The resulting mixture was extracted with ethyl acetate (3×30 mL) and the combined organic phases were washed with water (30 mL), dried over anhydrous sodium sulphate and evaporated. Yield: 53.4% 3,4-diamino-1-(4-trifluoromethyl)benzyl-pyridin-2-one.

A mixture of 3,4-diamino-1-(4-trifluoromethyl)benzyl-pyridin-2-one (0.200 mg), 2,3-difluorobenzaldehyde (100 mg), sodium pyrosulfite (0.134 g) and N,N-dimethylacetamide (4.6 mL) was heated at 130° C. for 24 hours. Then water (30 mL) was added and the resulting precipitate was collected by filtration, washed with water and dried. The crude product was purified by column chromatography (silicagel, eluent: dichloromethane/methanol=12/1) and then recrystallized from a mixture of diisopropyl ether and ethyl acetate. Yield: 16.8%.

Melting point: 279-283° C.
$^1$H NMR (200 MHz, DMSO-$d_6$) δ 13.05 (br s, 1H, NH), 7.88 (m, 1H, phenyl-H), 7.74-7.32 (m, 7H, arom. H), 6.69 (br d, 1H, H7, J=6.0 Hz), 5.34 (s, 2H, $CH_2$).

Example 377

Synthesis of the 4-methyl analogue 377

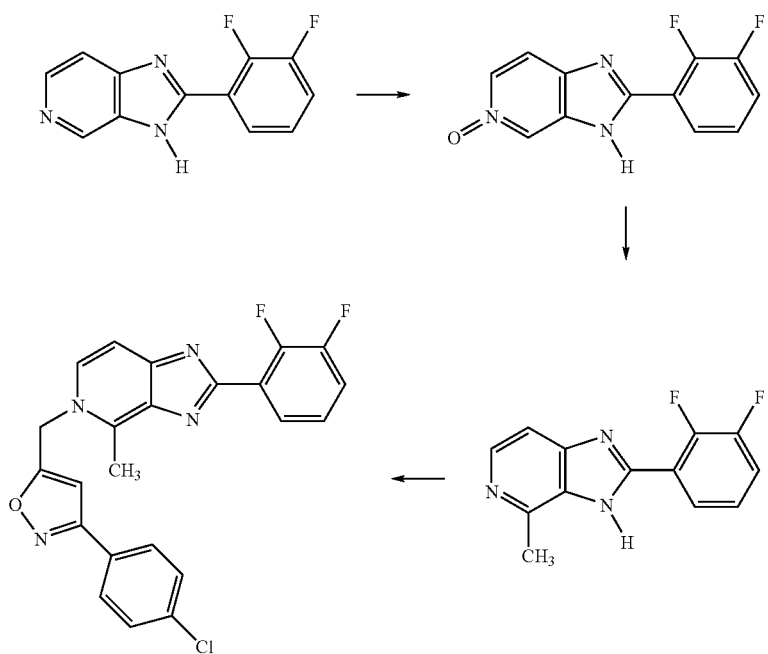

A mixture of 2-(2,3-difluorophenyl)-1(3)H-imidazo[4,5-c]pyridine (2.00 g), 50 mg methyltrioxorhenium, 100 mL methanol and 30% aqueous hydrogen peroxide (4 mL) was stirred at room temperature for 4 days. Then, additional 50 mg of methyltrioxorhenium and 30% hydrogen peroxide (4 mL) were added and the resulting mixture was stirred for another 2 days. After evaporation of the methanol water (200 mL) was added and the pH was adjusted to 9 by addition of 2N NaOH. The resulting precipitate was filtered, dried and recrystallized from a mixture of ethyl acetate (20 mL) and ethanol (53 mL) to give 1.208 g (56.5%) of 2-(2,3-difluorophenyl)-1(3)H-imidazo[4,5-c]pyridine 5-oxide.

2-(2,3-Difluorophenyl)-1(3)H-imidazo[4,5-c]pyridine 5-oxide (1.00 g) was dissolved in dry tetrahydrofurane (100 mL) and MeMgBr-solution (14 mL, 3M in diethyl ether) was added dropwise under argon. The resulting mixture was stirred for 1.5 hours at ambient temperature. Then water (100 mL) was added slowly and the pH was adjusted to 8.5. Extraction with ethyl acetate (3×70 mL), drying of the combined organic phases over anhydrous sodium sulphate and evaporation of the solvent afforded 0.630 g (60%) of crude 2-(2,3-difluorophenyl)-4-methyl-[(3)H-imidazo[4,5-c]pyridine. Recrystallization from a mixture of diisopropyl ether (20 mL) and ethyl acetate (34 mL) gave 240 mg (24.2%) of pure 2-(2,3-difluorophenyl)-4-methyl-1(3)H-imidazo[4,5-c]pyridine.

The final step was performed as described above. Purification by column chromatography (silica gel, eluent: dichloromethane/methanol=20/1). Yield: 22.4%.

$^1$H NMR (200 MHz, DMSO-$d_6$) δ 8.25 (d, 1H, H6, J=6.8 Hz), 8.11 (m, 1H, phenyl-H), 7.89 (AA'BB', 2H, benzyl-H), 7.77 (d, 1H, H7, J=6.8 Hz), 7.60-7.41 (m, 3H, arom. H), 7.30 (m, 1H, phenyl-H), 7.12 (s, 1H, isoxazole-H), 6.05 (s, 2H, $CH_2$), 3.05 (s, 3H, $CH_3$).

Example 378

Synthesis of 7-Substituted Analogues

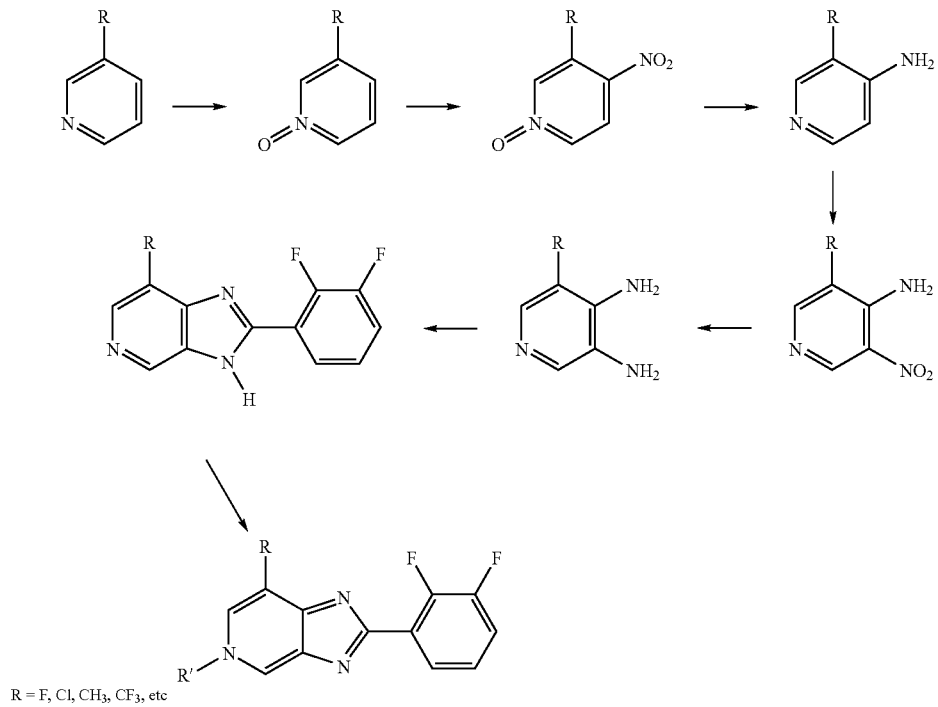

R = F, Cl, $CH_3$, $CF_3$, etc

378a

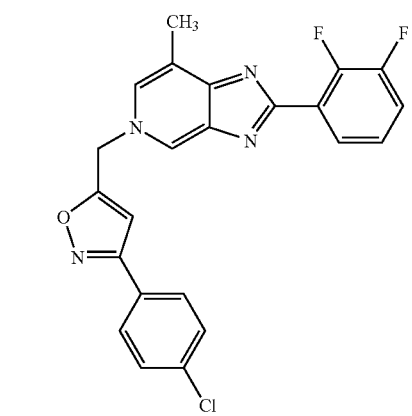

3-Methyl-4-nitropyridine 1-oxide (5.85 g) was dissolved in glacial acetic acid (115 mL) and hydrogenated in a Parr hydrogenation apparatus (catalyst: 220 mg $PtO_2 \times 2H_2O$, 50 psi) at ambient temperature for 2.5 h. Then the catalyst was filtered off and the solvent was evaporated. After addition of 150 mL of water the pH was adjusted to 12 by addition of 2N NaOH. The resulting solution was extracted 10 times with 100 mL of dichloromethane (containing 5% methanol). The combined organic phases were dried over anhydrous sodium sulphate and evaporated to give 3.81 g (83.6%) of 4-amino-3-methylpyridine.

4-Amino-3-methylpyridine (3.00 g) was dissolved with icecooling in concentrated sulfuric acid (36 mL). Then, fuming nitric acid (4.72 g) was added dropwise. After stirring at room temperature for 1 h, the solution was heated at 60° C. for 14 hours. After cooling to ambient temperature, the reaction mixture was poured on ice and the resulting solution was adjusted to pH 13 by addition of solid KOH. The precipitate was filtered off, washed with water and dried. Yield: 1.198 g (31.3%) 4-amino-3-methyl-5-nitropyridine.

A mixture of 4-amino-3-methyl-5-nitropyridine (1.198 g), iron powder (1.748 g), ethanol (52 mL) and hydrochloric acid (13 mL) was heated to reflux for 3 hours. After cooling to room temperature the ethanol was distilled off and the resulting suspension was diluted with water to 50 mL and the pH was adjusted to 13 by addition of 2N NaOH. Extraction with ethyl acetate (3×70 mL), drying of the combined organic phases of anhydrous sodium sulphate and evaporation of the solvent afforded 0.579 g (60%) of 3,4-diamino-5-methylpyridine.

The cyclization with 2,3-difluorbenzoic acid in PPA was performed as described above. Purified by column chromatography (silica gel, eluent: dichloromethan/methanol=12/1). Yield: 22.2%.

The final step was performed as described above. Recrystallized from a mixture of ethyl acetate and ethanol. Yield: 42.9% 378a.

$^1$H NMR (200 MHz, DMSO-d$_6$) δ 9.14 (d, 1H, H4, J=1.2 Hz), 8.17-8.10 (m, 2H, arom. H), 7.90 (AA'BB', 2H, benzyl-H), 7.60-7.42 (m, 3H, arom. H), 7.32 (m, 1H, phenyl-H), 7.15 (s, 1H, isoxazole-H), 5.99 (s, 2H, CH$_2$), 2.58 (s, 3H, CH$_3$).

The following compounds were prepared in analogy to the above procedures:

378b

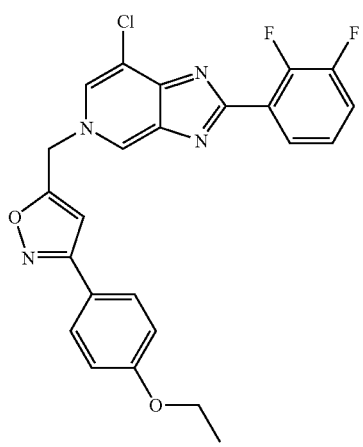

$^1$H NMR (200 MHz, DMSO-d$_6$) δ 9.32 (d, 1H, H4, J=1.4 Hz), 8.67 (d, 1H, H6, J=1.4 Hz), 8.16 (m, 1H, phenyl-H), 7.78 (AA'BB', 2H, benzyl-H), 7.54 (m, 1H, phenyl-H), 7.34 (m, 1H, phenyl-H), 7.07-7.00 (m, 3H, arom. H), 6.00 (s, 2H, CH$_2$), 4.07 (q, 2H, OCH$_2$, J=7.0 Hz), 1.33 (t, 3H, CH$_3$, J=7.0 Hz).

378c

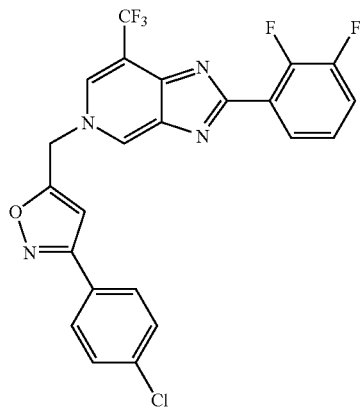

$^1$H NMR (200 MHz, DMSO-d$_6$) δ 9.47 (d, 1H, H4, J=1.4 Hz), 8.94 (d, 1H, H6, J=1.4 Hz), 8.16 (m, 1H, phenyl-H), 7.89 (AA'BB', 2H, benzyl-H), 7.63-7.50 (m, 3H, arom. H), 7.35 (m, 1H, phenyl-H), 7.16 (s, 1H, isoxazole-H), 6.10 (s, 2H, CH$_2$).

378d

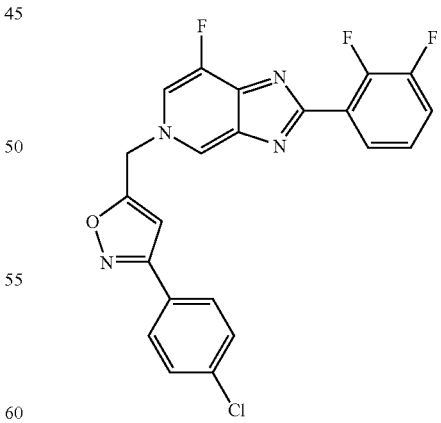

$^1$H NMR (200 MHz, DMSO-d$_6$) δ 9.30 (br s, 1H, H4), 8.66 (dd, 1H, H6, J=7.4, 1.4 Hz), 8.15 (m, 1H, phenyl-H), 7.89 (AA'BB', 2H, benzyl-H), 7.61-7.47 (m, 3H, arom. H), 7.33 (m, 1H, phenyl-H), 7.16 (s, 1H, isoxazole-H), 6.04 (s, 2H, CH$_2$).

Example 379
1,2,4-oxadiazoles

379a

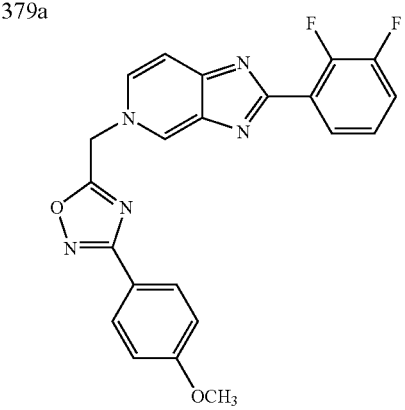

A mixture of 4-methoxybenzonitrile (1.00 g), hydroxylamine hydrochloride (0.785 g), KOH (0.640 g) and methanol (20 mL) was heated to reflux for 3 hours. After cooling to room temperature the precipitate was filtered off and the filtrate was evaporated. The resulting residue was dissolved in 1N HCl (100 mL) and the resulting solution was extracted with diethyl ether (100 mL). The aqueous phase was neutralized by addition of solid NaHCO$_3$ and extracted with diethyl ether (2×100 mL). The combined organic phases were dried over anhydrous sodium sulphate and evaporated to give 450 mg of the desired amidoxime, which was used without further purification.

A solution of 700 mg of (4-methoxyphenyl)amidoxime and 1.08 g (1.5 equivalents) chloroacetic anhydride in toluene (30 mL) was heated to reflux for 3 hours. After cooling to ambient temperature the reaction mixture was extracted subsequently with water (twice 50 mL), saturated sodium bicarbonate solution (twice 50 mL) and water (50 mL). Finally, the toluene phase was dried over anhydrous sodium sulphate and evaporated to give 660 mg of the desired oxadiazole, which was used without further purification.

The final step was performed as described above (see, for example, isoxazole analogues). Recrystallized from a mixture of ethyl acetate and ethanol. Yield: 35%

$^1$H NMR (200 MHz, DMSO-d$_6$) δ 9.23 (d, 1H, H4, J=1.4 Hz), 8.28 (dd, 1H, H6, J=6.8, 1.4 Hz), 8.15 (m, 1H, phenyl-H), 7.92-7.77 (m, 3H, arom. H), 7.49 (m, 1H, phenyl-H), 7.33 (m, 1H, phenyl-H), 7.08-7.00 (m, 3H, arom. H), 6.01 (s, 2H, CH$_2$), 3.80 (s, 3H, OCH$_3$).

379b

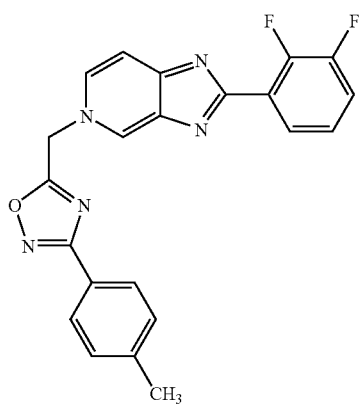

Prepared as described above, starting from 4-methylbenzonitrile.

$^1$H NMR (200 MHz, DMSO-d$_6$) δ 9.23 (d, 1H, H4, J=1.4 Hz), 8.31 (dd, 1H, H6, J=6.8, 1.4 Hz), 8.14 (m, 1H, phenyl-H), 7.93-7.78 (m, 3H, arom. H), 7.50 (m, 1H, phenyl-H), 7.35-7.27 (m, 3H, arom. H), 6.25 (s, 2H, CH$_2$), 2.35 (s, 3H, CH$_3$).

379c

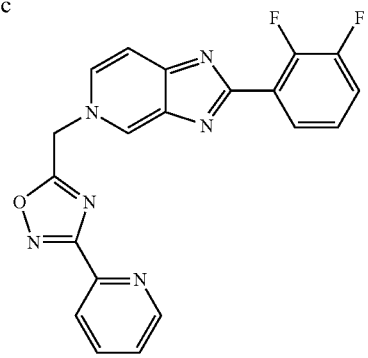

Prepared as described above, starting from pyridine-2-carbonitrile.

$^1$H NMR (200 MHz, DMSO-d$_6$) δ 9.24 (d, 1H, H4, J=1.4 Hz), 8.72 (ddd, 1H, pyridine-H), 8.32 (dd, 1H, H6, J=6.8, 1.4 Hz), 8.15 (m, 1H, phenyl-H), 8.00-7.90 (m, 3H, arom. H), 7.64-7.27 (m, 3H, arom. H), 6.30 (s, 2H, CH$_2$).

379d

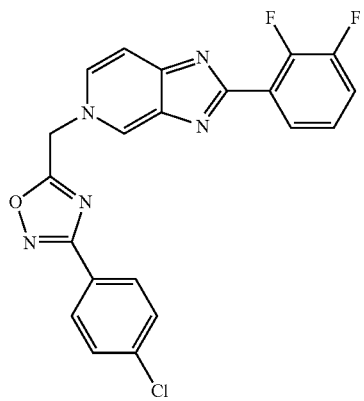

Prepared as described above, starting from 4-chlorobenzonitrile.

$^1$H NMR (200 MHz, DMSO-d$_6$) δ 9.24 (d, 1H, H4, J=1.4 Hz), 8.31 (dd, 1H, H6, J=6.8, 1.4 Hz), 8.16 (m, 1H, phenyl-H), 7.96-7.90 (m, 3H, arom. H), 7.60 (AA'BB', 2H, benzyl-H), 7.49 (m, 1H, phenyl-H), 7.34 (m, 1H, phenyl-H), 6.28 (s, 2H, CH$_2$).

379e

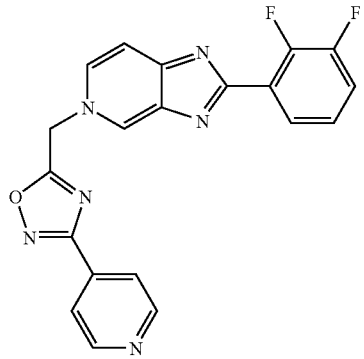

Prepared as described above, starting from pyridine-4-carbonitrile.

$^1$H NMR (200 MHz, DMSO-d$_6$) δ 9.24 (d, 1H, H4, J=1.4 Hz), 8.77 (AA'BB', 2H, pyridine-H2/6), 8.32 (dd, 1H, H6, J=7.0, 1.4 Hz), 8.15 (m, 1H, phenyl-H), 7.93 (d, 1H, H7, J=7.0 Hz), 7.86 (AA'BB', 2H, pyridine-H3/5), 7.51 (m, 1H, phenyl-H), 7.32 (m, 1H, phenyl-H), 6.32 (s, 2H, CH$_2$).

Part B

Methodology for Determination of Antiviral and Cytostatic Activity

Cells and Viruses

Madin-Darbey Bovine Kidney (MDBK) cells were maintained in Dulbecco's modified Eagle medium (DMEM) supplemented with BVDV-free 5% fetal calf serum (DMEME-FCS) at 37° C. in a humidified, 5% CO$_2$ atmosphere. BVDV-1 (strain PE515) was used to assess the antiviral activity in MDBK cells.

Anti-BVDV Assay

Ninety-six-well cell culture plates were seeded with MDBK cells in DMEM-FCS so that cells reached 24 hr later confluency. Then medium was removed and serial 5-fold dilutions of the test compounds were added in a total volume of 100 µL, after which the virus inoculum (100 µL) was added to each well. The virus inoculum used resulted in a greater than 90% destruction of the cell monolayer after 5 days incubation at 37° C. Uninfected cells and cells receiving virus without compound were included in each assay plate. After 5 days, medium was removed and 90 µL of DMEM-FCS and 10 µL of MTS/PMS solution (Promega) was added to each well. Following a 2 hr incubation period at 37° C. the optical density of the wells was read at 498 nm in a microplate reader. The 50% effective concentration (EC$_{50}$) value was defined as the concentration of compound that protects 50% of the cell monolayer from virus-induced cytopathic effect.

Anti-HCV Assay/Replicon Assay—1

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] was cultured in RPMI medium (Gibco) supplemented with 10% fetal calf serum, 2 mM L-glutamine (Life Technologies), 1× non-essential amino acids (Life Technologies); 100 IU/mL penicillin and 100 µg/ml streptomycin and 250 µg/mL G418 (Geneticin, Life Technologies). Cells were seeded at a density of 7000 cells per well in 96 well View Plate™ (Packard) in medium containing the same components as described above, except for G418. Cells were allowed to adhere and proliferate for 24 hr. At that time, culture medium was removed and serial dilutions of the test compounds were added in culture medium lacking G418. Interferon alfa 2a (500 IU) was included as a positive control. Plates were further incubated at 37° C. and 5% CO$_2$ for 72 hours. Replication of the HCV replicon in Huh-5 cells results in luciferase activity in the cells. Luciferase activity is measured by adding 50 µL of 1× Glo-lysis buffer (Promega) for 15 minutes followed by 50 µL of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cell culture plates (Becton-Dickinson) are treated in a similar fashion except that no Glo-lysis buffer or Steady-Glo Luciferase reagent is added. Instead the density of the culture is measured by means of the MTS method (Promega).

Quantitative Analysis of HCV RNA by Taqman Real-Time RT-PCR

Replicon cells were plated at 7.5×10$^3$ cells per well in a 96-well plate plates at 37° C. and 5% CO$_2$ in Dulbecco's modified essential medium containing 10% fetal calf serum, 1% nonessential amino acids and 1 mg/ml Geneticin. After allowing 24 h for cell attachment, different dilutions of compound were added to the cultures. Plates were incubated for 5 days, at which time RNA was extracted using the Qiamp Rneazyi Kit (Qiagen, Hilden, Gemiany). A 50 µL PCR reaction contained TaqMan EZ buffer (50 mmol/L Bicine, 115 mmol/L potassium acetate, 0.01 mmol/L EDTA, 60 mmol/L 6-carboxy-X-rhodamine, and 8% glycerol, pH 8.2; Perkin Elmer Corp./Applied Biosystems), 300 µmol/L deoxyadenosine triphosphate, 300 µmol/L deoxyguanosine triphosphate, 300 µmol/L deoxycytidine triphosphate, 600 µmol/L deoxyuridine triphosphate, 200 µmol/L forward primer [5'-ccg gcT Acc Tgc ccA TTc], 200 µmol/L reverse primer [ccA GaT cAT ccT gAT cgA cAA G], 100 µmol/L TaqMan probe [6-FAM-AcA Tcg cAT cgA gcg Agc Acg TAc-TAMRA], 3 mmol/L manganese acetate, 0.5 U AmpErase uracil-N-glycosylase, 7.5 U rTth DNA polymerase, and 10 µl of RNA elution. After initial activation of uracil-N-glycosylase at 50° C. for 2 minutes, RT was performed at 60° C. for 30 minutes, followed by inactivation of uracil-N-glycosylase at 95° C. for 5 minutes. Subsequent PCR amplification consisted of 40 cycles of denaturation at 94° C. for 20 seconds and annealing and extension at 62° C. for 1 minute in an ABI 7700 sequence detector. For each PCR run, negative template and positive template samples were used. The cycle threshold value (Ct-value) is defined as the number of PCR cycles for which the signal exceeds the baseline, which defines a positive value. The sample was considered to be positive if the Ct-value Was <50. Results are expressed as genomic equivalents (GE).

Anti-HCV Assay/Replicon Assay—2
HCV Replicon Media
DMEM w/High Glucose (or MEM)
1× Glutamine
1× Sodium Pyruvate
10% Heat Inactivated FBS
1× Antibiotics Cell Culture Preparation
1. Unthaw frozen stock in 10-12 mls of Media
2. Allow cells to attach before adding G418 (4-6 hrs)
3. Add G418 for a final concentration of 200 µg/mL (higher amounts are possible but cells grow slowly)
4. Split cells 1:4 to 1:6 for optimal growth
5. In-house replicon seems to maintain Luciferase signal for ~20 passages HCV Replicon Assay
1. Dilute compounds in 100 uL of HCV Replicon Media (without G418). If compounds are diluted in DMSO add DMSO to media (Final DMSO concentration should be <1%)
2. Once cells have reached 80-90% confluency, trypsinize with 1× Trypsin
3. Do not over trypsinize. These cells tend to clump if over trypsinized
4. For 96 well format add 6,000-8,000 cells per well (G418 is withheld during compound testing)
5. Incubate for 3 days at 37° C. Cells should be very close to confluent.
6. Remove media and wash cells with 1×PBS 7. Remove PBS and add 100 μL of 1× Promega Lysis Buffer
8. Incubate cells at Room Temperature for 5-20 minutes
9. Add 100 μL of room temperature Luciferase Substrate Solution (Promega) to Microfluor Black Plate (VWR)
10. Thoroughly Mix Cell lysate (pipet up and down) before adding to Luciferase substrate
11. Add 75 μL of lysate to the Luciferase substrate solution
12. Read Plate On Top Count (FusionLucB program ~5 second read)
13. Left over lysate can be frozen and used for later analysis Determination of Cytostatic Effect on MDBK Cells The effect of the drugs on exponentially growing MDBK cells was assessed as follows. Cells were seeded at a density of 5000 cell/well in 96 well plates in MEM medium (Gibco) supplemented with 10% fetal calf serum, 2 mM L-glutamine (Life Technologies) and bicarbonate (Life Technologies). Cells were cultured for 24 hr after which serial dilutions of the test compounds were added. Cultures were then again further incubated for 3 days after which the effect on cell growth was quantified by means of the MTS method (Promega). The concentration that results in 50% inhibition of cell growth is defined as the 50% cytostatic concentration ($CC_{50}$)

HCV CC50 Assay Protocol
HCV Replicon Media
DMEM w/High Glucose (or MEM)
1× Glutamine
1× Sodium Pyruvate
10% Heat Inactivated FBS
1× Antibiotics Cell Culture Preparation
1. Unthaw frozen stock in 10-12 mls of Media
2. Allow cells to attach before adding G418 (4-6 hrs)
3. Add G418 for a final concentration of 200 μg/ml (higher amounts are possible but cells grow slowly)
4. Split cells 1:4 to 1:6 for optimal growth
5. In-house replicon seems to maintain Luciferase signal for ~20 passages HCV Replicon Assay
1. Dilute compounds in 100 μL of HCV Replicon Media (without G418). If compounds are diluted in DMSO add DMSO to media (Final DMSO concentration should be <1%)
2. Once cells have reached 80-90% confluency, trypsinize with 1× Trypsin
3. Do not over trypsinize. These cells tend to clump if over trypsinized
4. For 96 well format add 6,000-8,000 cells per well (G418 is withheld during compound testing)
5. Incubate for 3 days at 37° C. Cells should be very close to confluent.
6. Remove media and add 200 μL of a 0.2 mg/mL MTT solution prepared in media.
7. Incubate for 1.5 hours to 2 hours.
8. Remove media and add 150 μL of DMSO
9. Mix and incubate for 5 mins at room temperature
10. Read plate at 530 nm in the plate reader.

Results

The compounds of Examples 2, 3A, 4 and 5 were found to have an EC50 in Replicon assay 2 of, respectively in micromoles, 0.01, 0.02, 0.01 and 0.0039, and to have a CC50 in the CC50 assay protocol of, respectively in micromoles, 26, 34, 19 and 10.8 (replicate 13.4).

Substantially all of the compounds in Table 1 demonstrated activity of at least 1 micromolar in an anti-HCV/Replicon assay system. In addition, a number of the compounds also exhibited anti-BVDV activity.

We claim:
1. A compound having the structural formula (A),

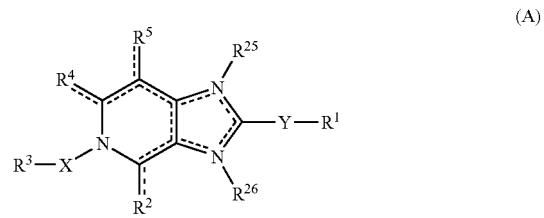

(A)

wherein:
the dotted lines represent an optional double bond, provided that no two double bonds are adjacent to one another, and that the dotted lines represent at least 3 double bonds;
$R^1$ is selected from the group consisting of hydrogen, aryl, heterocycle, $C_1$-$C_{10}$ alkoxy, $C_1$-$C_{10}$ thioalkyl, $C_1$-$C_{10}$ alkyl-amino, $C_1$-$C_{10}$ dialkylamino, $C_{3-10}$ cycloalkyl, $C_{4-10}$ cycloalkenyl, and $C_{4-10}$ cycloalkynyl, wherein each are optionally substituted with one or more $R^6$;
Y is selected from a single bond, O, S(O)$_m$, NR$^{11}$, $C_{1-10}$ alkylene, $C_{2-10}$ alkenylene, or $C_{2-10}$ alkynylene, wherein each alkylene, alkenylene or alkynylene optionally includes 1 to 3 heteroatoms selected from O, S or N;
$R^2$ and $R^4$ are independently selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, —SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, and heterocycle, or when one of $R^{25}$ or $R^{26}$ is present, $R^2$ or $R^4$ is selected from the group consisting of (=O), (=S), and =NR$^{27}$;
X is selected from the group consisting of $C_1$-$C_{10}$ alkylene, $C_{2-10}$ alkenylene and $C_{2-10}$ alkynylene, where each optionally includes one or more heteroatoms selected from the group consisting of O, S, or N, provided any such heteroatom is not adjacent to the N in the imidazopyridyl ring;
m is any integer from 0 to 2;
$R^3$ is a heterocycle substituted with one or more $R^{17}$, provided that $R^3$ optionally substituted with at least one $R^{17}$ is not pyridinyl or 5-chlorothienyl;
$R^5$ is selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle;
each $R^6$ is independently selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, —OH, —CN, cyanoalkyl, —CO₂R¹⁸, —NO₂, —NR⁷R⁸, C₁₋₁₈ haloalkyl, —C(=O)R¹⁸, —C(=S)R¹³, —SH, aryl, aryloxy, arylthio, arylsulfoxide, arylsulfone, arylsulfonamide, aryl(C₁₋₁₈)alkyl, aryl(C₁₋₁₈)alkyloxy, aryl(C₁₋₁₈)alkylthio, heterocycle and C₁₋₁₈ hydroxyalkyl, where each is optionally substituted with one or more R¹⁹;

R⁷ and R⁸ are independently selected from the group consisting of hydrogen, C₁₋₁₈ alkyl, C₁₋₁₈ alkenyl, aryl, C₃₋₁₀ cycloalkyl, C₄₋₁₀ cycloalkenyl, heterocycle, —C(=O)R¹², —C(=S)R¹², an amino acid residue linked through a carboxyl group thereof, or R⁷ and R⁸ are taken together with the nitrogen to form a heterocycle;

R⁹ and R¹⁸ are independently selected from the group consisting of hydrogen, —OH, C₁₋₁₈ alkyl, C₂₋₁₈ alkenyl, C₃₋₁₀ cycloalkyl, C₄₋₁₀ cycloalkenyl, C₁₋₁₈ alkoxy, —NR¹⁵R¹⁶, aryl, an amino acid residue linked through an amino group of the amino acid, —CH₂OCH(=O)R⁹ᵃ, and —CH₂OC(=O)OR⁹ᵃ where R⁹ᵃ is C₁-C₁₂ alkyl, C₆-C₂₀ aryl, C₆-C₂₀ alkylaryl or C₆-C₂₀ aralkyl;

R¹¹ is selected from the group consisting of hydrogen, C₁₋₁₈ alkyl, C₂₋₁₈ alkenyl, C₃₋₁₀ cycloalkyl, C₄₋₁₀ cycloalkenyl, aryl, —C(=O)R¹², heterocycle, and an amino acid residue;

R¹² is selected from the group consisting of hydrogen, C₁₋₁₈ alkyl, C₂₋₁₈ alkenyl, aryl, C₃₋₁₀ cycloalkyl, C₄₋₁₀ cycloalkenyl, or an amino acid residue;

R¹⁵ and R¹⁶ are independently selected from the group consisting of hydrogen, C₁₋₁₈ alkyl, C₂₋₁₈ alkenyl, C₂₋₁₈ alkynyl, aryl, C₃₋₁₀ cycloalkyl, C₄₋₁₀ cycloalkenyl, and an amino acid residue;

each R¹⁷ is independently selected from the group consisting of hydrogen, C₁₋₁₈ alkyl, C₂₋₁₈ alkenyl, C₂₋₁₈ alkynyl, C₁₋₁₈ alkoxy, C₁₋₁₈ alkylthio, C₁₋₁₈ alkylsulfoxide, C₁₋₁₈ alkylsulfone, C₂₋₁₈ halogenated alkenyl, C₂₋₁₈ halogenated alkynyl, C₂₋₁₈ halogenated alkoxy, C₁₋₁₈ halogenated alkylthio, C₃₋₁₀ cycloalkyl, C₃₋₁₀ cycloalkenyl, C₇₋₁₀ cycloalkynyl, halogen, OH, CN, NO₂, NR⁷R⁸, haloalkyl, C(=O)R¹⁸, C(=S)R¹⁸, SH, aryl, aryloxy, arylthio, CO₂H, CO₂R¹⁸, arylsulfoxide, arylsulfone, arylsulfonamide, arylalkyl, arylalkyloxy, arylalkylthio, heterocyclic, and C₁₋₁₈ hydroxyalkyl, where each of said aryl, aryloxy, arylthio, arylalkyl, arylalkyloxy, arylalkylthio, heterocycle, C₁₋₁₈ hydroxyalkyl, arylsulfoxide, arylsulfone, or arylsulfonamide is optionally substituted with one or more R¹⁹;

each R¹⁹ is independently selected from the group consisting of hydrogen, C₁₋₁₈ alkyl, C₂₋₁₈ alkenyl, C₂₋₁₈ alkynyl, C₁₋₁₈ alkoxy, C₂₋₁₈ alkenyloxy, C₂₋₁₈ alkynyloxy, C₁₋₁₈ alkylthio, C₃₋₁₀ cycloalkyl, C₄₋₁₀ cycloalkenyl, C₄₋₁₀ cycloalkynyl, halogen, —OH, —CN, cyanoalkyl, —NO₂, —NR²⁰R²¹, C₁₋₁₈ haloalkyl, C₁₋₁₈ haloalkyloxy, —C(=O)R¹⁸, —C(=O)OR¹⁸, —OalkenylC(=O)OR¹⁸, —OalkylC(=O)NR²⁰R²¹, —OalkylOC(=O)R¹⁸, —C(=S)R¹⁸, —SH, —C(=O)N(C₁₋₆ alkyl), —N(H)S(O)(O)(C₁₋₆ alkyl), aryl, heterocycle, C₁₋₁₈ alkylsulfone, arylsulfoxide, arylsulfonamide, aryl(C₁₋₁₈)alkyloxy, aryloxy, aryl(C₁₋₁₈ alkyl)oxy, arylthio, aryl(C₁₋₁₈)alkylthio or aryl(C₁₋₁₈)alkyl, where each is optionally substituted with 1 or more =O, —NR²⁰R²¹, —CN, C₁₋₁₈ alkoxy, heterocycle, C₁₋₁₈ haloalkyl, heterocycle alkyl, heterocycle connected to R¹⁷ by alkyl, alkoxyalkoxy or halogen;

R²⁰ and R²¹ are independently selected from the group consisting of hydrogen, C₁₋₁₈ alkyl, C₂₋₁₈ alkenyl, C₂₋₁₈ alkynyl, aryl, C₃₋₁₀ cycloalkyl, C₄₋₁₀ cycloalkenyl, —C(=O)R¹², carboxylester-substituted heterocycle, and —C(=S)R¹²;

R²⁵ and R²⁶ are not present, or are independently selected from the group consisting of hydrogen, C₁₋₁₈ alkyl, C₃₋₁₀ cycloalkyl, aryl and heterocycle, where each is optionally independently substituted with 1 to 4 of C₁₋₆ alkyl, C₁₋₆ alkoxy, halo, —CH₂OH, benzyloxy, and —OH; and R²⁷ is selected from the group consisting of hydrogen, C₁₋₁₈ alkyl, C₃₋₁₀ cycloalkyl, (C₃₋₁₀ cycloalkyl)-C₁₋₆ alkyl, aryl, and aryl(C₁₋₁₈)alkyl; and salts, tautomers, stereoisomers and solvates thereof.

2. A compound having the structural formula (C)

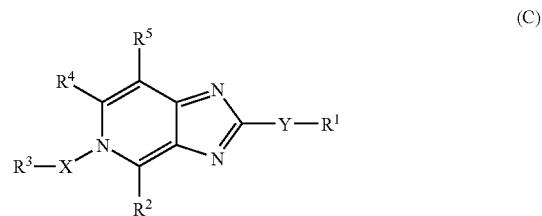

(C)

wherein:

R¹ is selected from the group consisting of aryl, heterocycle, C₁-C₁₀ alkoxy, C₁-C₁₀ thioalkyl, C₁-C₁₀ alkylamino, C₁-C₁₀ dialkylamino, C₃₋₁₀ cycloalkyl, C₄₋₁₀ cycloalkenyl, and C₄₋₁₀ cycloalkynyl, wherein each is optionally substituted with one or more R⁶;

Y is selected from a single bond, O, S(O)ₘ, NR¹¹, C₁₋₁₀ alkylene, C₂₋₁₀ alkenylene, or C₂₋₁₀ alkynylene, wherein each alkylene, alkenylene or alkynylene optionally includes 1 to 3 heteroatoms selected from O, S or N;

R² and R⁴ are independently selected from the group consisting of hydrogen, C₁₋₁₈ alkyl, C₂₋₁₈ alkenyl, C₂₋₁₈ alkynyl, C₁₋₁₈ alkoxy, C₁₋₁₈ alkylthio, halogen, —OH, —CN, —NO₂, —NR⁷R⁸, haloalkyloxy, haloalkyl, —C(=O)R⁹, —C(=S)R⁹, —SH, aryl, aryloxy, arylthio, arylalkyl, C₁₋₁₈ hydroxyalkyl, C₃₋₁₀ cycloalkyl, C₃₋₁₀ cycloalkyloxy, C₃₋₁₀ cycloalkylthio, C₃₋₁₀ cycloalkenyl, C₇₋₁₀ cycloalkynyl, and heterocycle;

X is selected from the group consisting of C₁-C₁₀ alkylene, C₂₋₁₀ alkenylene and C₂₋₁₀ alkynylene, where each optionally includes one or more heteroatoms selected from the group consisting of O, S, or N, provided any such heteroatom is not adjacent to the N in the imidazopyridyl ring;

m is any integer from 0 to 2;

R³ is aryl, aryloxy, arylthio, cycloalkyl, cycloalkenyl, cycloalkynyl, aryl-N(R¹⁰)—, or heterocycle, each of which is optionally substituted with one or more R¹⁷, provided that for cycloalkenyl the double bond is not adjacent to a nitrogen, provided M-Q-R³ is not biphenyl, and provided that R³ substituted with at least one R¹⁷ is not pyridinyl or 5-chlorothienyl;

R⁵ is selected from the group consisting of hydrogen, C₁₋₁₈ alkyl, C₂₋₁₈ alkenyl, C₂₋₁₈ alkynyl, C₁₋₁₈ alkoxy, C₁₋₁₈ alkylthio, halogen, —OH, —CN, —NO₂, —NR⁷R⁸, haloalkyloxy, haloalkyl, —C(=O)R⁹, —C(=O)OR⁹, —C(=S)R⁹, —SH, aryl, aryloxy, arylthio, arylalkyl, C₁₋₁₈ hydroxyalkyl, C₃₋₁₀ cycloalkyl, C₃₋₁₀ cycloalkyloxy, C₃₋₁₀ cycloalkylthio, C₃₋₁₀ cycloalkenyl, C₇₋₁₀ cycloalkynyl, and heterocycle;

each R⁶ is independently selected from the group consisting of hydrogen, C₁₋₁₈ alkyl, C₂₋₁₈ alkenyl, C₂₋₁₈ alkynyl, C₁₋₁₈ alkoxy, C₁₋₁₈ alkylthio, C₁₋₁₈ alkylsulfoxide, C₁₋₁₈ alkylsulfone, C₁₋₁₈ halo-alkyl, C₂₋₁₈ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, —OH, —CN, cyanoalkyl, —CO$_2$R$^{18}$, —NO$_2$, —NR$^7$R$^8$, $C_{1-18}$ haloalkyl, —C(=O)R$^{18}$, —C(=S)R$^{18}$, —SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio, heterocycle and $C_{1-18}$ hydroxyalkyl, where each is optionally substituted with one or more R$^{19}$;

R$^7$ and R$^8$ are independently selected from the group consisting of hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)R$^{12}$; —C(=S)R$^{12}$, and an amino acid residue linked through a carboxyl group thereof, or R$^7$ and R$^8$ are taken together with the nitrogen to form a heterocycle;

R$^9$ and R$^{18}$ are independently selected from the group consisting of hydrogen, —OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, an amino acid residue linked through an amino group of the amino acid, —CH$_2$OCH(=O)R$^{9a}$, and —CH$_2$OC(=O)OR$^{9a}$ where R$^{9a}$ is $C_1$-$C_{12}$ alkyl, $C_6$-$C_{20}$ aryl, $C_6$-$C_{20}$ alkylaryl or $C_6$-$C_{20}$ aralkyl;

R$^{10}$ and R$^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, heterocycle, and an amino acid residue;

R$^{12}$ is selected from the group consisting of hydrogen, $C_{1-18}$ alkyl $C_{2-18}$ alkenyl, aryl, $C_{3-10}$ cycloalkyl, $C_{4-10}$ cycloalkenyl, and an amino acid residue;

R$^{15}$ and R$^{16}$ are independently selected from the group consisting of hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, and an amino acid residue;

each R$^{17}$ is independently MQ- wherein M is a ring optionally substituted with one or more R$^{19}$, and Q is a bond or a linking group connecting M to R$^3$ that has 1 to 10 atoms and is optionally substituted with one or more R$^{19}$, wherein the linking group is alkylene optionally substituted with oxy or thioester;

each R$^{19}$ is independently selected from the group consisting of hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —NO$_2$, —NR$^{20}$R$^{21}$, $C_{1-18}$ haloalkyl, $C_{1-18}$ haloalkyloxy, —C(=O)R$^{18}$, —C(=O)OR$^{18}$, -OalkenylC(=O)OR$^{18}$, -OalkylC(=O)NR$^{20}$R$^{21}$, -OalkylOC(=O)R$^{18}$, —C(=S)R$^{18}$, —SH, —C(=O)N($C_{1-6}$ alkyl), —N(H)S(O)(O)($C_{1-6}$ alkyl), aryl, heterocycle, $C_{1-18}$ alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio or aryl($C_{1-18}$)alkyl, where each is optionally substituted with 1 or more =O, —NR$^{20}$R$^{21}$, —CN, $C_{1-18}$ alkoxy, heterocycle, $C_{1-18}$ haloalkyl, heterocycle alkyl, heterocycle connected to R$^{17}$ by alkyl, alkoxyalkoxy and halogen;

R$^{20}$ and R$^{21}$ are independently selected from the group consisting of hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)R$^{12}$, and —C(=S)R$^{12}$;

and salts, tautomers, and stereoisomers thereof.

3. A compound according to claim 1, wherein R$^3$ is isoxazolyl substituted with one R$^{17}$.

4. A pharmaceutical composition comprising a pharmaceutically acceptable excipient and a compound according to claim 1.

5. A pharmaceutical composition comprising a pharmaceutically acceptable excipient and a compound according to claim 2.

6. The compound of claim 1, wherein YR$^1$ is halophenyl or halomethyl-substituted phenyl.

7. The compound of claim 6, wherein halophenyl is ortho-fluorophenyl.

8. The compound of claim 1, wherein R$^{17}$ is aryl or a heterocycle further substituted with 1, 2 or 3 R$^{19}$.

9. The compound of claim 1, wherein YR$^1$ is not an unsubstituted $C_{3-10}$ cycloalkyl.

10. The compound of claim 1 wherein R$^{19}$ is trihalomethyl, trihalomethoxy, alkoxy or halogen.

11. The compound of claim 1, wherein R$^1$ is aryl or aromatic heterocyle substituted with 1, 2 or 3 R$^6$ and wherein R$^6$ is halogen, $C_{1-18}$ alkoxy or $C_{1-18}$ haloalkyl.

12. The compound of claim 1, wherein Y is a bond.

13. The compound of claim 1, wherein X is selected from the group consisting of —CH$_2$—, —CH(CH$_3$)—, —CH$_2$—CH$_2$—, —CH$_2$—CH$_2$—CH$_2$—, —CH$_2$—CH$_2$—CH$_2$—CH$_2$, —(CH$_2$)$_{2-4}$—O—(CH$_2$)$_{2-4}$—, —(CH$_2$)$_{2-4}$—S—(CH$_2$)$_{2-4}$—, —(CH$_2$)$_{2-4}$—NR$^{10}$—(CH$_2$)$_{2-4}$—, $C_{3-10}$ cycloalkylidene, $C_{2-6}$ alkenylene and $C_{2-6}$ alkynylene, wherein R$^{10}$ is selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, heterocyclic, and an amino acid residue.

14. The compound of claim 1, wherein X is methylene.

15. The compound of claim 1, wherein R$^3$ is a heterocycle substituted with 0 to 3 R$^{17}$.

16. The compound of claim 15, wherein the R$^3$ is an aromatic heterocycle.

17. The compound of claim 16, wherein the heterocycle contains 1, 2 or 3 N, S or O atoms in the ring, is linked to X through a ring carbon atom and contains 4 to 6 total ring atoms.

18. The compound of claim 1, wherein R$^{17}$ is selected from the group consisting of $C_{3-10}$ cycloalkyl, $C_{3-10}$ cycloalkenyl, $C_{7-10}$ cycloalkynyl, aryl, aryloxy, arylthio, arylsulfoxide, arylsulfone, arylsulfonamide, arylalkyl; arylalkyloxy; arylalkylthio and heterocycle, each being unsubstituted or substituted with 1 or more R$^{19}$.

19. The compound of claim 1, wherein R$^9$ and R$^{18}$ are H, OH or alkyl.

20. The compound of claim 1, wherein R$^5$ is H.

21. The compound of claim 1, wherein R$^6$ is halogen.

22. The compound of claim 1, wherein R$^7$, R$^8$, R$^{11}$, R$^{15}$, R$^{16}$, R$^{20}$, and R$^{21}$ are independently H or $C_{1-18}$ alkyl.

23. The compound of claim 1, wherein R$^{12}$ is OH or alkyl.

24. The compound of claim 1, wherein R$^{19}$ is selected from the group consisting of H; $C_{1-18}$ alkyl; $C_{2-18}$ alkenyl; $C_{2-18}$ alkynyl; $C_{1-18}$ alkoxy; alkenyloxy; alkynyloxy; $C_{1-18}$ alkylthio; $C_{3-10}$ cycloalkyl; $C_{4-10}$ cycloalkenyl; $C_{4-10}$ cycloalkynyl; halogen; OH; CN; cyanoalkyl; NO$_2$; NR$^{20}$R$^{21}$; haloalkyl; haloalkyloxy; C(=O)R$^{18}$; C(=O)OR$^{18}$; OalkenylC(=O)OR$^{18}$; -OalkylC(=O)NR$^{20}$R$^{21}$; aryl; heterocycle; -OalkylOC(=O)R$^{18}$; C(=O)N($C_{1-6}$ alkyl), N(H)S(O)(O)($C_{1-6}$ alkyl); arylalkyloxy; aryloxy; arylalkyloxy; and arylalkyl; each of which is unsubstituted or substituted with 1 or more =O; NR$^{20}$R$^{21}$; CN; alkoxy; heterocycle; haloalkyl- or alkyl-substituted heterocycle; and heterocycle linked to R$^{17}$ by alkyl; alkoxyalkoxy and halogen.

25. The compound of claim 24, wherein R$^{19}$ is independently selected from the group consisting of halogen, NR$^{20}$R$^{21}$, alkoxy, halo-substituted alkyl and halo-substituted alkoxy.

26. The compound of claim 1, wherein $R^{25}$ and $R^{26}$ are not present.

27. The compound of claim 1, wherein haloalkyl or haloalkyloxy is —$CF_3$ or —$OCF_3$.

28. The compound of claim 1, wherein Y is a single bond, and $R^1$ is phenyl.

29. The compound of claim 2, wherein Y is a single bond, and $R^1$ is aryl.

30. The compound of claim 2, wherein X is $C_1$-$C_{10}$ alkylene, $C_{2-10}$ alkenylene or $C_{2-10}$ alkynylene.

31. The compound of claim 2, wherein $R^3$ is a heterocyle.

32. The compound of claim 2, wherein $R^3$ is a heterocycle substituted with $R^{17}$ where Q is a bond and M is aryl.

33. The compound of claim 2, wherein $R^3$ is isoxazole substituted with $R^{17}$ where Q is a bond and M is aryl.

* * * * *

UNITED STATES PATENT AND TRADEMARK OFFICE
CERTIFICATE OF CORRECTION

PATENT NO. : 7,648,998 B2
APPLICATION NO. : 10/583814
DATED : January 19, 2010
INVENTOR(S) : Bondy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this

Twenty-third Day of November, 2010

David J. Kappos
*Director of the United States Patent and Trademark Office*